United States Patent
Papas et al.

(10) Patent No.: US 9,939,377 B2
(45) Date of Patent: Apr. 10, 2018

(54) METHOD OF FABRICATING TRANSLUCENT MATERIALS WITH DESIRED APPEARANCE

(71) Applicants: Marios Papas, Zurich (CH); Christian Regg, Emmenbrucke (CH); Steve Marschner, Ithaca, NY (US); Wojciech Jarosz, Zurich (CH); Wojciech Matusik, Lexington, MA (US); Philip J. Jackson, Glendale, CA (US); Bernd Bickel, Zurich (CH)

(72) Inventors: Marios Papas, Zurich (CH); Christian Regg, Emmenbrucke (CH); Steve Marschner, Ithaca, NY (US); Wojciech Jarosz, Zurich (CH); Wojciech Matusik, Lexington, MA (US); Philip J. Jackson, Glendale, CA (US); Bernd Bickel, Zurich (CH)

(73) Assignee: DISNEY ENTERPRISES, INC., Burbank, CA (US)

( * ) Notice: Subject to any disclaimer, the term of this patent is extended or adjusted under 35 U.S.C. 154(b) by 1168 days.

(21) Appl. No.: 13/935,712

(22) Filed: Jul. 5, 2013

(65) Prior Publication Data
US 2014/0198204 A1    Jul. 17, 2014

Related U.S. Application Data

(60) Provisional application No. 61/753,772, filed on Jan. 17, 2013.

(51) Int. Cl.
G01N 21/47    (2006.01)

(52) U.S. Cl.
CPC .. *G01N 21/4738* (2013.01); *Y10T 428/24942* (2015.01)

(58) Field of Classification Search
CPC .................................................. G01N 21/4738
See application file for complete search history.

(56) References Cited

U.S. PATENT DOCUMENTS

| 4,692,481 | A | 9/1987 | Kelly |
| 4,887,217 | A | 12/1989 | Sherman et al. |
| 2009/0254293 | A1* | 10/2009 | Tartaglia ................. G06T 15/50 |
| | | | 702/85 |

OTHER PUBLICATIONS

D'Eon, E. et al., "A quantized-diffusion model for rendering translucent materials", ACM Transactions on Graphics (Proc. SIGGRAPH) 30, 4, 56:1-56:14.

(Continued)

*Primary Examiner* — Stella K Yi
(74) *Attorney, Agent, or Firm* — Dorsey & Whitney LLP

(57) ABSTRACT

A method for creating a replication material corresponding to the appearance of a translucent or partially translucent target material. The appearance of the target material can be measured or may be prescribed by a user. The method includes receiving by a processor optical data related to a target subsurface scattering parameter of the target material. Once the processor has received the optical or light characteristic data, the method includes determining by the processor a replication pigment concentration to replicate the appearance of the target material caused by the target subsurface scattering parameter. The processor determines this concentration based on a plurality of pigment subsurface scattering parameters corresponding to a plurality of stored pigment concentrations in the computing device. Once the replication pigment concentration has been determined, the method includes creating, physically or virtually, the replication material by combining the pigment concentration with a base material.

13 Claims, 31 Drawing Sheets

(56) References Cited

OTHER PUBLICATIONS

Dong, Y. et al., "Fabricating spatially-varying subsurface scattering", ACM Transactions on Graphics (Proc. SIGGRAPH) 29, Jul. 4, 2010, 62:1-62:10.
Donner, C. et al., "An Empirical bssrdf model", ACM Transactions on Graphics (Proc. SIGGRAPH) 28, Jul. 3, 2009, 30:1-30:10.
Dorsey, J. et al., "Digital Modeling of Material Appearance", Morgan Kaufmann Publishers Inc., San Francisco, CA, USA, 2008.
Fuchs, M. et al., "Towards passive 6D reflectance field displays", ACM Transactions on Graphics (Proc. SIGGRAPH) 27, Aug. 3, 2008, 58:1-58:8.
Hasan, M. et al., "Physical Reproductions of Materials with Specified Subsurface Scattering", ACM Transactions on Graphics (Proc. SIGGRAPH) 29, Jul. 4, 2010, 61:1-61:10.
Hawkins, T. et al., "Acquisition of time-varying participating media", ACM Transactions on Graphics (Proc. SIGGRAPH) 24, Aug. 3, 2005, 812-815.
Hullin, M. B. et al., "Dynamic Display of BRDF's", In Computer Graphics Forum (Proc. Eurographics), 2011, 475-483.
Jakob, W., "Mitsuba renderer", found at http://mitsuba-renderer.org, 2010.
Jensen, H. W. et al., "A practical model for subsurface light transport", Computer Graphics (Proc. SIGGRAPH) 35, Aug. 2001, 511-518.
Jensen, H. W. et al., "A rapid hierarchical rendering technique for translucent materials", ACM Transactions on Graphics (Proc. SIGGRAPH) 21, Jul. 3, 2002, 576-581.
Matusik, W. et al., "Printing Spatially-varying reflectance", ACM Transactions on Graphics (Proc. SIGGRAPH Asia) 28, Dec. 5, 2009, 128:1-128:9.

Mitsunaga, T. et al., "Radiometric self calibration", In IEEE Conference on Computer Vision and Pattern Recognition (CVPR), vol. 1, 1999, 374-380.
Munoz, A. et al., "BSSRDF estimation from single images", Computer Graphics Forum (Proc. Eurographics) 30, 2011, 455-464.
Narasimhan, S. G. et al., "Acquiring scattering properties of participating media by dilution", ACM Transactions on Graphics (Proc. SIGGRAPH) 25, Jul. 3, 2006, 1003-1012.
Park, J.-I. et al., "Multispectral imaging using multiplexed illumination", In IEEE International Conference on Computer Vision (ICCV), 2007, 1-8.
Sharma, G. et al., "The ciede2000 color-difference formula: Implementation notes, supplementary test data and mathematical observations", Color Research and Application, 30, 1, 2005, 21-30.
Song, Y. et al., "Subedit: A representation for editing measured heterogeneous subsurface scattering", ACM Transactions on Graphics (Proc. SIGGRAPH) 28, Jul. 3, 2009, 31:1-31:10.
Wang, L. et al., "MCML: Monte Carlo modeling of light transport in multi-layered tissues", Computer Methods and Programs in Biomedicine, Jul. 8, 1995, 313-371.
Weyrich, T et al., "Fabricating microgeometry for custom surface reflectance", ACM Transactions on Graphics (Proc. SIGGRAPH) 28, Jul. 3, 2009, 32:1-32:6.
Weyrich, T. et al., "Analysis of Human Faces using a measurement-based skin reflectance model", ACM Transaction on Graphics (Proc. SIGGRAPH) 25, Jul. 3, 2006, 1013-1024.
Weyrich, T. et al., "Principles of appearance acquisition and representation", Foundations and Trends in Computer Graphics and Vision, 4, Oct. 2, 2009, 75-191.
Xu, K et al., "Real-time homogenous translucent material editing", Computer Graphics Forum (Proc. Eurographics) 26, Sep. 3, 2007, 545-552.

* cited by examiner

METHOD OF FABRICATING TRANSLUCENT MATERIALS WITH DESIRED APPEARANCE

CROSS REFERENCE TO RELATED APPLICATION

This application claims the benefit, under 35 U.S.C. § 119(e) of U.S. provisional application No. 61/753,772, entitled "Method of Replicating Materials" and filed on Jan. 17, 2013, which is hereby incorporated in its entirety by reference herein.

FIELD

The present invention relates generally to creating a material to match the appearance of a target material, and more specifically to creating a replication material to replicate the appearance of a target material having translucent properties.

BACKGROUND

The accurate representation of certain materials in both manufactured form, as well as in computer generated images, is challenging. For a high quality replication that looks "real," the appearance characteristics of the material should be accurately measured, quantified, and translated into physical characteristics (for a manufactured form) or software representations (for a computer generated image). Human skin is one such material, of many, for which an accurate replication is desired.

Processes exist for designing and fabricating real-life materials in an attempt to replicate life-like surfaces and make them appear real. For example, processes exist for developing a human-skin-like material to cover human models or animatronic items, such as robots, for use in live settings (such as amusement parks and museums). However, many existing fabrication processes and methods may ignore certain parameters of the replication material and/or target material in order to simplify the replication process. Thus, replicated materials made using these simplified processes may not appear as life-like, or sufficiently similar to, the targeted material for replication. In other instances, skilled artists may need to manually replicate these life-like materials at high cost and without the flexibility of a more automated process which relies less on the interpretation of the artist.

Computer generated images are used as content for various electronic visual media, such as movies, television, video games, software modeling, and other such items. In many instances it may be desirable to have the computer generated content accurately depict surfaces, textures, and colors. Some computer generated images model the appearance of a particular surface or material using rather simple analytical formulas that may include assumptions regarding certain subsurface light parameters. Due to these assumptions, images produced by these formulas may not sufficiently accurately match the properties of real materials to make the replication appear real.

For example, the light reflectance and color depiction of translucent materials may not be accurately represented in these earlier models because often times these formulas may ignore subsurface scattering within the material. Thus, many times replication of translucent materials may appear flat or not life-like.

It is with these shortcomings in mind that the present invention has been developed.

SUMMARY

One embodiment of the present disclosure may take the form of a method for creating a replication material matching the appearance of a translucent or partially translucent target material. The method includes receiving by a processor one or more optical or light characteristic data related to a target subsurface scattering parameter of the target material. Once the processor has received the material characteristic data, the method includes determining by the processor a pigment concentration to replicate the appearance of the target due to subsurface scattering. The processor determines this concentration based on a plurality of pigment subsurface scattering parameters corresponding to a plurality of stored pigment concentrations in the computing device. Once the replication pigment concentration has been determined, the method includes creating, physically or virtually, the replication material by combining the pigment concentration with a base material.

Another embodiment of the disclosure may take the form of a replication material having a set of subsurface scattering properties to match the appearance of a target material. The appearance of the target material can be measured and/or dictated by the user. The target material may have a target bulk scattering profile, a target diffuse reflectance, and a target sub surface scattering profile. The replication material may include a base material and a plurality of pigments intermixed with the base material. A concentration of the plurality of pigments is determined based on the target bulk scattering profile and the target diffuse reflectance profile of the target material. In the replication material, a replication sub surface scattering profile matches the appearance of the target material.

Yet another embodiment of the disclosure may take the form of a method for creating a pigment scattering parameter database. The method may include capturing by a camera at least one extinction coefficient image of a pigmented sample, at least one forward scattering image of the pigmented sample, and at least one back scattering image of the pigmented sample. Once the images have been captured, the method may further include analyzing by a processor the at least one extinction coefficient image, the at least one forward scattering image, and the at least one back scattering image to determine at least one of a phase function, a single scattering albedo, or an extinction coefficient of light transmitted through the pigmented sample. This method may also be used to measure a target material in order to capture one or more optical parameters of the target material to use to replicate that target material. In this example, the extinction coefficient image, forward scattering image, and/or back scattering image of the target may be captured and analyzed to determine the one or more optical properties.

SPECIFICATION

Overview

Figure 1A:
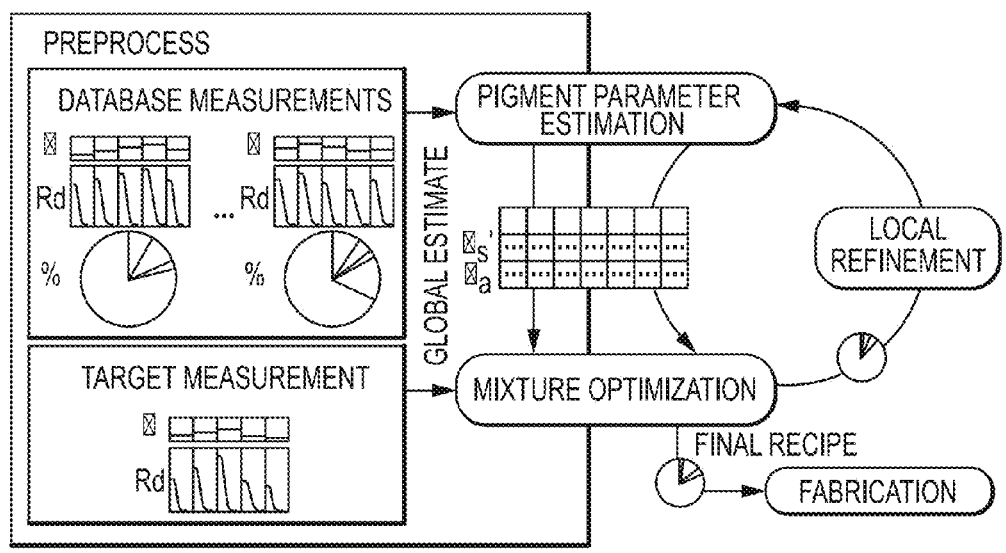
FIG. 1A is a simplified block diagram illustrating an overview of a method for replicating the appearance of a target material sample.
Figure 1B:
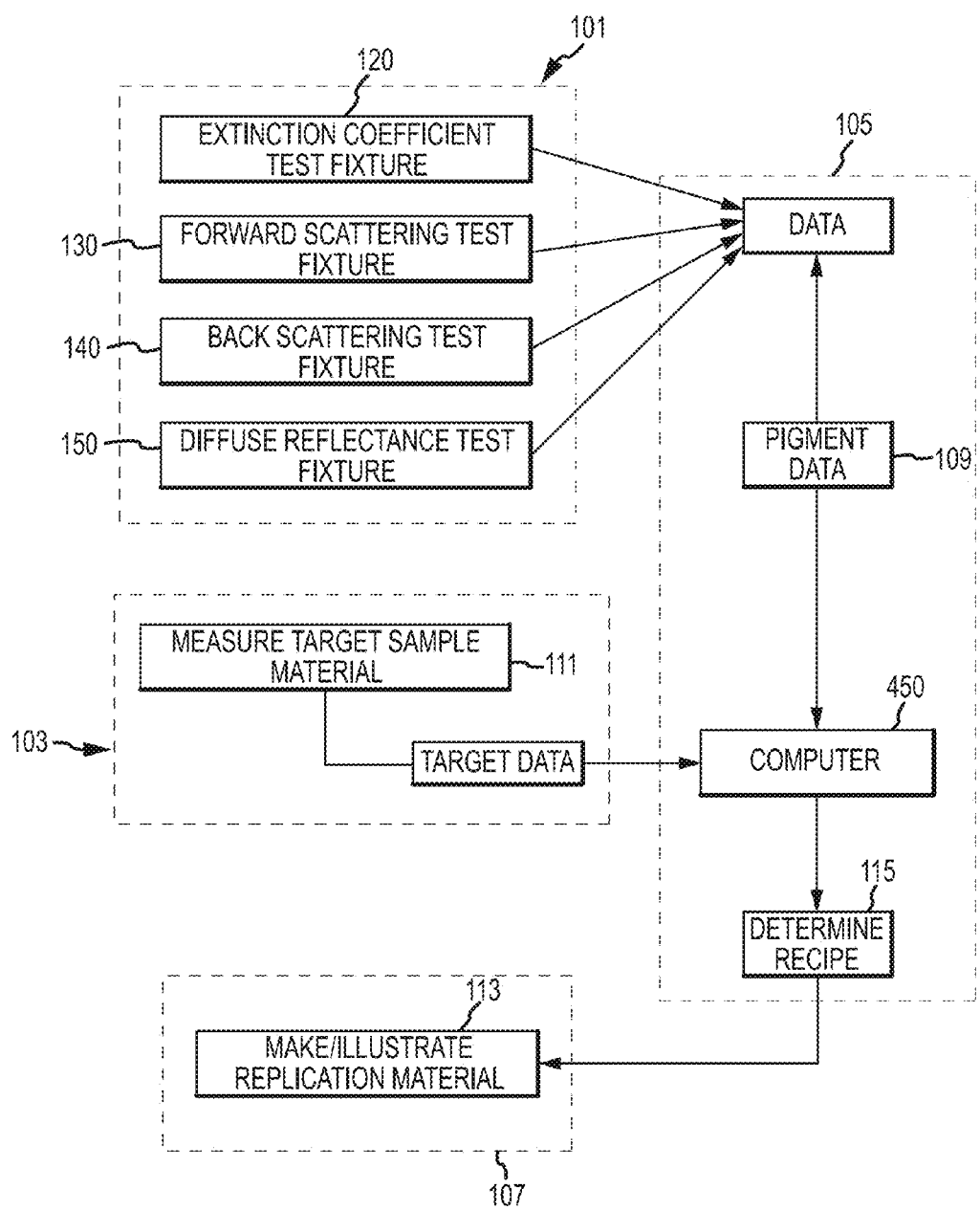
FIG. 1B is a more detailed diagram illustrating a first example of the method of FIG. 1A for replicating a target material sample.

Embodiments disclosed herein may relate to creating a replication material having substantially the same appearance and/or subsurface scattering (e.g., spectral characteristics or parameters) as a target material. FIG. 1A is a simplified block diagram illustrating various components of the disclosure. FIG. 1B is a more detailed diagram illustrating additional features of the disclosure. With reference to FIG. 1B, as shown generally in block 101, data corresponding to various pigments may be collected and analyzed. For example, a pigmented sample may be analyzed to determine certain spectral characteristics or reflectance profiles of each pigment. As used herein, the term pigmented sample is meant to describe a base material including one or more pigments suspended or otherwise mixed therein. For example, the base material may be water, silicone, or the like, and one or more color pigments may be mixed therein. The spectral characteristics or parameters for various pigments may be stored to create a database for numerous pigments.

As shown generally in block 103, a target material may be tested using a spectral measurement device. The spectral measurement device may be used to collect data to determine the spectral characteristics or parameters of the target material. With reference to block 105, using data collected with the spectral measurement device and the pigment database, a computer may determine a recipe or combination of pigments to create a replication material. As shown in block 107, the replication material may then be created, physically or virtually. The replication material may have substantially the same appearance of the target material and may include similar (or the same), spectral characteristics or parameters of the target material. In this manner, the parameters of various pigments may be combined in order to replicate the appearance of the target material.

With continued reference to block 101 in FIG. 1B, the method may include acquiring data from the pigmented sample to determine various desired parameters of the pigments in the pigmented sample. This data in turn may be used to create the database of pigments, which may be used to create a recipe for replication of the target material. The data acquired from pigmented sample includes one or more of the following: phase function, scattering albedo, bulk scattering profile, forward scattering, back scattering, and diffuse reflectance of a material. Each of these data samples are collectively referred to herein as optical data, spectral characteristics, test parameters, spectral parameters, scattering parameters, light-related parameters, or parameters. For example, block 101 may include an extinction coefficient test fixture 120, a forward scattering test fixture 130, a back scattering test fixture 140, and/or a diffuse reflectance test fixture 150 for determining these various parameters of a particular pigment within the pigmented sample. The pigmented sample may be tested in substantially any order. In some embodiments, the subsurface scattering and diffuse reflectance of the target material may be replicated as the appearance, especially of translucent materials, may depend on subsurface scattering. Subsurface scattering may generally be responsible for the translucency of a material as it is determines light that does not directly reflect from the surface of the material, but enters the material volume and remerges at another point. In instances where the subsurface scattering of a material is not modeled correctly, the material may appear flat and/or artificial.

Figure 1C:
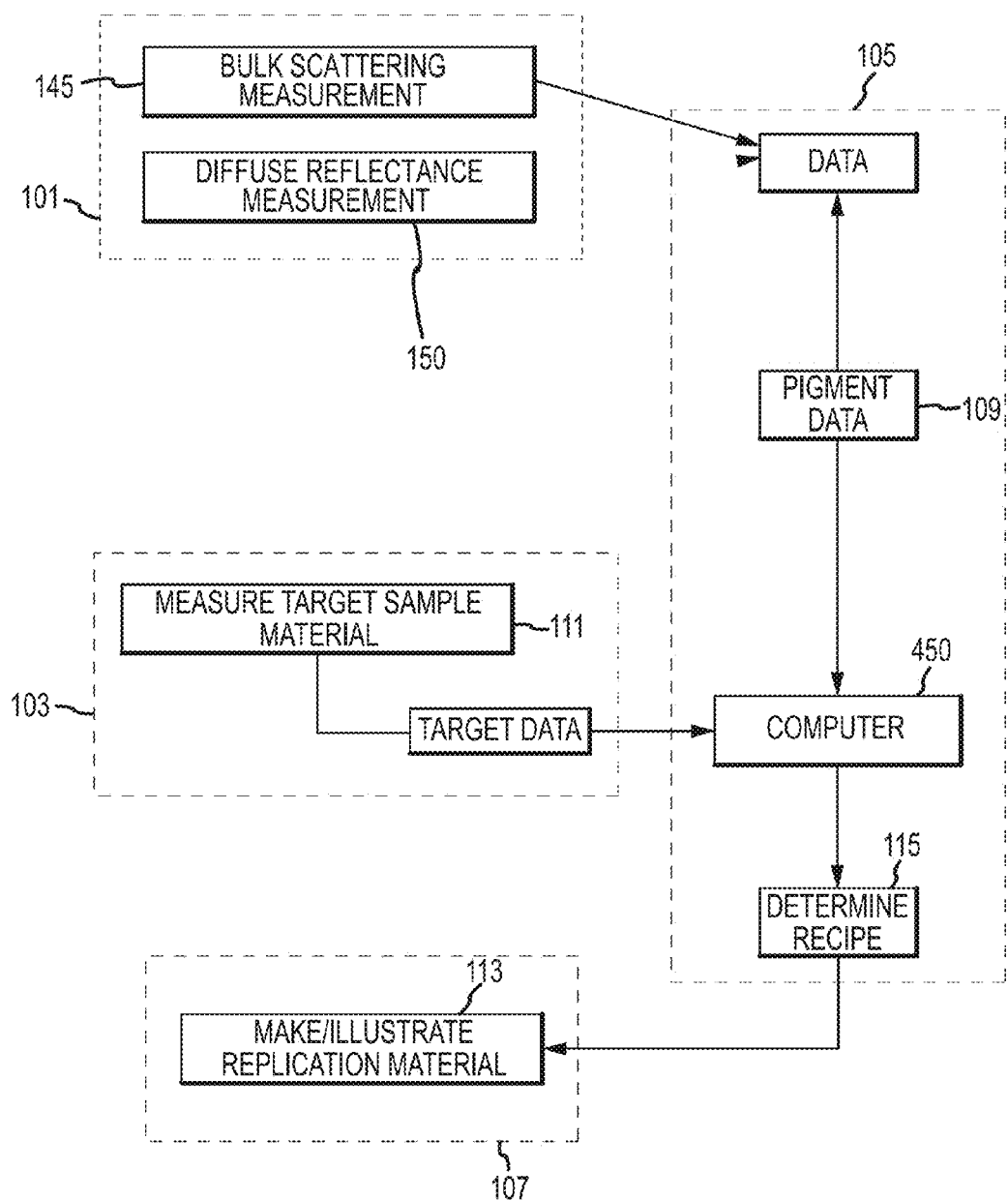
FIG. 1C is a more detailed diagram illustrating a second example of the method of FIG. 1A for replicating a target material sample.

In another example, the method may include taking two measurements from the pigmented sample and use those two measurements to determine one or more spectral characteristics or reflectance profiles for the pigmented sample. FIG. 1C is a block diagram illustrating a second example of the method illustrated in FIG. 1A. The method illustrated in FIG. 1C may be substantially similar to the method illustrated in FIG. 1B, but may measure the bulk scattering profile and diffuse reflectance of the pigmented sample without measuring the other parameters measured in FIG. 1B. This allows the pigmented samples to be tested quicker than in the previous method, but may not include as much information as measured in the method of FIG. 1C.

With continued reference to FIG. 1C, the bulk scattering profile of the pigmented sample may be measured as part of a bulk scattering measurement and the diffuse reflectance profile of the pigmented sampled may be captured as part of the diffuse reflectance measurement 150. These two measurements may be done in replace of or as a supplement to the extinction coefficient measurement, forward scattering measurement, and the back scattering measurement taken using the extinction coefficient test fixture 120, the forward scattering test fixture 130, and the back scattering test fixture 140, respectively. In this example, the data from the bulk scattering measurement 145 and the diffuse reflectance measurement 150 may be provided to the computer 450 and pigment database.

Using the various test fixtures or measurement systems illustrated in both FIGS. 1B and 1C, along with mathematical estimations, described in more detail below, an estimation of the scattering properties or reflectance profiles of each pigmented sample (e.g., each different pigment color and particular pigment concentration) may be measured, analyzed, and recorded in the database for later use in analyzing against a target material to be replicated. For example, a global set of pigment parameters for predicting the subsurface scattering appearance of material may be determined. The pigment parameters may include optical parameters relating to the color of the pigment, the concentration of the pigment, and the base material for the pigmented sample.

With reference to FIGS. 1A-1C, measuring and analysis of the test results of the target material samples may be, for example, by way of a non-linear optimization process, fitting process, or the like. The data collection and test results may be used to create a database of information over a range of pigmented samples and pigment loading or concentrations relating the test result data to the known samples. In one example, parameter data is collected from the pigmented samples having containing a predetermined concentration of a particular pigment to collect and create a database or aggregation of test data corresponding to the known pigment colors and/or concentrations contained in the pigmented sample.

Using the estimation of scattering properties for various concentrations of each known pigmented sample, the appearance of a replication material having substantially any concentration of the pigment may be determined, as shown in block 107 in FIGS. 1B and 1C. Further, by repeating this process for each, or many, pigments available, a prediction of the entire range or gamut of subsurface scattering parameters for a given selection of available pigments may be determined. In other words, the method may determine a range of potential sub surface scattering surface parameters that can be used to match against similar test results for a target material to be replicated, and thus the replication or copy may be made more accurate. This information will be used to match the results of similar tests on a target material with unknown pigment content that is to be replicated.

With reference to FIGS. 1A-1C, the method may also include acquiring the bulk scattering profile and diffuse reflection parameters of a target material. Data gathered from the target sample may be done as desired to replicate a particular material. The target material may be the material to be replicated by the replication material (either virtually or physically). For example, the target material may be skin (human, animal), organic material (plants), non-organic material (marble, rock formations, mud/sand), organisms, wax, and so on. In some instances a target sample of the target material may be tested using a substantially non-invasive spectral measurement device. The spectral measurement device may allow for data collection of the desired physical characteristics of the target sample without requiring the target material to be removed from its structure, or to be formed into a certain sample size or shape (such as a thin membrane), or immersed in a tank with a light source, or the like.

Once the parameters for the target material are determined or predicted, these data are compared against the database of sample data created from testing the pigmented sample, as described above. A comparison against the database information helps define a recipe of the amounts and/or concentrations of particular pigments (individual or a mixture) for use in designing the replication material to have an appearance that matches those of the selected light parameters. For example, given the desired light parameters related to the target material, a computer may determine, through reference to the database of information from the pigmented sample testing and other processing steps, a combination of various pigments and pigment concentrations estimated or calculated to accurately reproduce the target material. In other words, the method may determine a recipe for creating the replication material having the same appearance which may be by approximating or replicating the bulk scattering profile, diffuse reflectance, and/or subsurface scattering parameters as the target material. For example, an optimization process may be used to compute the concentrations of pigments for the target material.

In some instances, the recipe and/or optimization process may be modified to take into account a desired color space for the replicated material. For example, the recipe for creating the replication material may be modified based on the color spectrum visible by humans. In this example, the replication material may not technically match the appearance of the target material, but may visually (as perceived by a human) exactly match the appearance. This allows for a better correspondence between the target material and the replication material as perceived by a human.

The method may also include acquiring select parameters of the target material and using the pigmented sample parameters to determine a recipe for the concentration of target material samples to create a replication material corresponding to the target material. This is shown, for example, in blocks 103, 105, and 107 in FIGS. 1B and 1C. In block 103, the target sample may be measured as shown in block 111 and data corresponding to various parameters of the target material may be determined. Once the target material data is determined, a computer 450 or other device may determine a recipe as shown in block 115 for replicating the parameters of the target material. For example, the computer 450 may determine the particular concentrations and/or colors for various pigments which may be needed in order to create a material that may have substantially the same parameters as the target material.

The replication material may be represented and/or created by adjusting various pigment levels or concentrations and/or colors in the base material using the target material sample parameters. It should be noted that in some embodiments, the replication material may be physically created (e.g., a model); and, in other embodiments, the replication material may be a computer rendition (e.g., using computer animated graphics).

In some instances, after or as the replication material is created it may be molded or otherwise manipulated or formed to create the desired physical appearance, such as a specific part of the target material. For example, the replication material may be applied in layer form onto a substrate to result in the same shape of the target material, or into a custom desired shape (e.g., the face of a human). The replication material may also be created by a three-dimensional (3-D) printer capable of applying the appropriate print media and pigment in the desired shape of the target material. The replication material may also be configured or formed in any number of other ways, such as by casting, injection molding, spay application, sheet-layer application, or the like.

It is also contemplated that a target material may include many different designed replication materials applied to different parts of the same physical model to create a more real appearance. For example, to replicate a human body, each section of the body, e.g., arms, legs, face, back, etc., may require a different replication material to better replicate the subsurface scattering and visible colors. This is because a person may have veins visible through his or her skin, moles, and so on that may vary the "recipe" for the replication material for the particular area. Similarly, for other target materials other layering and/or pigment combinations may be used to replicate different portions of the target sample. Thus, there may be a plurality of replication materials connected together or otherwise formed to replicate an entire target material.

It should be noted that the techniques and methods disclosed herein may model not only the color of a material and the diffuse surface reflection of the material, but may also model the material as a volume including its corresponding subsurface scattering effects. These methods may also the modeling to extend beyond just color matching to allow modeling of translucent materials with significant subsurface scattering. Additionally, the methods and techniques disclosed herein may be used to replicate substantially any material where pigments manipulate the appearance of that material. For example, the methods may create replication materials such as restorative materials (e.g., crowns, dentures) in dentistry applications, prosthetics, animatronics (e.g., matching synthetic skin), as well as manufacturing artificial silicone plants, food, or other items. In other words, many liquid and solid materials may be replicated using the techniques described herein.

Replication Material Properties Acquisition

Creating the Pigmented Sample

Figure 2:
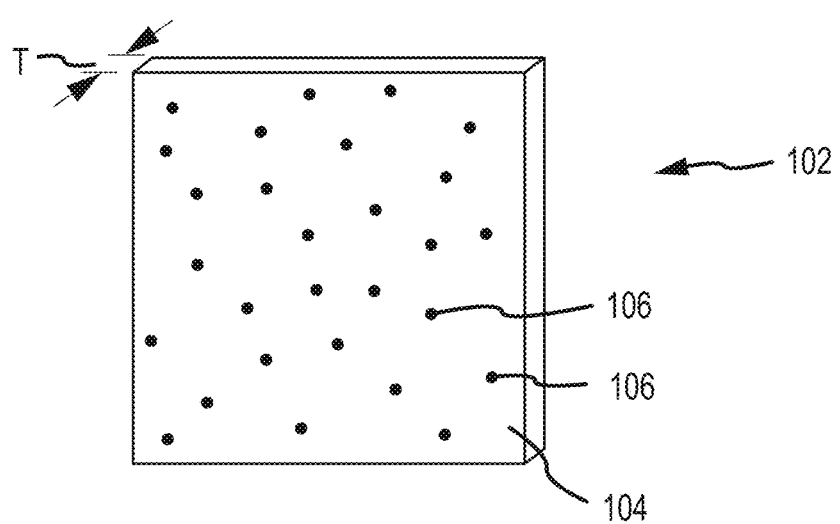
FIG. 2 is a perspective view of a pigmented sample having pigment particles positioned within a base material.

Turning now to FIG. 2, the pigmented sample will now be discussed in further detail. FIG. 2 is a perspective view of a pigmented sample 102. The pigmented sample 102 may include a base material 104 and pigment particles 106 dispersed therein at a known concentration. Examples of pigment colors include red, green, blue, yellow, white, and black. The pigmented sample 102 may be substantially any shaped desired, depending on the testing to be administered, and the test fixture used to secure the sample while measurements are taken. It should be noted that the size, shape, material, and pigment particle concentration is known for the pigmented sample 102.

In some embodiments, the pigmented sample 102 may be substantially homogenous, in that it may have substantially the same properties (i.e., pigment concentration) throughout the sample 102. However, in other embodiments, the pigmented sample 102 may be non-homogenous. This may include having different concentrations of the same pigment in different areas of the sample. It might also include having a known lamination of base materials with the same concentration of a known pigment in each layer. Many other permutations of the physical characteristics of the pigmented sample are possible in order to collect, with the intent of creating variations that will assist in matching the light parameters of a target material for accurate replication. A pigmented sample 102 may be created for each different color pigment particle 106, so that depending on the desired number or different pigments, there may be substantially any number of pigmented samples 102 created. The pigment particles 106 may represent the aggregate scattering properties of the pigmented sample 102.

In some examples, one or more pigmented dilution sets may be created. The pigmented dilution sets may be used to determine the parameters of each pigment individually. To create one or more pigmented dilution sets, a low concentration of pigment particles 106 may be combined with the base material 104 to create a diluted sample. In one example, each pigmented sample 102 may include a colored pigment and a white pigment. The white pigment may be mixed in at a low concentration, such at or lower than 0.05%. Additionally, a minimum amount of pigment may be used such that the color and bulk scattering profile of the colored pigment differentiate sufficiently from the appearance of the low concentration of the white pigment. In this example, a separate set of pigment samples including only white pigment is also created and tested, so that the scattering parameters of the white pigment can be distinguished from the base material. However, it should be noted that the concentration of one or more pigments within the base material may be modified based on a number of different factors or as desired and the above listed concentrations are meant as illustrative only.

The dilution sets may allow the parameters for each pigment to be determined. The dilution sets may be used to supplement pigmented samples having varying pigment concentrations (e.g., not diluted) or may be used to extrapolate the parameters of more concentrated samples.

The base material 104 may be a substantially clear material. In some embodiments, the base material 104 may be a silicone material, one example of which is SORTA-CLEAR40 produced by SILICONES, INC. However, in other embodiments, other base materials may be used, such as water, rubbers plastics, and the like. The base material may be varied based on the desired target material to be created. For example if the target material is a liquid, the base material may also be a liquid.

In some examples, the base material 104 may be a curable material and, as such, may be in a liquid or liquid-like form such as gel before being cured. In the un-cured state, the pigment particles 106 may be mixed into the base material 104 and the pigmented sample 102 may then be poured, injected, or otherwise positioned within a mold. The transparency of the base material 104 and the low concentration dilution of pigment particles 106 may allow light within the pigmented sample 102 to be primarily singly scattered rather than multi-scattered, which may allow for an easier and/or more accurate estimation of select scattering properties. For example, the phase function, and other parameters of the sample may be better determined if only single scattering in the pigmented sample 102 when tested, light may be not be internally reflected and re-scattered throughout the pigmented sample 102. This is because in single scattering light may enter the pigmented sample 102 encounter a pigment particle 106 and then exit the pigmented sample 102. On the contrary, with multiple scattering, light may enter a material and bounce on multiple particles before exiting the material, which may make determining certain parameters more difficult.

Figure 3A:
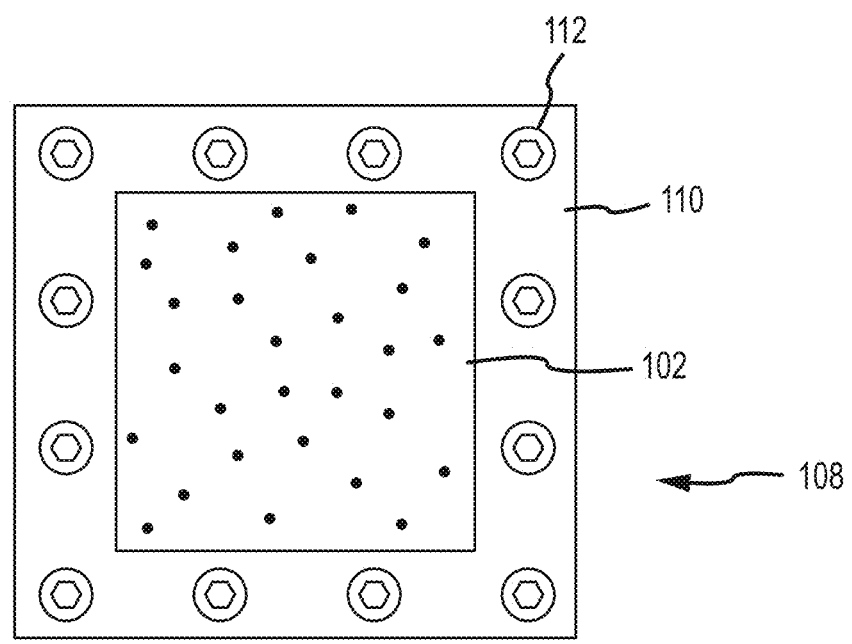
FIG. 3A is a front elevation view of the pigmented sample positioned within a securing device.
Figure 3B:
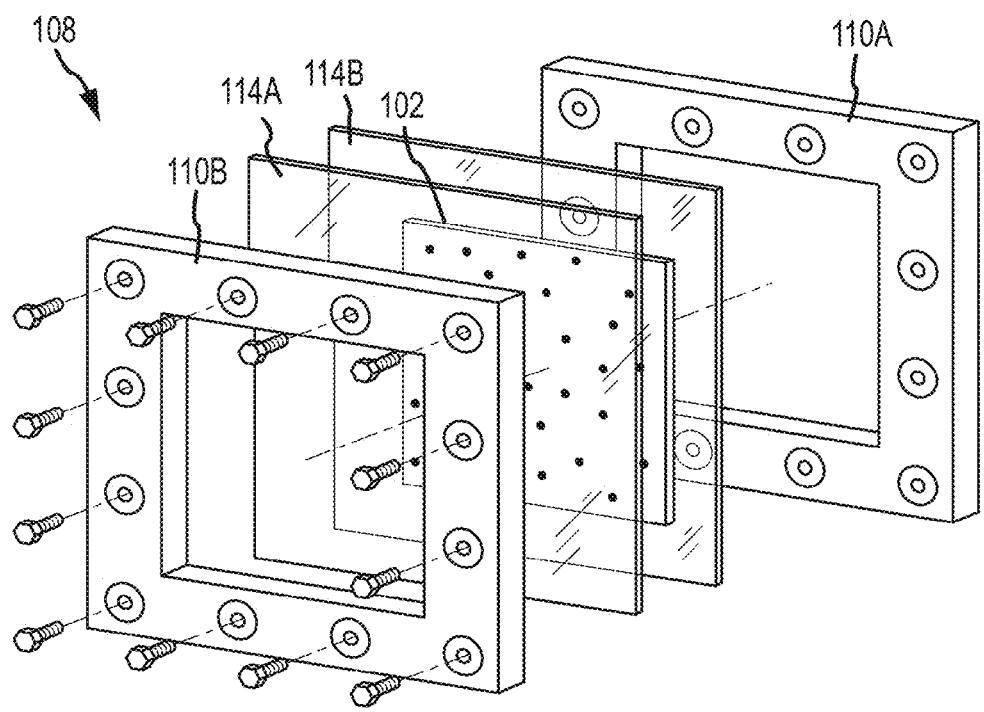
FIG. 3B is an exploded view of the pigmented sample and the securing device of FIG. 3A.

In some embodiments, a thickness T of the pigmented sample 102 may be regulated to reduce the complexity of light paths traveling through the pigmented sample 102 and to better preserve the directionality of light as enters and exits the target material sample. FIG. 3A is a front elevation view of the pigmented sample 102 secured within a securing device 108. FIG. 3B is an exploded view of the pigmented sample 102 and the securing device 108. The securing device 108 may restrict the size and/or thickness of the pigmented sample 102. The securing device 108 may include two plates 114A, 114B clamped together by an adhesive or shim tape. The plates 114A, 114B may be further clamped by bars 110A, 110B secured with fasteners 112 that may disperse pressure applied by the plates 114A, 114B to the pigmented sample 102 evenly throughout the pigmented sample 102, which may prevent the plates 114A, 114B from bending. Other securing devices or mechanisms may also be suitable for positioning the material for this test. For example, the thickness of the pigmented sample 102 may be regulated in other manners and/or may be supported within the various test fixtures by other devices.

With reference to FIGS. 3A and 3B, in some embodiments, the plates 114A, 114B may be acrylic or other transparent material (e.g., clear plastic, glass, and so on). The plates 114A, 114B are clear or transparent in order to not interfere with the testing by allowing light to be transmitted therethrough so that the light scattering properties of the pigmented sample 102 may be determined while the pigmented sample 102 may be held in position by the securing device 108. In some examples, the plates 114, 114b may have a thickness ranging between 4 to 8 mm, and in some instances the thickness may be approximately 6 mm in order to reduce the overall thickness of the pigmented sample 102 and the securing device 108. The shim tape or adhesive securing the two plates 114A, 114B together may range between 0.5 to 1 mm thick. In examples using the shim tapes, the tapes may be metallic tapes that are machined with high precision and used to control the thickness of the sample. The bars 110A, 110b may be precision steel bars or other clamping mechanism for dispersing pressure evenly on the pigmented sample 102.

The base material 102 and pigment particles 106 may be combined together and positioned within the plates 114A, 114B before the base material 104 cures. Once the pigmented sample 102 is positioned within the plates 114A, 114B, the bars 110A, 110B may be secured by the fasteners 112 to the plates 114A, 114B around a perimeter of the pigmented sample 102.

As briefly mentioned above, the thickness of the pigmented sample 102 may be selected in order to reduce the complexity of light paths within the pigmented sample 102. For example, the thinner the pigmented sample 102, the easier it may be to predict the appearance of the pigmented sample 102 given a set of estimated scattering properties. This is because scattering paths of light entering and exiting the pigmented sample 102 may be limited to low order scattering regime, which can be easier to simulate using Monte Carlo rendering techniques such as path tracing. The thickness of the pigmented sample 102 may also be chosen to more accurately represent the target materials likely to be replicated.

Additionally, the thickness of the pigmented sample 102 may also be selected based on directionality of the light. The thinner the pigmented sample 102 the more likely that the directionality of light entering and exiting the pigmented sample 102 may be preserved. If the thickness of the pigmented sample 102 is increased, the directionality of the light may be non-recoverable, thus reducing or further complicating the estimation of the scattering parameters of the pigmented sample 102. Also, it should be noted that in some examples, the pigmented sample 102 may have one or more layers. In these instances, the overall thickness of the pigmented sample 102 may include the thickness of each individual layer.

As shown in FIG. 3A, in some embodiments, the bars 110A, 110B may be positioned so that the pigmented sample 102 is viewable through the securing device 108. In some embodiments, it may be desirable to test the pigmented sample 102 (as discussed in more detail below) while the pigmented sample 102 is positioned within the securing device 106. For example, in some instances, even after the base material 104 has cured or hardened, the pigmented sample 102 may remain positioned between the plates 114A, 114B. This is because in some instances, after curing, if the pigmented sample 102 were removed from the plates 114A, 114B, the base material 104 may stretch or surface roughness may be introduced to the base material 104. However, in other embodiments, the pigmented sample 102 may be removed from the securing device 108 after it has been cured. For example, a mold release or other removal agent may be positioned on the plates 114A, 114B to assist in removing the pigmented sample 102.

The above fabrication steps and structures used for the pigmented sample help to increase the testing characteristics of the pigmented sample. For example, in some instances it may be desired to reduce or avoid air or other impurities from becoming intermixed with the pigmented sampled, preserving homogeneity and another factor to be considered is that often one side of the pigmented sample is near-specular. The above fabrication process of the pigmented sample helps to control these issues to achieve a low level of impurities and have at least one side of the pigmented sample that is specular. However, It should be noted that in some examples, the pigmented sampled may be created in a number of different manners.

Testing the Pigmented Sample

First Example

Figure 4:
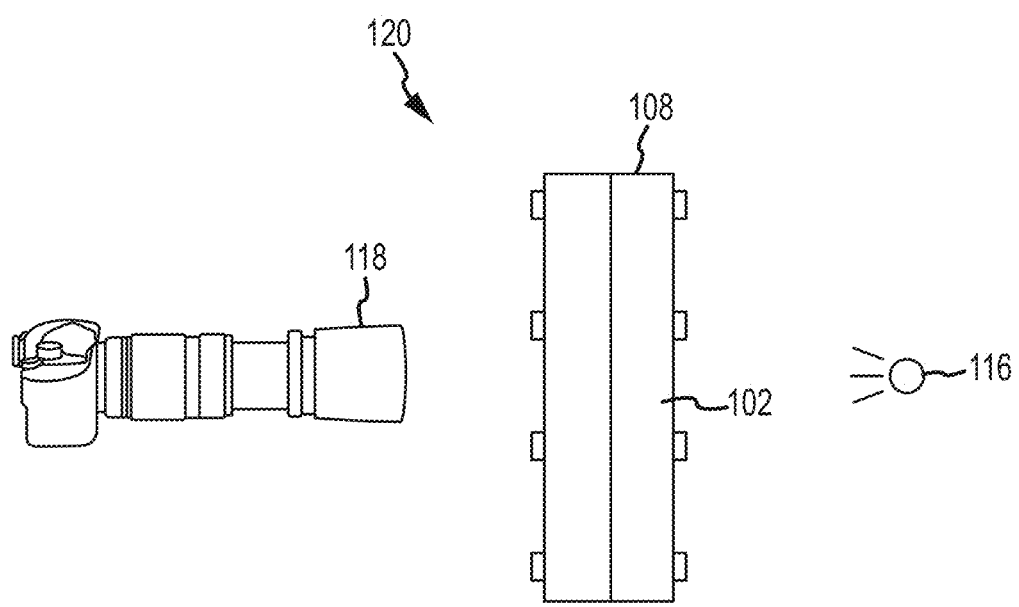
FIG. 4 is a side elevation view of an extinction coefficient test fixture.

The pigmented sample 102 may be subjected to various testing protocols to measure certain light scattering properties for each pigmented sample having a known pigment content or loading, e.g., the multi-spectral reflection profile. The properties for each pigmented sample 102 that may be determined by the testing may include phase function, scattering albedo, bulk scattering profile, forward scattering, back scattering, and diffuse reflectance. The various tests described in more detail below, may allow more accurate modeling of translucent materials which may have significant subsurface scattering as the various parameters for each pigment may be determined. For example, by testing the various pigmented samples, a mapping from pigment concentrations to reflection profiles that capture subsurface scattering properties can be created. FIG. 4 is a top perspective view of an extinction coefficient test fixture 120. In this test fixture 120, the resulting test images captured may be analyzed to determine the extinction coefficient of the pigmented sample 102. As shown in FIG. 4, the pigmented sample 102 held by the securing device 108 may be positioned between a light source 116 and a camera 118.

The light source 116 may be substantially any type of light source. In some embodiments, the light source 116 may be one or more fiber optic cables or other light transmitting devices (e.g., light tube or light guide) in optical communication with a light such as a light emitting diode (LED). For example, in one embodiment, the light source 116 may be a diffusely coated fiber optic cable optically coupled to one or more high-powered LED operating at approximately 150 mA. In other examples, the light source 116 may be a direct light source (e.g., a LED positioned directly next to or near the pigmented sample 102). Furthermore, the light source 116 may be substantially any color of light. In some embodiments, the color of the light source 116 may be varied between images being captured by the camera 118 in order to better obtain spectral sampling of the extinction coefficient of the pigmented sample 102. For example, the light source 116 may range between royal blue, cyan, green, amber, red, or the like to create the spectral range for the testing procedure. In some examples, the light source 116 may include a plurality of lights, such as 5 separate lights, with each light being a different color. The varying colors are configured to illuminate the pigmented sample with different light wavelengths to determine the spectral properties for each wavelength band for the pigmented sample.

The camera 118 or image capture device may be substantially any type of device including an image sensor (e.g., charged-coupled device or active pixel sensor) and a lens. For example, the camera 118 may be a digital camera that may communicate with a computing device or may store images on an internal or external memory card. (See e.g., FIG. 17). The camera may be a grayscale or monochromatic camera or may be a camera sensitive to spectral lights. In some embodiments, in instances where the camera is grayscale, the LED may include a plurality of lights that may emit different colors or spectrums. In other embodiments where the camera captures colors, the LED may emit a white light. In these embodiments, the camera may include a color filter (e.g., Bayer filter) over a portion or the entire image sensor and may be sensitive to one or more spectral wavelengths. In some examples, a RETIGA-2000R grayscale camera including a NAVITAR ZOOM-7000 MACRO LENS or a QImaging Retiga-200R camera may be used. However, other cameras 118 are envisioned.

With continued reference to FIG. 4, in the extinction coefficient test fixture 120, the light source 116 may be positioned substantially perpendicular to the pigmented sample 102 at a distance ranging between 100-200 mm from the pigmented sample 102. Although, it should be noted that in this test fixture 120, the light source 116 may be positioned at substantially any distance from the pigmented sample 102 as exact distance of the light source 116 to the pigmented sample 102 may not be required. In some embodiments, the camera 118 may be located at a distance ranging between 200 to 300 mm from the pigmented sample 102, on the opposite side of the pigmented sample 102 from the light source 116. In one example, the camera 118 may be positioned approximately 276 mm from the pigmented sample 102.

Figure 5A:
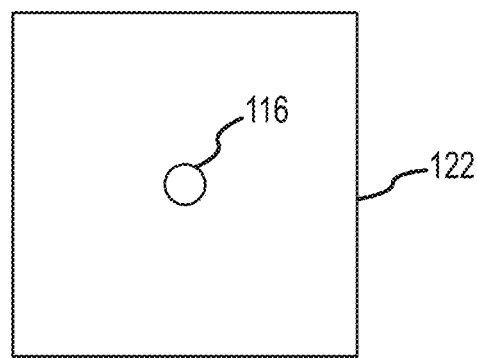
FIG. 5A is a front elevation view of a light extinction coefficient image captured using the extinction coefficient setup of FIG. 4.
Figure 5B:
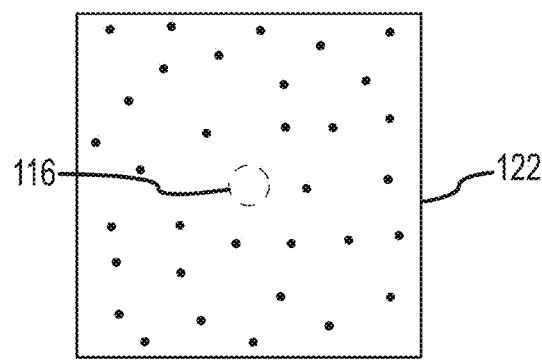
FIG. 5B is a front elevation view of a sample extinction coefficient image captured using the extinction coefficient setup of FIG. 4.
Figure 5C:
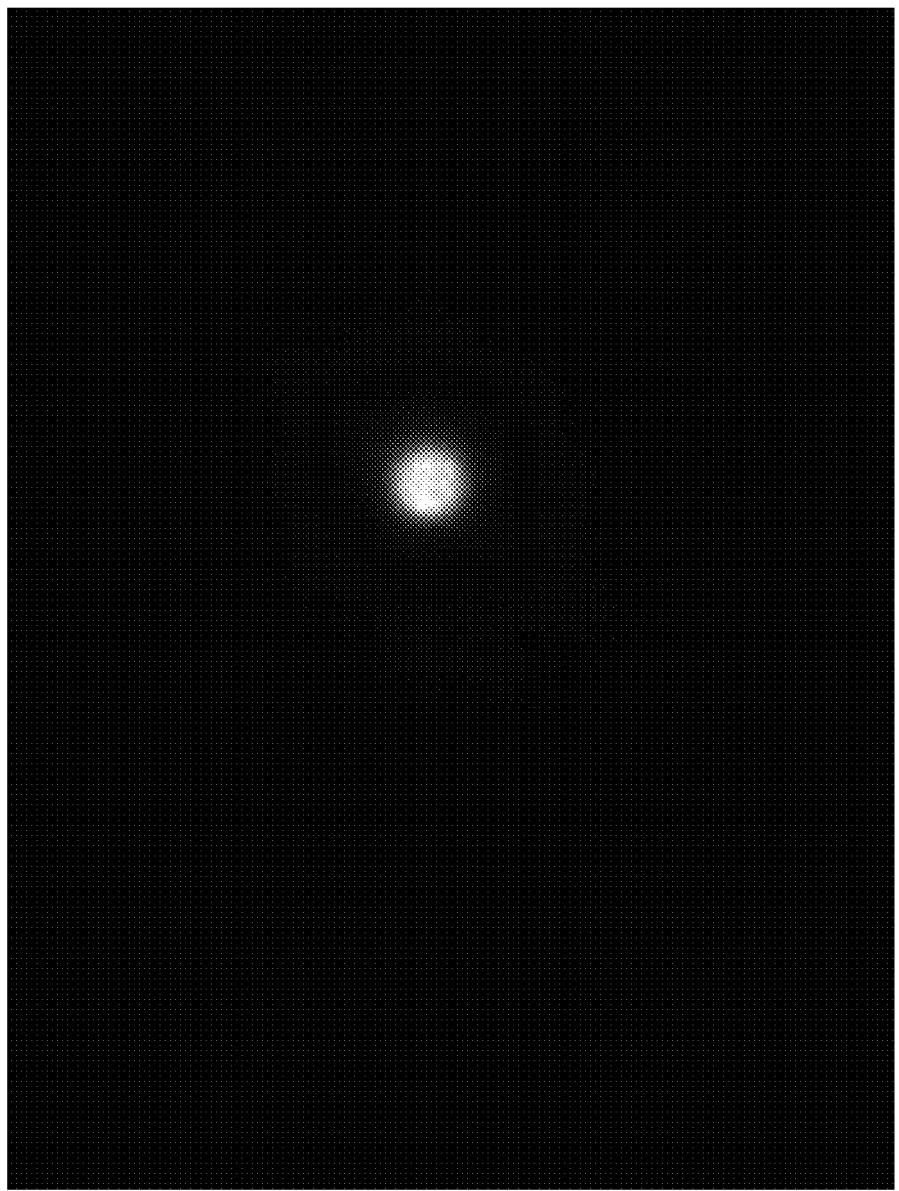
FIG. 5C is a front elevation view of another sample light extinction coefficient image.
Figure 5D:
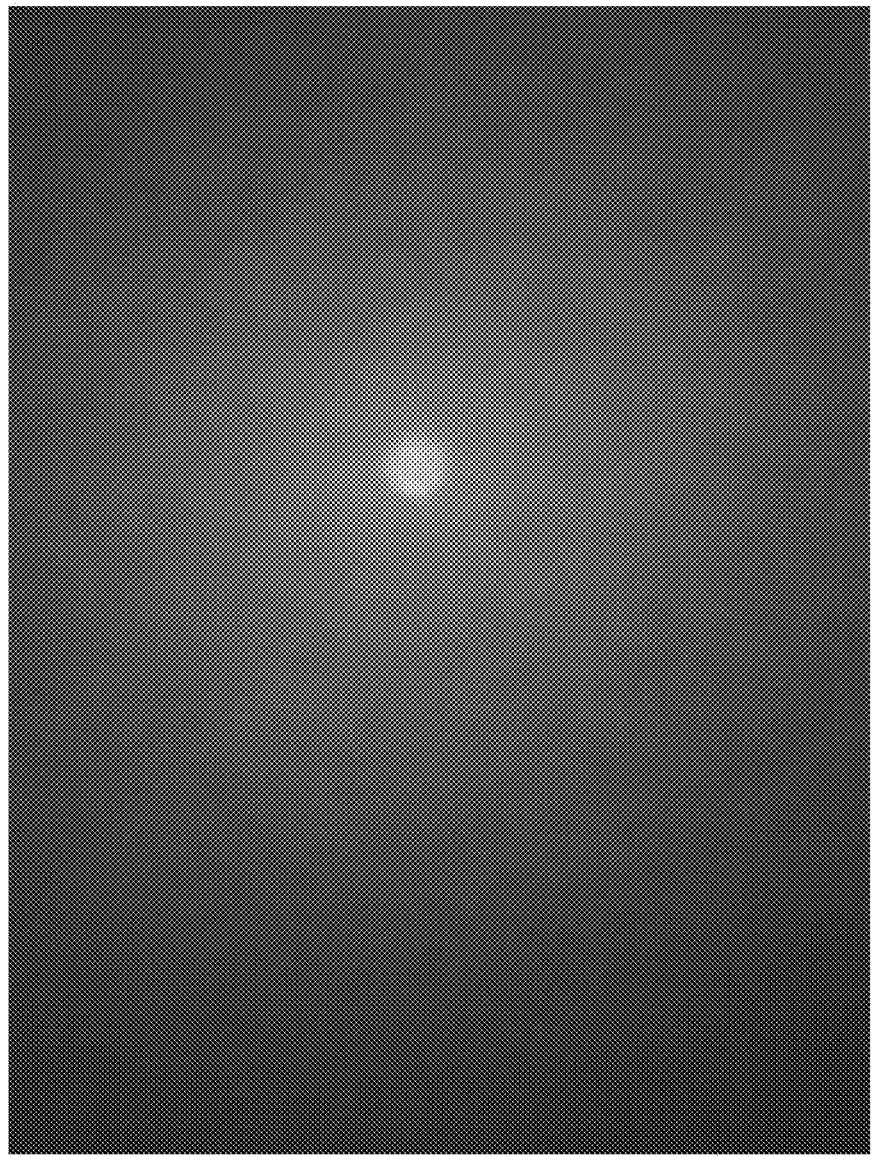
FIG. 5D is a front elevation view of another example of a sample extinction coefficient image.

The camera 118 may capture one or more images of the pigmented sample 102 as it is illuminated by the light source 116. In the extinction coefficient test fixture 120 the camera 118 may have a relative long focal length (e.g., 108 mm) so that the camera 118 may capture relatively narrow field-of-view images for each color of the light source 116. FIG. 5A is a front elevation view of a light extinction coefficient image 122 captured by the camera 118. FIG. 5B is a front elevation view of a sample extinction coefficient image 124 captured by the camera 118. As shown in FIG. 5A, in some embodiments the light extinction coefficient image 122 may be an image of the light source 116 without the pigmented sample 102 positioned therebetween. The light extinction coefficient image 122 may be used, as discussed in more detail below, in order to estimate an intensity of the light source 116. In some embodiments, the intensity for each color of the light source 116 may remain substantially the same, and so the light extinction coefficient image 122 may be captured only once although multiple light colors may be used. However, in other embodiments, the intensity for each color light source 122 may vary, and thus the light extinction coefficient image 122 may be captured for each color of the light source 116.

After the light extinction coefficient image 122 is captured, the pigmented sample 102 may be positioned within the extinction coefficient test fixture 120 and the sample extinction coefficient image 124 may be captured.

In some embodiments, the two extinction coefficient images 122, 124 may be high dynamic range (HDR) images. In these embodiments, the images 122, 124 may better represent the range of intensity of the pigmented sample 102, which may allow for a better determination of the light scattering and directionality of light emitted by the light source 116 through the pigmented sample 102. However, it should be noted that in other embodiments, the images 122, 124 may be formed from a single exposure or fewer exposures. Similarly, although the images 122, 124 have been discussed as being HDR images, in some embodiments, the image 122, 124 may be non-HDR images.

In examples where the images used to measure the extinction coefficient 122, 124 are HDR images, the camera 118 may capture a plurality of multi-bit (e.g., 12 bit) exposures, with the number of exposures and the bit-number depend on the dynamic range of the scene. The plurality of exposures may then be combined together to form the light extinction coefficient image 122 and the sample extinction coefficient image 124. For example, for each the light extinction coefficient image 122 and the sample extinction coefficient image 124, there may be four separate exposures taken by the camera 118 which are combined to form each image 122, 124. In this example, a first exposure may be set at a darkest exposure, a second exposure may be set at a dark exposure, a third exposure may be a bright exposure, and a fourth exposure may be a brightest exposure.

It should be noted that prior to the images 122, 124 being captured, the light source 116 may be turned on and given a chance to "warm up," so that the intensity and/or color may be consistent throughout the light extinction coefficient image 122 and the sample extinction coefficient image 124. Similarly, in some embodiments, the camera 118 may be calibrated prior to capturing the images 122, 124. For example, the camera 118 may be geometrically and/or photometrically calibrated prior to the images 122, 124 being captured.

Figure 6:
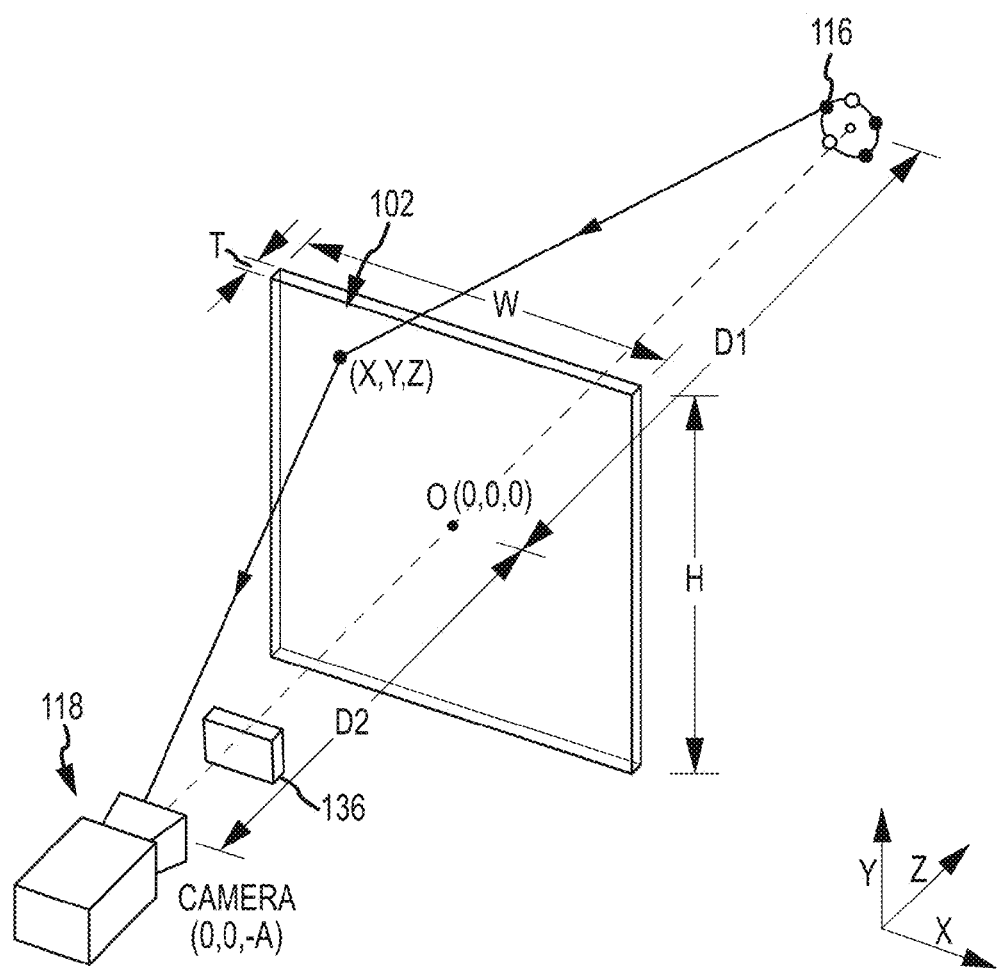
FIG. 6 is a perspective view of a forward scattering test fixture.

In addition to the extinction coefficient measurement 120, a forward scattering test fixture 130 may be arranged. FIG. 6 is a perspective view of the forward scattering test fixture 130. The forward scattering measurement 130 may be configured to capture images that may be analyzed to determine a forward scattering parameter of the pigmented sample 102. In the forward scattering test fixture 130, the light source 116 may be positioned substantially perpendicularly to the pigmented sample 102 at a distance D1 from the rear side of the pigmented sample 102. In some examples, the distance D1 may range between 100 mm to 150 mm, and in one example, the distance D1 may be approximately 123 mm.

Additionally, in the forward scattering test fixture 130, the camera 118 may be positioned on an opposite of the pigmented sample 102 at a distance D2 from the pigmented sample 102. In one example, the distance D2 may be determined from the non-parallax (i.e., center of the lens) point of the camera 118 and be approximately 276 mm. Also, the camera 118 may also have a reduced focal length (e.g., 18 mm) as compared with the extinction coefficient fixture 120. This is because the forward scattering test fixture 130 may be configured so that the camera 118 may capture one or more wide field-of-view images. For example, the larger field-of-view of the camera 118 may capture images that better capture a larger variety of visible incident and outgoing light directions of the pigmented sample 102.

As shown in FIG. 6, the camera 118 may be aligned directly with the light source 116. Accordingly, in some instances, a blocker 136 may be positioned between camera 118 and the pigmented sample 102. The blocker 136 may substantially prevent lens flare artifacts in images captured while the pigmented sample 102 is in the forward scattering test fixture 130. Without the blocker 136 lens flare artifacts may appear as the light source 116 is aligned with the camera 118. In other words, the blocker 136 may mask the light source 116 from the field of view of a lens of the camera 118.

Figure 7:
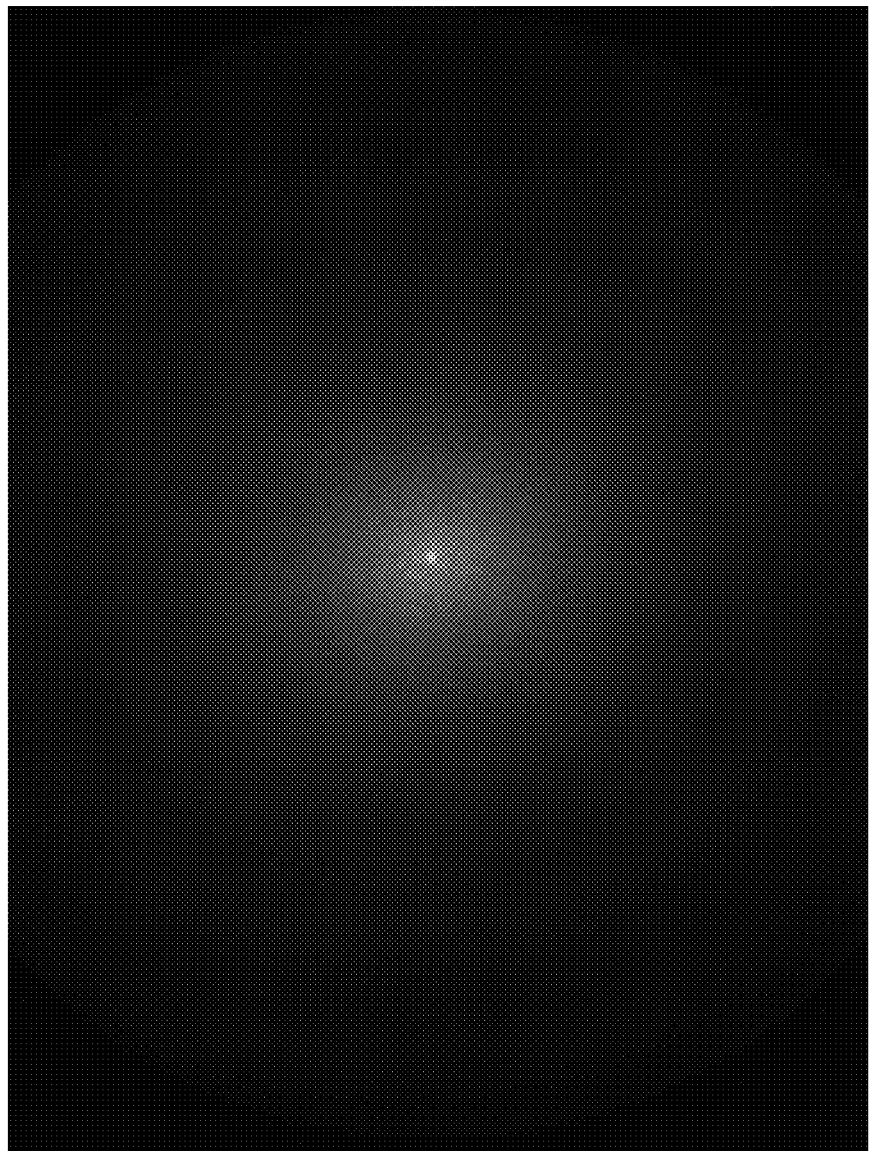
FIG. 7 is a front elevation view of a forward scattering image captured using the forward scattering test fixture of FIG. 6.

With the forward scattering test fixture 130, two additional images, a light forward scattering image 132 and a sample forward scattering image 134 may be captured by the camera 118. FIG. 7 is a front elevation view of the light forward scattering image 132, which may be similar to a sample forward scattering image 134. As described above with respect to the light extinction coefficient image 122 and the sample extinction coefficient image 124, the light and sample forward scattering images 132, 134 may be HDR images created by combining a plurality of exposures together. Similarly, the light forward scattering image 132 may be captured without the pigmented sample 102 positioned between the camera 118 and the light source 116 and the sample forward scattering image 134 may be captured with the pigmented sample 102 positioned therebetween. Furthermore, a light and sample forward scattering image 132, 134 may be captured for each pigment color and/or particle 106 concentration.

Figure 8:
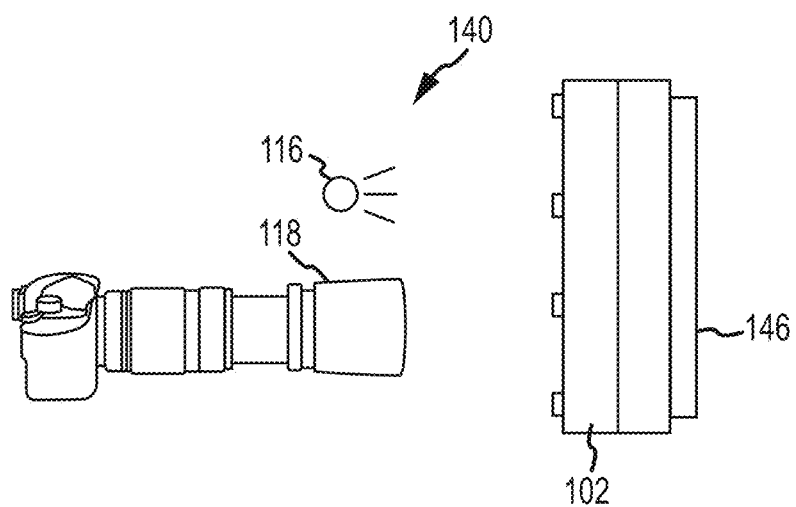
FIG. 8 is a side elevation view of a back scattering test fixture.

After the light and sample forward scattering images 132, 134 have been captured, a back scattering fixture may be arranged to capture additional images that may be analyzed to determine a back scattering of the target material sample. FIG. 8 is a side elevation view of the back scattering test fixture 140. In the back scattering test fixture 140, the light source 116 may be positioned on the same side of the pigmented sample 102 as the camera 118. Additionally, a reflection blocker 146 may be positioned on the rear side of the pigmented sample 102 opposite of the light source 116 and camera 118. The reflection blocker 146 may be paint, plastic, fabric, or another material capable of preventing light from being transmitted therethrough. In one embodiment, the reflection blocker 146 may be black automobile paint. The reflection blocker 146 may prevent additional light reaching the pigmented sample 102 due to light reflections off an interface between the plates 114A, 114B or air on the backside of the pigmented sample 102.

Figure 9:
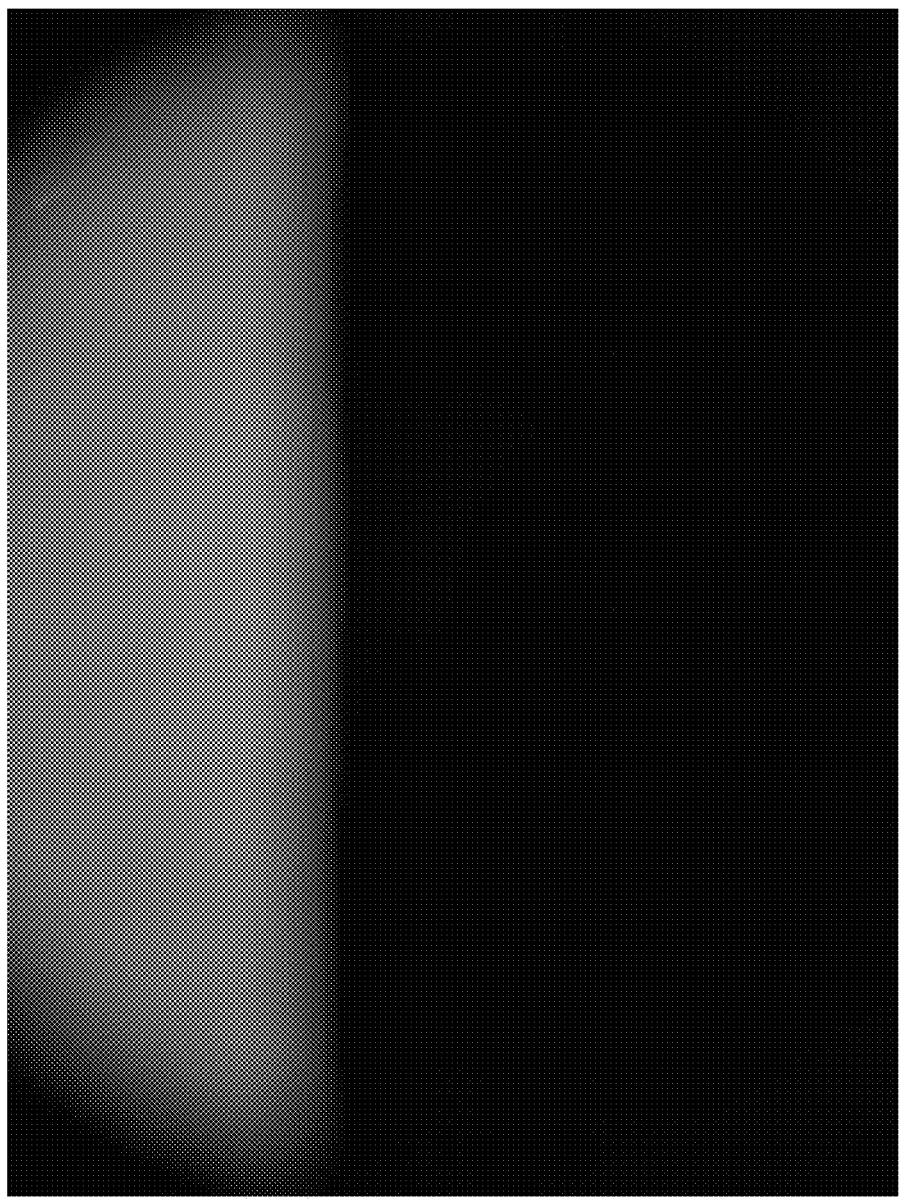
FIG. 9 is a front elevation view of a light back scattering image captured using the back scattering test fixture of FIG. 8.

With the back scattering test fixture 140, a light back scattering image 142 and a sample back scattering image 144 may be captured by the camera 118. FIG. 9 is a front elevation view of the light back scattering image 142, which may be similar to the sample back scattering image 144 (depending on the material). The back scattering images 142, 144 may be substantially the same as the other images, i.e., they may be HDR images created from multiple exposures, with the light back scattering image 142 taken prior to the pigmented sample 102 being in position and the sample back scattering image 144 taken with the target material sample 144 positioned in front of the light source 116 and camera 118.

In some instances, in the back scattering test fixture 140, the intensity of the light source 116 may need to be determined again as the geometry with respect to the light source 116 and the camera 118 may have been altered as compared with the previous test fixtures 120, 130. In some examples, the light back scattering image 142 may be captured with a color checker having a known reflectance positioned in replace of the pigmented sample 102. For example, a color checker such as the grayscale COLORCHECKER by X-RITE may be illuminated by the light source 106 and the light back scattering image 142 may be captured. The light back scattering image 142 may then be used to extract the intensity of the light source 106 as the reflectance of the color checker may be known. The light back scattering image 142 and the sample back scattering image 144 may be used to determine the back scattering of the pigmented sample 102, which will be discussed in more detail below.

Figure 10:
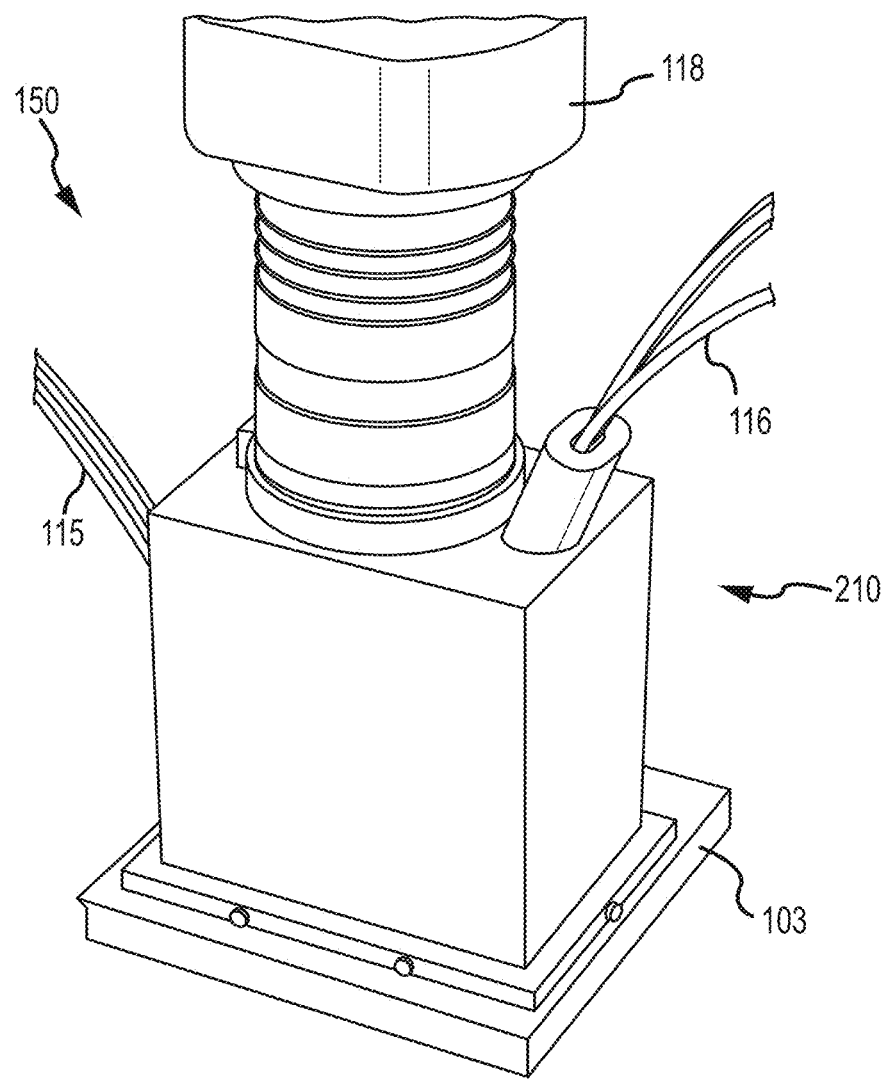
FIG. 10 is a perspective view of a first example of a diffuse reflectance and bulk scattering measurement device.

Once the light back scattering image 142 and the sample back scattering image 144 have been captured, a diffuse reflectance fixture may be setup. FIG. 10 is a perspective view of the diffuse reflectance test fixture 150. The diffuse reflectance test fixture 150 may be configured to measure the diffuse reflectance of the pigmented sample 102. In the low-scattering regime (i.e., with a thin target material sample), some parameters may have identical measurements and thus may be omitted (see, the second example discussed below). However, in the bulk-scattering measurements in thicker samples, these parameters may be different. Accordingly, in some examples in order to disambiguate between different parameters of the target material sample, in the diffuse reflectance test fixture 150 the pigmented sample 102 may be replaced with a thicker pigmented sample 102. Further, measurements taken of the pigmented sample 102 may also be used to validate or correct measurements taken using the images 122, 124, 132, 134, 142, 144 in the extinction coefficient test fixture 120, the forward scattering test fixture 130, and the back scattering test fixture 140. This is because, the first, second, and third test fixtures 120, 130, 140 are configured to provide images that allow a determination of the low-order scattering parameters of the pigmented sample 102. However, the low order scattering parameters may be different from the bulk scattering properties of a thicker sample. Thus, the diffuse reflectance test fixture 150 may assist to correct and/or validate the values determined suing the other setups.

The thick pigmented sample 102 may have the same color pigment and the same concentration of pigment particles 106 as the pigmented sample 102. In some examples, when the first pigmented sample 102 is created, the thick pigmented sample 102 may be created with the same mixture of base material 104 and pigment particles 106. By creating the two pigmented samples 102, 103 at the same time the two pigmented samples 102, 103 may be substantially the same, except that the thick pigmented sample 102 may have an increased thickness T as compared with the pigmented sample 102.

With reference to FIG. 10, in the diffuse reflectance test fixture 150, the camera 118 may be positioned directly above and/or on top of the thick pigmented sample 102. The light source 116 for this test may include a plurality of fiber optic cables or other light guides optically connected to a light. In one example, the light source 116 may include five fiber optic cables. In some implementations, a diffuser, such as an opal glass diffuser, may be positioned at the terminal end of the light source 116. The diffuser may be used to regulate the angular intensity distribution of light on the pigmented sample 102.

The light source 116 may be located at a top right edge of the camera 118 and may be angled with respect to a top surface of the pigmented sample 102. In one example, the angle between the surface normal of the pigmented sample 102 and the light source 116 may be approximately 45 degrees. With briefly reference to FIG. 12B (which may include the diffuse reflectance test fixture), the light source 116 may be located at location C, which may be arranged at 45 degrees relative to the pigmented sample. As discussed in more detail below, the diffuse reflectance test fixture 150 may also be used to determine select parameters of a target material. Further, a spectral measurement device may integrate the diffuse reflectance test fixture 150 into a single device (see, e.g., FIGS. 12A and 12B).

Figure 11A:
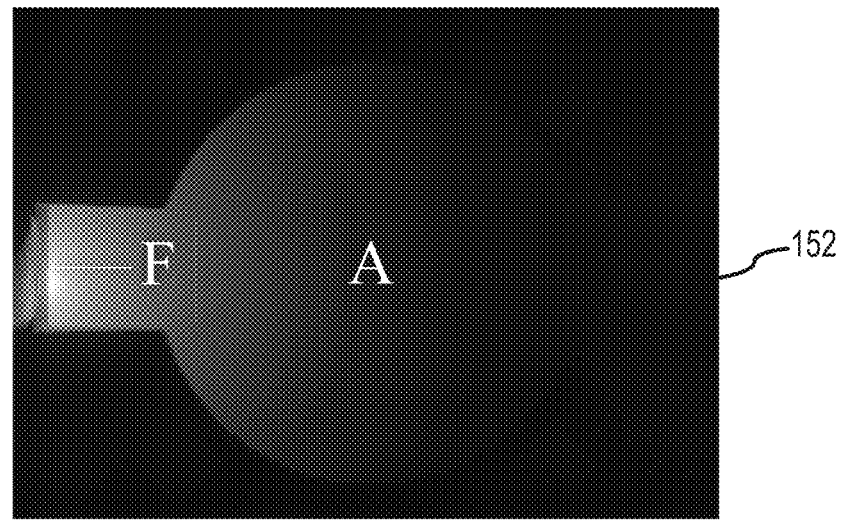
FIG. 11A is a front elevation view of a bulk scattering profile image captured using the measurement device of FIG. 12B of a pigmented sample.
Figure 11B:
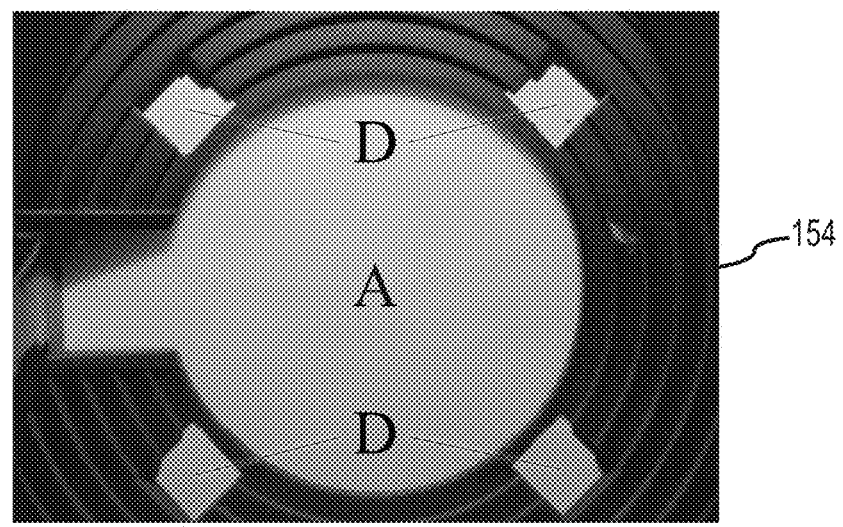
FIG. 11B is a front elevation view of a sample diffuse reflectance image captured using the measurement device of FIG. 12B of a pigmented sample.

As with the other test fixtures, the camera 118 in the diffuse reflectance setup 150 may images of the sample. FIG. 11A is a front elevation view of a light bulk scattering image 152. FIG. 11B is a front elevation view of a sample diffuse reflectance image 154. The two images 152, 154 may be substantially the same as the other images, in that they may each be HDR images created from a plurality of exposures of the camera 118. Also, as with other images, the two images 152, 154 may be created for various colors of the light source 116 and/or other pigment colors or concentrations. In one example, the bulk scattering image 152 may be captured by the camera 118 with a color checker positioned in the place of the pigmented sample 102. The diffuse reflectance image 154 may be captured with the color checker removed and the pigmented sample 102 in position (as shown in FIG. 10). As the light source 116 may include multiple different optical fibers, the diffuse reflectance of the pigmented sample 102 for different color channels (e.g., blue, red, and green) may be determined by taking a ratio of two small patches near or at a center of the sample diffuse reflectance image 154 and using the known reflectance of the color checker as captured in the bulk scattering image 152.

Testing the Pigmented Sample

Second Example

As briefly mentioned above, for certain pigmented samples the back scattering and/or forwarding scattering measurements may be similar to the diffusion measurement. Additionally, for certain pigmented samples, the appearance and optical properties can be approximated by diffusion theory. In these instances, the bulk scattering profile measurement and the diffuse reflectance measurement may be the only two measurements performed. Therefore, in some instances, the back scattering and/or forwarding scattering measurements may be omitted. In particular, in a second example, the pigmented spectral parameters of the pigmented sample 102 may be determined using a spectral capturing device. In this example, a bulk scattering measurement 145 and the diffuse reflectance measurement 150 may captured and used to analyze the parameters of the pigmented sample. By using a single device, both measurements may be done rapidly and may not require the pigmented sample to be positioned in various orientations, such as those required for the back scattering and the forward scattering images.

Figure 12A:
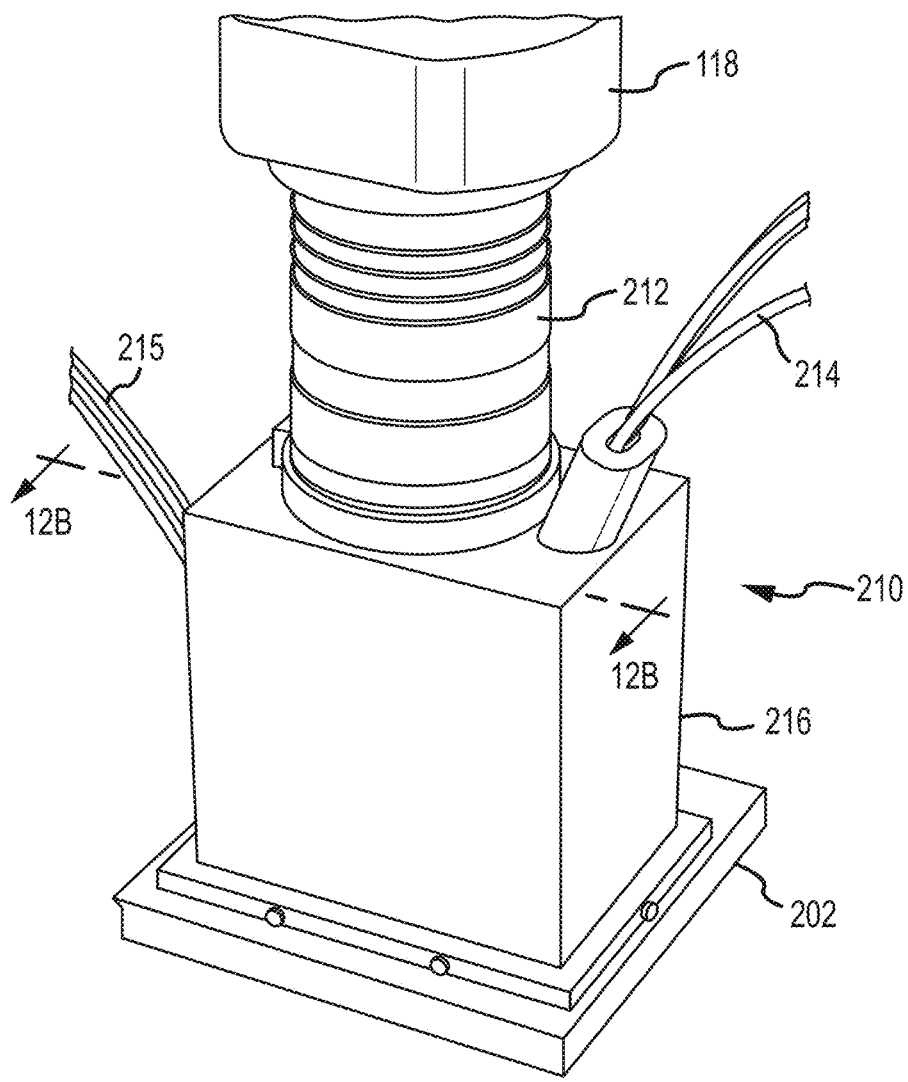
FIG. 12A is a perspective view of a second example of a spectral measurement device positioned on a target sample of target material.
Figure 12B:
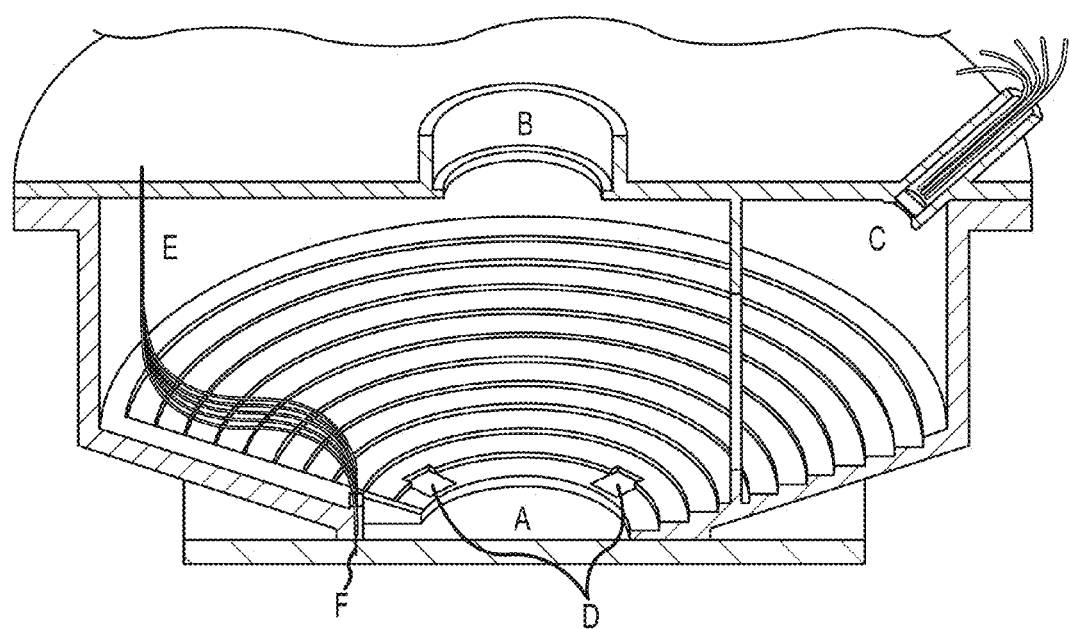
FIG. 12B is a cross-section view of a third example of a spectral measurement device taken along a line similar to 12B-12B in FIG. 12A, in this example the measurement device may perform both diffuse reflectance and bulk scattering measurements and may include one or more calibration elements.

In this example, a spectral testing device, such as the one illustrated in FIGS. 10, 12A, and 12B may be used to capture both sets of data (bulk scattering and diffusion). As will be discussed in more detail below, the measurement device 210 may be used to measure both the pigmented samples 103, as well as the target materials. In this second example, the measurement device 210 performs two measurements, one to determine the diffuse reflectance, $\bar{\rho}^\lambda$ and the other one to measure the bulk scattering profile, $\overline{R}_d^\lambda$. The method steps to determine the scattering parameters for the pigmented sample using this second example, and in particular determining the diffuse reflectance and bulk scattering profile, will be discussed with respect to FIG. 14B.

The diffuse reflectance setup 150 illustrated in FIG. 10 may be used to capture the diffuse reflectance image 154, such as shown in FIG. 11B. This measurement and setup may be substantially the same as discussed above and as shown in the diffuse reflectance image. In this example, to capture the diffuse reflectance images, the pigmented sample 102 is brought into contact with the measurement device 150 for a predetermined period of time. The time period may be a few seconds or up to a few minutes, depending on the darkness of the pigmented sample 102, e.g., the darker the pigmented sample the longer the time it may be illuminated and in contact with the measurement device. As the light source 116 is activated, an image for each light wavelength (in this case, five wavelengths), is captured. In other words, the camera 118 may capture measurements for each wavelength in the light source 116. As one example, measurements may be done for five distinct wavelength-bands (indexed by λ) using five LEDs incorporated into the light source 116. The images are the same as the diffuse reflectance images 152, 154 illustrated in FIGS. 11A and 11B and may be captured with the light source 116 positioned at an angle relative to the pigmented sample.

Once the images are captured, the images may be processed to create HDR images. As an example, the unclipped pixels for each image may be summed and then divided by the total exposure time. This process may apply low weights to those images with low exposure times, which is helpful in many instances because often low exposure photographs can be prone to noise.

In this second example of testing the pigmented samples, the measurement device 210 may also be used to capture the bulk scattering profile of the pigmented sample. With reference to FIGS. 12A and 12B, the measurement device 210 may be used with the pigmented sample 102 positioned within the field of view of the camera 118. In this example, the light source 115, 215 positioned may be used to illuminate the pigmented sample 102. The light source 215, may be substantially the same as the light source 216 and 116 used in the diffuse reflectance measurement and may include a plurality of different wavelength LEDS. However, this light source 115, 215 may be in contact with an edge of the pigmented sample and may illuminate the pigmented sample from a location F (shown in FIG. 11A). This location F may not be directly visible by the camera 118, e.g., may be positioned outside of the field of view of the camera 118. As one example, the light source 215 may terminate between 0.1 to 0.3, and preferably 0.1 mm, from the edge of the measurable location of the pigmented sample by the camera 118. By positioning the light source 115, 215 at an edge of the pigmented sample 102 and outside the field of view of the camera 118, the camera may be better able to capture the light as it is transmitted through the pigmented sample 102, rather than light that may not be transmitted through the pigmented sample 102 but captured directly from the light source itself.

To capture the images for the bulk scattering measurement, light from the light source 116 illuminates the pigmented sample 102 from location F and propagates through the pigmented sample 102 into the field of view of the camera. An example of this bulk scattering image 152 is shown in FIG. 11A. The image 152 illustrated in FIG. 11A is an example greyscale HDR captured with one LED of the light source 116 activated. In some implementations, the bulk scattering measurement may include capturing multiple images of the pigmented sample, as the sample is illuminated by the separate wavelength LEDs. As one example, five images, such HDR images, may be captured. Each of the five images illustrates the bulk scattering for the pigmented sample for each separate wavelength included with the light source 115, 215.

Determining Pigmented Sample Scattering Parameters

Using Data Collected During Tests from First Example

Using the images taken in the extinction coefficient test fixture 120, the forward scattering test fixture 130, the back scattering test fixture 140, and/or the diffuse reflectance test fixture 150 a variety of scattering parameters of the pigmented sample 102 may be determined. In some instances, these scattering parameters may correspond to the scattering parameters for the pigment particles 106 and the base material 104. It should be noted that generally the target material sample 106 may be molded as a volume having subsurface scattering effects in addition to diffuse reflection. This modeling approach allows for more accurate modeling of translucent materials which may have significant subsurface scattering (as explained in more detail below). Further, by determining the scattering parameters for the pigment particles 106 and the base material 104 separately, the scattering parameters for different thicknesses and pigment particle concentrations may be estimated.

In some examples, the parameters which may be determined by the images 122, 124, 132, 134, 142, 144, 152, 155 may be the scattering coefficient $\sigma_s$, the extinction coefficient $\sigma_t$, the absorption coefficient $\sigma_a$, scattering albedo, and the phase function.

The extinction coefficient $\sigma_t$ may be represented in terms of the scattering coefficient $\sigma_s$ and the absorption coefficient $\sigma_a$, as shown in Eq. (1) below.

$$\sigma_t = \sigma_s + \sigma_a \qquad \text{Eq. (1)}$$

As shown in Eq. (1), the extinction coefficient or total attenuation coefficient $\sigma_t$ may be the sum of the scattering coefficient $\sigma_s$ and the absorption coefficient $\sigma_a$. In other words, the extinction or total coefficient is the combination of all the light that may either be absorbed by the pigmented sample 102 or may be scattered by the pigmented sample 102. Initially, for the pigmented sample 102, the extinction coefficient may be estimated first, and then the other parameters may be determined and the extinction coefficient may be re-evaluated.

With reference to FIGS. 5A and 5B, the extinction coefficient images 122, 124 may be evaluated to determine an extinction coefficient of the pigmented sample 102. The light extinction coefficient image 122 may have no scattering, as there is no material positioned between the light source 116 and the camera 118. However, the sample extinction coefficient image 124 may have some scattering, in addition to absorption and normal incidence. Using Eq. (2) below, an attenuation-only (e.g., absorption-only) image $I_A$ is represented as the result of the sample extinction coefficient image 124 ($I_{sa}$) with the average scattering intently $\bar{s}$ removed.

$$I_A = I_{sa} - \bar{s} \qquad \text{Eq. (2)}$$

In Eq. (2) above, $I_A$ may represent an image of the pigmented sample 102 illuminated by the light source 116 with scattering removed. In other words, $I_A$ represents an attenuation-only image of the pigmented sample 102 illuminated by the light source 116. In some instances, in the sample extinction coefficient image 124, pixels directly surrounding the light source 116 may provide a local estimate of scattering of the pigmented sample 102. Thus, as shown in Eq. (2), by removing the average intensity $\bar{s}$ of pixels directly surrounding the light source 116 and the sample extinction coefficient image 124 ($I_{sa}$), an attenuation-only image $I_A$ may be determined. In other words, the average scattering $\bar{s}$ may be globally subtracted from the sample extinction coefficient image 124 to produce the approximately attenuation-only image $I_A$ as shown in Eq. (2).

To determine the extinction coefficient, the two extinction coefficient images 122, 124 may be evaluated, and assuming absorption-only and normal incidence, a pixel intensity may be expressed by Eq. (3) below. Scattering of light through the pigmented sample 102 is reduced due to the low concentration of pigment particles 106 as well as the reduced thickness of the pigmented sample 102. Thus, in Eq. (3), there is an assumption that the light through the pigmented sample 102 is absorbed and reflected normally (that is, without directionality). It should be noted that in actuality, the sample extinction coefficient image 124 may have a small amount of scattering in addition to absorption. However, this scattering $\bar{s}$ is estimated and removed using Eq. (2) prior to using Eq. (3).

$$L_{out} = L_{in} e^{-\sigma_t D} \qquad \text{Eq. (3)}$$

In Eq. (3), Lout is the observed outgoing radiance (i.e., the sample extinction coefficient image 124), Lin is the incidence illumination (i.e., the light extinction coefficient image 122), D is the thickness T of the pigmented sample 102, and $\sigma_t$ is the extinction coefficient. Expressing Eq. (3) using the light extinction coefficient image 122 and the sample extinction coefficient image 124, as well as globally subtracting the average scattering $\bar{s}$ of the sample extinction coefficient image 124, the extinction coefficient $\sigma_t$ can be represented by Eq. (4) below, where $I_L$ is the light extinction coefficient image 122 and $I_A$ is the attenuation only image as provided in Eq. (2) (and related to the sample extinction coefficient image 124).

$$\sigma_t = \frac{\log I_L - \log I_A}{D} \quad \text{Eq. (4)}$$

Thus, using a ratio of light extinction coefficient image 122 and the sample extinction coefficient image 124, an estimation of the extinction coefficient $\sigma_t$ of the pigmented sample 102 may be determined.

Using the estimated extinction coefficient $\sigma_t$, the other parameters of the pigmented sample 102 may be determined. Furthermore, with the determination of the other parameters, the initial estimate of the extinction coefficient $\sigma_t$ may be refined. To determine the phase function of the pigmented sample 102, a three-parameter multi-lobed Henyey-Greenstein function, reproduced below as Eq. (5), may be used. The three-parameter multi-lobe Henyey-Greenstein function may be a linear blend of two Henyey-Greenstein functions.

$$HG_{ml}(g_1, g_2, w_2) = (1-w_2)HG(g_1) + w_2 HG(g_2) \quad \text{Eq. (5)}$$

Although Eq. (5) is a multi-lobe phase function, the additional lobe(s) as compared with a single lobe Henyey-Greenstein function, is more expressive in order to better match the images captured in the various test fixtures 120, 130, 140, 150. For example, in order to match the shape of the forward scattering measurement determined in the forward scattering fixture 130 a highly forward lobe is required. However, with a highly forward lobe, matching a diffuse reflectance measurement as determined in the diffuse reflectance test fixture 150 may result in a non-physically realizable value for single scattering albedo.

With reference to Eq. (5), g1 and g2 are the mean cosine angles underlying the Henyey-Greenstein function. Further, values for g1 and g2 may range from −1 representing pure backscattering to 1 representing pure forward scattering. The ratio between the mean cosine angles g1 and g2 is defined by w2 which ranges between 0 and 1.

To estimate the scattering parameters and the phase function of the pigmented sample 102, the forward scattering images 132, 134 and the back scattering images 142, 144 may be used. These images 132, 134, 142, 144, as described in more detail above, may be captured by the camera 118 with a lens positioned in a wide field-of-view. In other words, the camera 118 may be positioned farther from the pigmented sample 102 than in the extinction coefficient test fixture 120. Data from each of the test fixtures 120, 130, 140, 150 are used as input values to Eq. (5) and with an error equation Eq. (6) (below) an imitative optimization process may be used to determine the scattering parameters, phase, as well as to correct the initial extinction coefficient as determined above in Eq. (4).

$$F(x,y) = I(x,y) - N(x,y) \quad \text{Eq. (6)}$$

An example error equation that may be used to determine the scattering parameters and phase function is presented above as Eq. (6). In Eq. (6), the error at each pixel within each image is expressed as the difference between the captured pixel irradiance I and the irradiance predicated by the numerical estimate N.

The mean-squared error across a particular image may be minimized using Eq. (7) below.

$$\min_{g_1, w_2, g_2} \sum_y \sum_x F(x, y)^2 \quad \text{Eq. (7)}$$

Eq. (7) above may be implemented using a simplex-based function that may be tolerant to noise. For example, using MATLAB the function "fminsearch" may be used to implement Eq. (7). In this example, the "fminsearch" function finds a minimum of a scalar function of several variables, starting with an initial estimate. However, in other examples, other processes for unconstrained nonlinear optimization may also be used in order to determine the variables of Eq. (5).

In some examples, in order to reduce the computation that may required per itineration, the images from the test fixtures 120, 130, 140, 150 may be assumed to be isotropic or symmetric and accordingly with Eq. (5) only a horizontal scan line may be assumed. Using this assumption and Eq. (6) and Eq. (7), the mean-square different between two 1D vectors may be minimized.

The diffuse reflectance image 154 may provide data related to the diffuse reflectance of the pigmented sample 102, and particularly of the thick pigmented sample 102. Flock's model (see Eq. (12)) may predict the diffuse reflectance of a highly scattering infinitely thick sample, given the reduced albedo and index of refraction. Thus, with the diffuse reflectance images 152, 154, the diffuse reflectance may be known and using Flock's model the reduced albedo may be fixed in the optimization process using Eq. (5) above.

As the diffuse reflectance, albedo, and current phase function may be determined, these parameters may provide an estimate of the single scattering albedo. Furthermore, with the additional measurements, a substantial number of scattering parameters may be constrained during the optimization process. However, there may be three parameters that may not be constrained. These additional parameters may be determined using the optimization function of Eqs. (6) and (7), see the discussion of Eqs. (8)-(21) below.

Figure 14A:
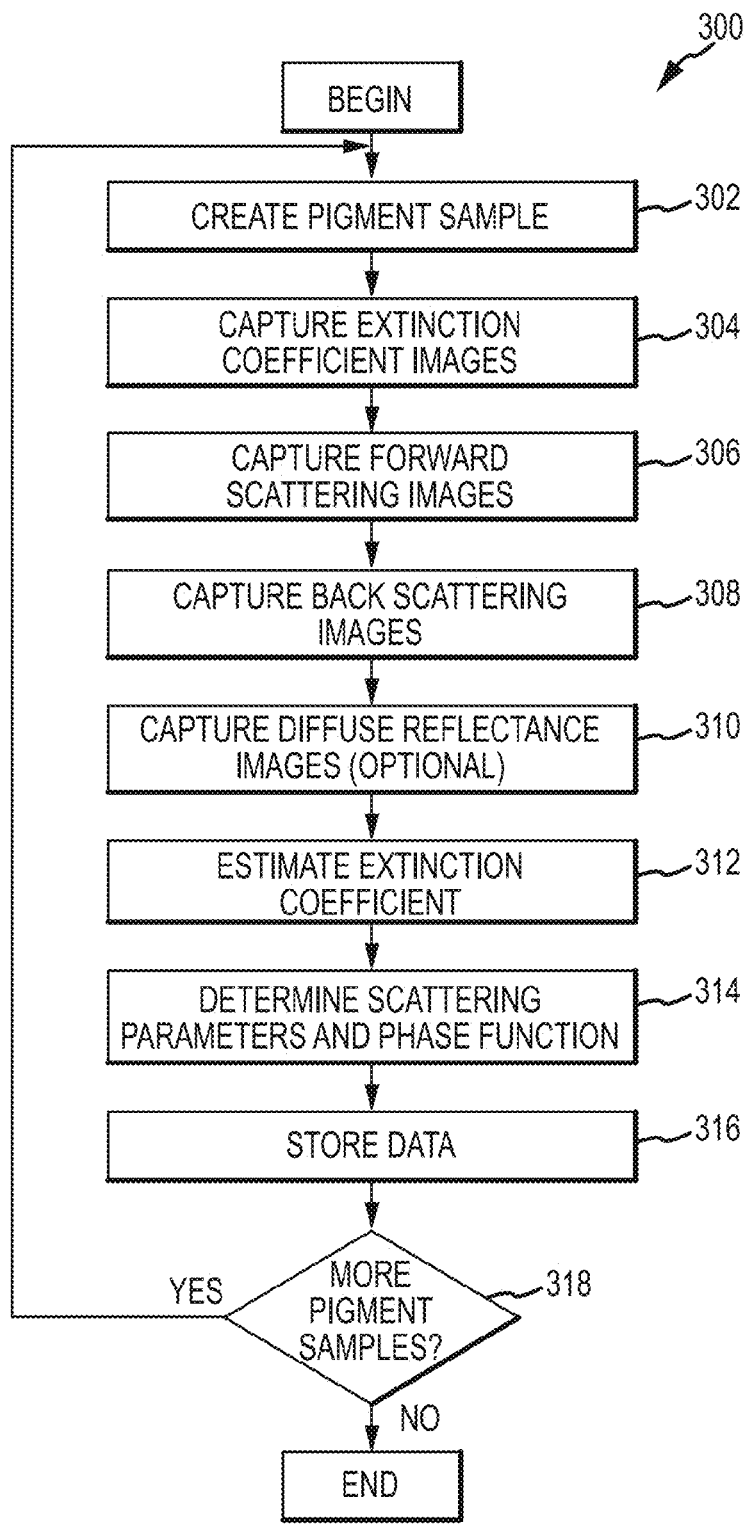
FIG. 14A is a flow chart illustrating a method for determining parameters corresponding to pigment particles of the target material sample corresponding to FIG. 1B.

A method for determining the scattering parameters for the pigment particles 106 and base material 104 within the pigmented sample 102 will now be discussed. FIG. 14A is a flow chart illustrating a method 300 for analyzing target material samples 102. The method 300 may begin with operation 302 and the pigmented sample 102 may be created. As discussed above with respect to FIGS. 2-3B, the pigment particles 106 may be mixed with the base materials 104, and the target material sample 106 may then be positioned within a securing device 108. As noted above, the pigment color and/or concentration within the base material 104 may be varied depending on the desired data to be collected.

Once the pigmented sample 102 has been created, the method 300 may proceed to operation 304 and the extinction coefficient images 122, 124 may be captured. For example, the extinction coefficient test fixture 120 may be arranged so that the camera 118 may capture the light extinction coefficient image 122 and the sample extinction coefficient image 124. As discussed above, in some instances, the camera 118 may capture one or more exposures which may be used to create the images 122, 124 (e.g., the images may be HDR images) or the camera 118 may directly capture the images 122, 124. In some examples, the camera 118 may capture one more exposures and a computing device may create the HDR images corresponding to the extinction coefficient images 122, 124.

The method 300 may then proceed to operation 306 and the forward scattering images 132, 134 may be captured. As with the extinction coefficient images 122, 124, in this operation 306 the forward scattering test fixture 130 may be arranged and the camera 118 may capture the light forward scattering image 132 and the sample forward scattering image 134.

Once the forward scattering images 132, 134 have been captured, the method 300 may proceed to operation 308 and the back scattering images 142, 144 may be captured. In operation 308, the back scattering measurement 140 may be arranged and the camera 118 may capture the light back scattering image 142 and the sample forward scattering image 144.

With continued reference to FIG. 14A, the method 300 may proceed to optional operation 310. In operation 310 the diffuse reflectance test fixture 150 may be arranged and the diffuse reflectance image 154 may be captured. Alternatively, the spectral measurement device 210 (described in more detail below) may be used to capture the diffuse reflectance image 154.

Operation 310 may be optional as the image captured in operations 304, 306, and 308 may provide enough data to determine scattering parameters of the pigmented sample 102. However, in some instances, during the optimization process in determining the scattering parameters using Eq. (1)-(7), there may various forward and back scattering values may be result in identical in low-order scattering regimes (e.g., thin samples), but the forward and back scattering values may be very different in the bulk-scattering parameters of thicker samples. Accordingly, depending on the desired replication material size (based on the target sample), operation 310 may be performed in order to determine a diffuse reflectance for the pigmented sample 102 to more accurately determine the spectral material parameters. The diffuse reflectance image 154 may be taken of the thick pigmented sample 102, which may provide an additional constraint to the optimization process utilizing Eq. (1)-(7) which will allow for a more efficient process.

Figure 17:
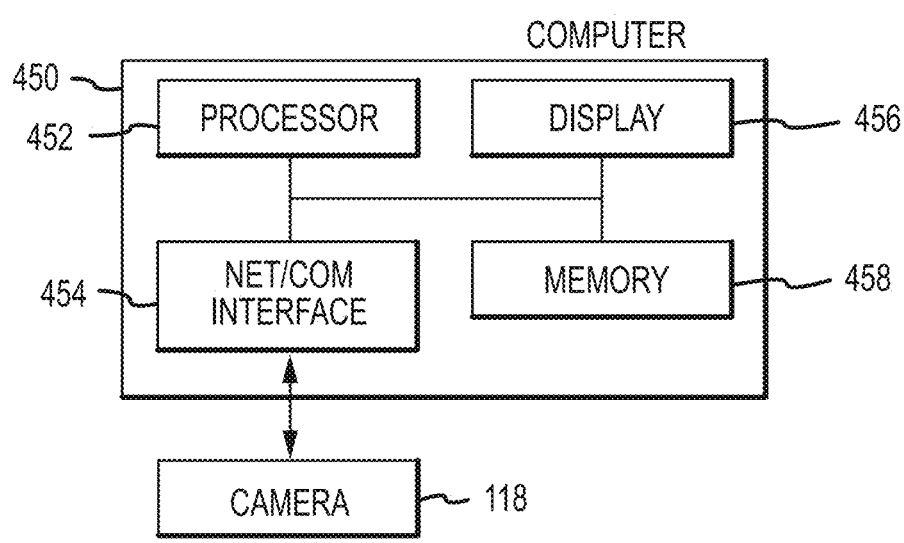
FIG. 17 is a block diagram of a computing device in communication with the camera.

After operation 308 or operation 310, the method 300 may proceed to operation 312 and the extinction coefficient may be estimated. In some examples, a computing device may analyze the images to determine the extinction coefficient. FIG. 17 is a block diagram of an exemplary computing device 450 in communication with the camera 118. In some examples, the camera 118 may communicate with the computing device 450 to transfer data, such as data corresponding to the various images 122, 124, 132, 134, 142, 144, 152, 154 to the computing device 450. The computing device 450 may be substantially any type of electronic device capable of receiving and processing instructions. For example, the computing device 450 may be a desktop computer, laptop computer, network of computers, smart phone, tablet computer, and the like.

The computer 450 may include a processor 452, a network/communication interface 454, memory 458, and/or a display 456. The processor 452 may receive and execute instructions to operate the computing device 450. In some examples the processor 452 may be a processor, microprocessor, microcomputer and the like.

The network/communication interface 454 may transfer data to and from the computing device 450 from an external device and/or network. For example, the network/communication interface 454 may receive data from the camera 118 via an input port or via a network communication (e.g., Ethernet, WiFi, radio signals, etc.).

The memory 458 may be in communication with the processor and may store electronic data that may be utilized by the computer or other electronic devices. For example, the memory 458 may store data corresponding to the images and/or the scattering parameters for particular pigment colors (discussed in more detail below). The memory 458 may be, for example, non-volatile storage, a magnetic storage medium, optical storage medium, magneto-optical storage medium, read only memory, random access memory, erasable programmable memory, or flash memory.

The computing device 450 may also include or be in communication with a display 456. The display 456 may display data, images, and the like to the user. For example, the display 456 may be a liquid crystal display, plasma display, light emitting diode screen, or the like.

With continued reference to FIG. 14A, in operation 310 the computing device 450 may analyze the extinction coefficient images 122, 124 and with Eq. (1)-(4) may determine an estimate of the extinction coefficient. For example, the processor 452 may execute Eq. (4) to analyze the light extinction coefficient image 122 and the sample extinction coefficient image 124 in order to determine the extinction coefficient.

Using the estimated extinction coefficient determined in operation 312, the method 300 may proceed to operation 314 and the other parameters and/or phase function may be determined. In some examples, the computer or processor may use the images 122, 124, 132, 134, 142, 144, 152, 154 and the extinction coefficient along with Eq. (5)-(7) to determine the other parameters. As discussed above, using Eq. (5)-(7) may involve an optimization process that may include iterative steps to find the set of values that may most closely satisfy Eq. (5) based on the input from the various measurements as captured by the images 122, 124, 132, 134, 142, 144, 152, 154. Also, in some instances, it should be noted that the extinction coefficient that was originally estimated in operation 312 may be reevaluated based on the determined parameters and phase in operation 314. For example, the extinction coefficient may be determined to be a different value after the other parameters are determined.

Once the parameters are determined in operation 314, the method 300 may proceed to operation 316 and the parameters may be stored in the memory 458. The parameters for the pigmented sample 102 may be stored in the memory 458 as correlating to the particular pigment particle color 106 and/or the concentration of the pigment particle 106, which may be determined when creating the pigmented sample 102. In this manner, a database or directory of the scattering parameters of particular pigment colors may be created. This database may also be expanded to include the scattering parameters (if they vary) for different concentrations of particular color pigments. For example, after the data for a particular color pigment participle is stored in operation 316, the method 300 may proceed to operation 318. In operation 318 a user may determine whether there are additional colors or concentrations of the pigment particles whose scattering parameters should be determined. If, in operation 318 there are more pigment colors or concentrations, the method 300 may return to operation 302 and the method 300 may be created. Alternatively, if in operation 318 there are no additional pigment colors or consecrations, the method 300 may end.

The database or other memory storage of the parameters for particular pigment colors may reduce and/or eliminate the need for the various test fixtures 120, 130, 1340, 150 to be repeated when a new target sample is desired to be replicated. Furthermore, the database may be used to predict the appearance of a material made from substantially any combination of pigment particles.

Using Data Collected During Tests from Second Example

In the second example of the method as shown in FIG. 1C, the pigmented sample may be subjected to a diffuse reflectance test and a bulk scattering profile test. Using the data or images from these two tests one or more optical parameters for the pigmented sample, and specifically, a pigment, may be determined. As discussed above with using data collected from the first example, with equation Eq. (1), if two of the variables are known, the other two can be completed. In particular, the extinction coefficient is represented by Eq. (2) and the albedo can be represent by Eq. (8) below.

$$\alpha = \sigma_s/\sigma_t \qquad \text{Eq. (8)}$$

In the pigmented samples 102, which may be highly scattering, the flow of light can be modeled with a diffusion equation, which leads to approximate analytical models that can describe translucent materials. In these instances the scattering coefficient can be replaced with the reduced scattering coefficient $\sigma_s'$, and the phase function can be treated as isotropic. As used herein, the reduced parameters $\sigma_s'$, $\sigma_t'$, and $\alpha'$ are used, but the customary primes have been omitted for ease of notation.

The bulk scattering profile measurement and the diffuse reflectance measurements are used to acquire the per-wavelength-band bulk scattering profile $\overline{R}_d^\lambda$ and the per-wavelength-band diffuse reflectance measurement $\overline{\sigma}_d^\lambda$, respectively, for a set of pigmented samples 102, where each pigmented sample has a known pigment concentration c. Then, the reduced albedo $\alpha^\lambda$ and extinction coefficient $\sigma_t^\lambda$ for each pigment 106 and the base material 104 can be estimated. Often, two assumptions may be used to assist in the calculations, these two assumptions are that the absorption coefficient $\sigma_a^\lambda$ will be much smaller than the extinction coefficient $\sigma_t^\lambda$ on a per-wavelength bases and that multiple anisotropic scattering the pigmented sample can be approximated using an approximately equivalent isotropic material with reduced scattering parameters.

Using the diffusion model represented by Eq. (9) below, the subsurface reflectance or bulk scattering profile for the pigmented samples may be represented using quantized diffusion. The diffusion model represented by Eq. (9) below returns an analytic reflectance profile between two surface points x and y of the pigmented sample.

$$\frac{dL_r^\lambda(x)}{d\Phi_i^\lambda(y)} = R_d^{QD}(\alpha^\lambda, \sigma_t^\lambda, d; r) \qquad \text{Eq. (9)}$$

In Eq. (9), the reflectance profile for the two surface points x and y is expressed as a function of their distance $r=\lambda x-y\lambda$, thickness d of the pigmented sample, the reduced albedo $\alpha$, and reduced extinction coefficient $\sigma_t$ per wavelength band $\lambda$. The diffusion equation of Eq. (9), also depends on $\eta$, which is the index of refraction for the base material 104. In examples where silicon is used, the silicone index of refraction value is 1.41. However, depending on the base material used, the index of refraction value will vary. In analyzing the data from the testing in this second example, the internal details of the diffusion model equation may not be required to determine the parameters for the sampled pigmented sample and $R_d$ can be treated as a black box. Using Eq. (9), the bulk scattering profile $\overline{R}_d^\lambda$ for a particular wavelength for the pigmented sample can be captured.

A diffusion reflectance model may also be used to determine the diffuse reflectance $\overline{\rho}^\lambda$ of the pigmented sample 102. In one example, a tabulation of diffuse reflectance values from brute force Monte Carlo simulations can be used provide a model for the diffuse reflectance. Eq. (10) below is an example of this type of tabulation.

$$\rho(\alpha, \sigma_t, d) = 2\pi \int_0^\infty \frac{R_d^{MC}(\alpha, \sigma_t, d; r)}{\pi} r\, dr. \qquad \text{Eq. (10)}$$

Using Eq. (10) above for the tabulation, the diffuse reflectance $\rho$ may be parameterized according the reduced albedo Land optical thickness ($\sigma_t d$, where d is the measured thickness of the sample), and then those values may be stored in a 2D lookup table for use and interpolation. Using Eq. (10) and depending on the base material used, an assumption that a multiple scattering process including internal reflectance, is isotropic and that the diffuse reflectance is the reflectance of incoming light inside the surface to outgoing light inside the surface.

In some instances, the diffuse reflectance may not be measured directly during the diffuse reflectance measurement 150. Rather, the reflected radiance, $\overline{L}_s^\lambda$ may be measured and used to derive the diffuse reflectance $\overline{\rho}^\lambda$. In particular, in instances where the base material 104 is homogeneous with a smooth Fresnel boundary and single scattering is negligible, Eq. (11) below can be used to express the observed radiance.

$$\overline{L}_s^\lambda(\vec{\omega}_o) = 2\pi \int_0^\infty \int_\Omega \overline{L}_i^\lambda(\vec{\omega}_i)(\vec{\omega}_i \cdot \vec{n}) \frac{S_d^\lambda(r, \vec{\omega}_i, \vec{\omega}_o)}{\pi} r\, d\vec{\omega}_i\, dr \qquad \text{Eq. (11)}$$

In Eq. (11) above, $\vec{\omega}_i$ and $\vec{\omega}_o$ are the incident and outgoing directions respectively, $\vec{n}$ is the surface normal, and $\overline{S}_d^\lambda(r, \vec{\omega}_i, \vec{\omega}_o) = F_t(\vec{\omega}_o) \overline{R}_d^\lambda(r) F_t(\vec{\omega}_i)$ is the bidirectional surface scattering reflectance distribution function (BSSRDF) with Fresnel reshaping.

Using the diffuse reflectance setup 150 illustrated in FIG. 10, the camera 118 captures an image of the pigmented sample 102 from directly above the pigmented sample, such that $\vec{\omega}_o = 0°$. Additionally, the light source 116 illuminated the sample from a single direction such that $\vec{\omega}_i$ is at 45° to normal incidence. This positioning helps to avoid direct specular reflection of the light. The per-wavelength-band radiance of the sample, $\overline{L}_s^\lambda(0°)$, may be determined by averaging an approximately 1 cm² patch centered at location A shown in FIGS. 11A and 11B. Assuming the incident direction is constant at contributing regions, the observed radiance of Eq. (11) can be reduced to Eq. (12) below.

$$\overline{L}_s^\lambda(0°) \approx \frac{I_i^\lambda}{t^2} \cos(45°) F_t(0°) F_t(45°) 2\pi \int_0^\infty \frac{\overline{R}_d^\lambda(r)}{\pi} r\, dr. \qquad \text{Eq. (12)}$$

In Eq. (12) above, $I_i^\lambda$ is the intensity of the light source, located at distance t. In some examples, a calibration may be used to estimate the intensity measurement, $\overline{L}_c^\lambda(0°)$, for a grey diffuse calibration target placed at location A. By assuming that the calibration target is Lambertian, Eq. (13) may be used.

$$I_i^\lambda = \frac{t^2 \overline{L}_c^\lambda(0°)}{\overline{\rho}_c^\lambda(0°, 45°)\cos(45°)} \qquad \text{Eq. (13)}$$

In Eq. (13), $\rho_c^\lambda(0°, 45°)$ is the reflectance of the diffuse calibration target. As discussed above with respect to the diffuse reflectance measurement of FIG. 10, to correct for fluctuations in the intensity of the light source 116, reflectance standard patches shown at D are used. These reflectance patches are generally visible the measurements. The intensity $I_i^\lambda$ of the light source can be scaled by the average radiance ratio of the reflectance patches in the measurement of the pigmented sample 102 measurement and the calibration target measurement.

By combining Eqs. (12) and (13) and rearranging terms Eq. (14) can be derived. Eq. (14) can be used as the model reflectance $\rho$, Eq. (10), Eq. (14) is provided below.

$$\overline{\rho}^\lambda = 2\pi \int_0^\infty \frac{\overline{R}_d^\lambda(r)}{\pi} r\, dr \approx \frac{\overline{\rho}_c^\lambda(0°, 45°)}{F_t(0°) F_t(45°)} \frac{\overline{L}_s^\lambda(0°)}{\overline{L}_c^\lambda(0°)} \qquad \text{Eq. (14)}$$

Using the data collected during the diffuse reflectance measurement and the bulk scattering measurement, measurements for select diffuse reflectance and bulk scattering profile values can be mapped to pigments 102 and pigment concentrations within the base material 104. This will allow a database of parameter values corresponding to various pigment colors and pigment concentrations to be created, which assists in determining a recipe to replicate the appearance of a target material. Specifically, once the pigment concentrations and colors are mapped to detected appearances, the process can be inverted to match the appearance of a target material to a pigment concentration and color.

In one implementation, the pigment concentrations $C_\rho$ for each pigment sampled ($\rho=1, \ldots, \eta_\rho$), are mapped to the observed characteristics diffuse reflectance $\rho^\lambda$ and bulk scattering profiled $R_d^\lambda$ for a number of different wavelengths $\lambda=1, \ldots, \eta_\lambda$. The number of wavelengths may be determined by the number of light colors used for the light sources 115, 116. The parameters for each pigment concentration, wavelength, and pigment color may be stored in a database, such as in one or more memory or electronic storage components. Using the database, the reverse process can be used to provide an initial point for the nonlinear optimization of pigment concentrations to determine a recipe for the target material.

In particular, given the diffuse reflectance measurement $\overline{\rho}^\lambda$ and the bulk scattering profile measurement $\overline{R}_d^\lambda$ for the pigmented sample, the parameters of the material, such as the reduced albedo and the extinction coefficient ($\alpha, \sigma_t$) can be estimated by fitting to Eq. (14), seeking a match in the (relative) diffusion profile and the (absolute) total reflectance as provided by Eq. (15) below.

$$(\alpha^\lambda, \sigma_t^\lambda) = \mathrm{argmin} F(R_d(\alpha, \sigma_t, d), \rho(\alpha, \sigma_t, d), \overline{R}_d^\lambda, \overline{\rho}^\lambda) F(R_d, \rho, R_d', \rho') = [E(R_d, R_d') + (\rho - \rho')^2] \qquad \text{Eq. (15)}$$

In Eq. (15) E is a profile difference measurement. In one example, the first operation may be to fit the forward of diffusion mode of Eq. (14) to the measured bulk scattering profile $\overline{R}_d^\lambda$ and diffuse reflectance $\overline{\rho}^\lambda$ of a single wavelength band for the pigmented sample 102. To find a starting point for the optimization, the diffuse reflectance lookup table or pigment database created using the methods 300 and 330 is used to find an albedo $\alpha$ where $\rho(\alpha, \sigma_t, d) = \overline{\rho}^\lambda$, initially assuming that the pigmented sample is semi-infinite and $d = \infty$.

To obtain an initial guess for the extinction coefficient $\sigma_t$, the processor may perform an asymptotic simplification of the quantized diffusion mode, valid for $r \gg 1/\sigma_t$ as expressed by Eq. (16) below:

$$R_d(\alpha, \sigma_t, d; r) \approx k\frac{e^{-r\sqrt{\sigma_a/D}}}{r} \qquad \text{Eq. (16)}$$

In Eq. (16), D is the diffusion coefficient and k is a constant. As shown in FIG. 15A, the asymptotic approximately provides that for a large enough r, a plot of log $(rR_d(r))$ against r may be a straight link with a slope of $-\sqrt{\sigma_a/D}$. By fitting a line to log $(r\overline{R}_d^\lambda)$, $\sqrt{\sigma_a/D}$ can be obtained that is used by the processor to determine the extinction coefficient $\sigma_t$ using the currently estimated value of the albedo $\alpha$.

The extinction coefficient $\sigma_t$ and albedo $\alpha$ estimations can then be repeated for additional iterations. In the following iterations, a semi-infinite sample may no longer be assumed. In other words, d may be selected to be a measured thickness of the pigmented sample. This process typically requires 3-5 iterations in order to converge.

As another example of an optimization process, a nonlinear optimization may be used. Using the estimated values of $\sigma_t$ and albedo $\alpha$ estimations using Eq. (16), the Levenberg-Marquardt algorithm is used to compute the minimum of Eq. (15). To determine the difference between the two scattering profiles, a metric such as Eq. (17) below may be used.

$$E(R_d, R_d') = \frac{1}{r_1 - r_0}\int_{r_0}^{r_1}\left[(R_d(r)/\mu)^{\frac{1}{3}} - (R_d'(r)/\mu')^{\frac{1}{3}}\right]^2 dr \qquad \text{Eq. (17)}$$

In Eq. (17), the profiles are divided by their mean values ($\mu$ and $\lambda$') to account for the unknown intensity of the light source 116 in the diffusion profile measurement 150. The interval $[r_0, r_1]$ is a range of distances over which the model is expected to fit well. This range may be determined by shrinking the interval until a line fits within a selected tolerance and can be manually overridden to avoid glitches in the measured profiles. The residual error of each pigmented sample captured in a database is reflected by Eq. (18) below.

$$z_m^\lambda = \min\left(\frac{\mu_d^\lambda}{d_m^\lambda - d_{75\%}^\lambda + \mu_d^\lambda}, 1\right) \qquad \text{Eq. (18)}$$

In Eq. (18), $d_m^\lambda$ is the residual (minimum value of Eq. (15)) in a wavelength band $\lambda$ for the $m^{th}$ sample, $d_{75\%}^\lambda$ is the $75^{th}$ percentile residual over the entire database for this particular wavelength band $\lambda$, and $\mu_d^\lambda$ is the median error for the wavelength band $\lambda$ over the entire database. This confidence equation Eq. (18) can be used as a weight in fitting pigment parameters.

In some instances, fitting a single profile produces material parameters that correspond to the observed appearance of the pigmented sample 102, but in some instances, because the model is approximate, the best-fit parameters may not be close to the true materials of the pigmented sample. For example, with anisotropically-scattering materials where the forward model is less accurate, the best-fit parameters for the pigmented sample may not be close to the actual parameters of the material. In these instances, larger collections of pigmented samples may be fit at once using a global process and then refined using a local process.

The global pigment parameter process may be used to linearly relate pigment parameters of each pigment concentration and color for the pigmented samples. In particular, the parameters of each pigment determined using Eqs. (17) and (18) may be used to describe the appearance of the respective pigmented sample; however, these pigment parameters may not be linearly related to the pigment concentration as suggested by radiative transport theory may predict, which can affect the recipe predication of a target material. To enhance the connection between pigment concentrations and parameters, the results of the independent fitting of parameters to pigments (Eqs. (17) and (18)) can be used as an initial input to a process that determines material parameters for each pigment that are globally consistent with all of the pigmented samples evaluated in the database, based on the radiative transport theory assumption of a linear relationship between pigment concentrations and the resulting optical parameters of the pigmented sample. This linear relationship can be expressed using a matrix containing the properties of all pigmented sampled in all wavelength bands expressed as Eq. (19) below.

$$\Sigma = \begin{bmatrix} \sigma_1 \\ \vdots \\ \sigma_{n_p} \end{bmatrix} \qquad \text{Eq. (19)}$$

In Eq. (19), $\sigma_p = [\sigma_{s,p}^1 \ \sigma_{t,p}^1 \ \ldots \ \sigma_{s,p}^{m_\lambda} \ \sigma_{t,p}^{m_\lambda}]$ represent the material parameters of the pigment and a matrix C may be used that contains the known concentrations of the pigmented samples in the database samples; entry Cmp is the concentration of each pigment P in pigmented sample m. The $n_m \times 2n_p$ matrix Σ has a row for each pigment (including the base material) and a column for each parameter in each wavelength band. The $n_m \times n_p$ matrix C has a row for each material in the database and a column for each pigment. With these definition, the matrix M=CΣ contains the material parameters for every material in the database.

To determine globally consistent material parameters for each of the pigments 106, the objective fitting function expressed in Eq. (15) is fit independently for each wavelength band and additionally summed over all the materials as provided in Eq. (20) below.

$$\sigma_{global}^\lambda = \operatorname*{argmin}_{\Sigma^\lambda} \sum_{m=1}^{n_m} F(R_d(\alpha_m^\lambda, \sigma_{t,m}^\lambda, d), \rho(\alpha_m^\lambda, \sigma_{t,m}^\lambda, d), \bar{R}_d^\lambda, \bar{\rho}^\lambda) \qquad \text{Eq. (20)}$$

Where in Eq. (20), Eq. (21) provided below is used.

$$\sigma_{s,m}^\lambda = \sum_{p=1}^{n_p} c_{mp} \sigma_{s,p}^\lambda, \ \sigma_{t,m}^\lambda = \sum_{p=1}^{n_p} c_{mp} \sigma_{t,p}^\lambda, \text{ and } \alpha_m^\lambda = \frac{\sigma_{s,m}^\lambda}{\sigma_{t,m}^\lambda}. \qquad \text{Eq. (21)}$$

Using Eqs. (20) and (21), and so that convergence of the equations arrives at the global minimum, the properties of the pigments in the initial phase may be estimated one at a time using one and two pigment dilution sets. As described above with respect to FIG. 2, the dilution sets include a pigmented sample that includes varying concentrations of a particular pigment color. In some embodiments the pigmented samples may for the dilution sets may include a colored pigment and a white pigment mixed in at a low concentration. Using the dilution sets and starting with a white color dilution set, Eq. (21) may be optimized by summing over the materials for that dilution set to determine the parameters of the base material and the particular pigment. Then, for each additional color dilution set, the parameters for the colored pigments are optimized using Eq. (21), but holding the white and base material properties fixed. The optimizations may be initialized by fitting a line to the scattering parameters of all the entries in a dilution set.

Figure 14B:
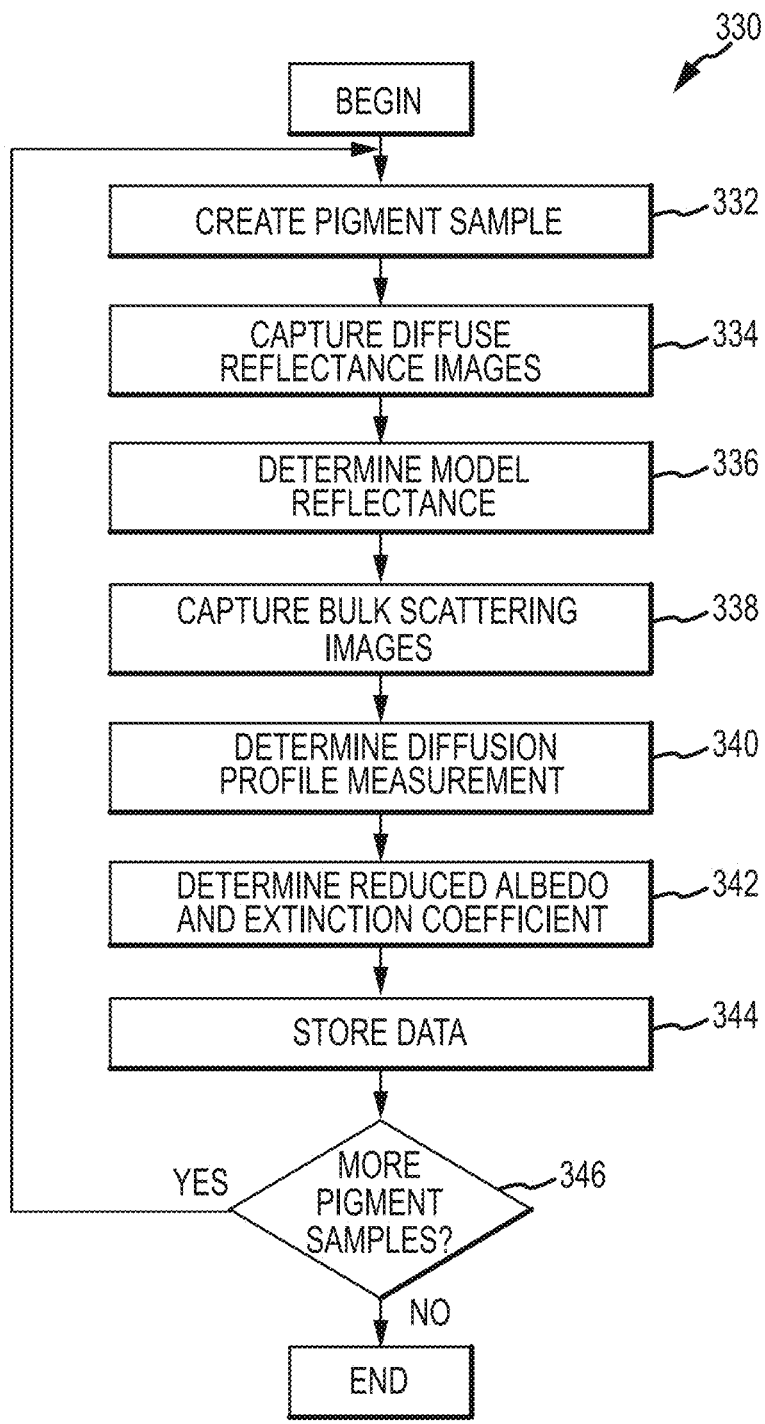
FIG. 14B is a flow chart illustrating a method for determining parameters correspondence to pigment particles of the target material sample corresponding to FIG. 1C.

A method for determining the scattering parameters for the pigment particles 106 and base material 104 within the pigmented sample 102 using the bulk scattering and diffusion profile measurements will now be discussed. FIG. 14B is a flow chart illustrating a method 330 for analyzing pigmented samples 102. The method 330 may begin with operation 332 and the pigmented sample 102 may be created. As discussed above with respect to FIGS. 2-3B, the pigment particles 106 may be mixed with the base materials 104, and the target material sample 106 may then be positioned within a securing device 108. As noted above, the pigment color and/or concentration within the base material 104 may be varied depending on the desired data to be collected.

Once the pigmented sample is created, the method 330 may proceed to operation 334 and the diffuse reflectance images may be captured. The spectral measurement device 210 and/or the diffuse reflectance test fixture 150 may be used to capture the diffuse reflectance image 154. After the diffuse reflectance image 154 is captured, the method 330 may proceed to operation 336. In operation 336, the reflectance radiance is determined. In particular, the processor 452 uses Eq. (14) to analyze the diffuse reflectance image 154 to determine the model (e.g., pigmented sample) reflectance. In this example, the reflected radiance of the sample is used to determine the diffuse reflectance.

After the diffusion reflectance or diffusion profile is determined, the method 330 may proceed to operation 338. In operation 338, the spectral measurement device may capture one or more bulk scattering images. The bulk scattering image 152 may be captured by selectively illuminating the pigmented sample 102 with the light source 115 positioned outside the field of view of the camera 118. In particular, as the pigmented sample is illuminated by the light source 115 positioned at location F, the light propagates through the pigmented sample 102 and the camera 118 captures an image illustrating the bulk scattering.

After operation 338, the method 330 may proceed to operation 340. In operation 340 the bulk, per-wavelength, diffusion profile measurement (bulk scattering profile) may be determined. For example, the bulk scattering image 152 may be analyzed to extract the horizontal scanline that is vertically aligned with the light source 115. This scanline is used as the bulk scattering profile.

Once bulk scattering profile (or bulk diffusion profile) is determined, the method 330 may proceed to operation 342. In operation 342, the diffusion profile and the bulk scattering may be used to determine reduced albedo and extinction coefficient of the pigmented sample 102. In other words, the measurements of the diffusion reflectance and the bulk scattering profile may be mapped to individual pigments to determine the optical properties for the individual pigments. This may include generally fitting the forward model to a single material, creating an initial guess, providing a non-linear optimization, and linearly related the pigment concentrations through a global pigment parameter estimation. During operation 342, the processor 452 may analyzing the diffuse reflectance and bulk scattering images using Eqs. (8)-(21).

Once the reduced albedo and extinction coefficient are determined, the method 330 may proceed to operation 344. In operation 344, the optical parameters for the particular pigmented sample 102 may be stored in memory 458 to create a pigment database. After the data has been stored corresponding the particular pigmented sample 102, the method 330 may proceed to operation 346. In operation 346, the user or the processor may determine whether there are additional pigmented samples to be tested. If, for example, additional colors and/or concentrations may be evaluated, the method 330 may return to operation 332 and a new pigmented sample may be created. However, if in operation 346 no additional pigmented samples will be created, the method 330 may proceed to an end state.

Target Material Properties Acquisition

Once the database of pigmented samples has been created or the optical parameters for select pigments have been determined, the methods of FIGS. 1A-1C may include testing the optical parameters of a target material that may be replicated with the pigments. The target material may be at least partially translucent and one or more optical parameters of the target material may be tested using similar methods and testing devices as those used for testing the pigmented samples 102.

Figure 12C:
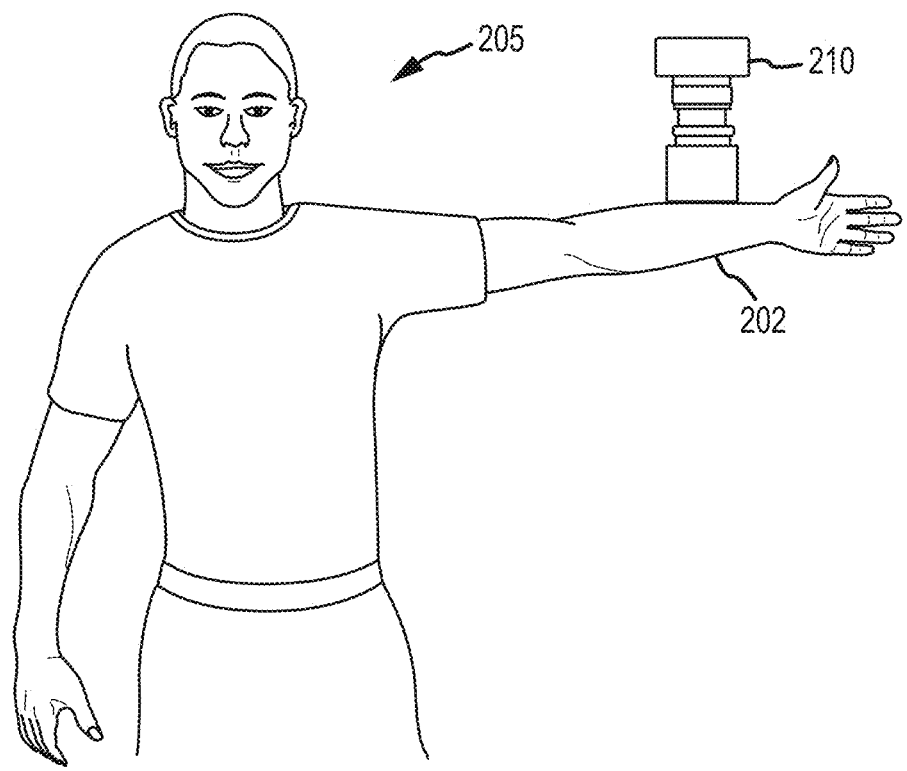
FIG. 12C is a perspective view of the spectral measurement device positioned on a portion of an arm of a user.
Figure 12D:
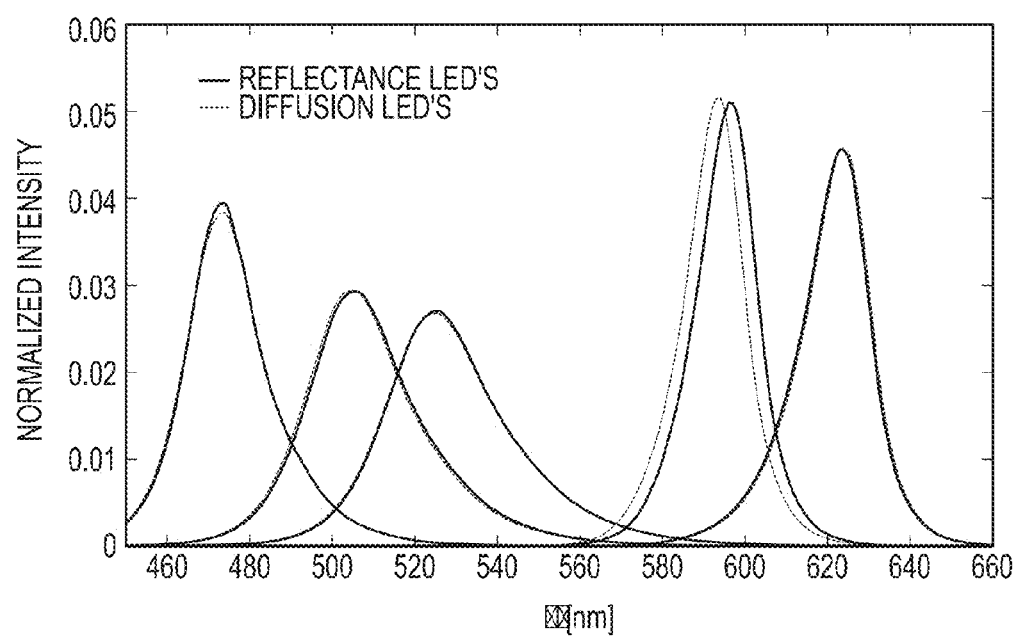
FIG. 12D is a graph illustrating a normalized spectral distribution function for the two groups of light sources used in the spectral measurement device of FIG. 12B.

In addition to capturing images of the pigmented samples 102, 103 and determining certain parameters of the pigmented samples 102, images of the target material may also be captured. These target images may be used to determine or estimate certain parameters of the target material, so that a replication material using the pigment particles 106 and/or base material 104 may be created having those or similar parameters. FIG. 12A is a perspective view of a spectral measurement device 210 positioned over a target material 202. FIG. 12B is a cross-section view of anther example of a spectral measurement device 210 taken along a line similar to 12B-12B in FIG. 12A, but in this example, the measurement device may perform both diffuse reflectance and bulk scattering measurements and may include one or more calibration elements. FIG. 12C is a front elevation view of the spectral measurement device positioned over a target material on a person. FIG. 12D is an example chart of a spectral distribution function for the light assemblies of the device. The spectral measurement device 210 includes the camera 118 having a lens 212 and the light source 116. In some examples, the light source 116 may include a plurality of optic fibers 214 positioned on a top surface of the device 210 and extending therethrough and a second set of optic fibers 215 also extending therethrough. The spectral measurement device 210 may also include a platform 216 that positioning the camera 118 above the target material 202 and prevents external light from entering into a field-of-view of the lens 212.

It should be noted that the spectral measurement devices 210 illustrated in FIGS. 12A and 12B may also be used to capture the diffuse reflectance image 154 of the pigmented sample 102. In these examples, the spectral measurement device 210 may position the camera 118 and light source 116 at substantially the same angles and positioned as described in the diffuse test fixture 150. Similarly, although the spectral measurement device 210 is discussed below with respect to the bulk scattering profile images, the spectral measurement device 210 may be used to capture diffuse reflectance images of the target material 202 as well. In this example, the target diffuse reflectance images may be substantially the same as the sample diffuse reflectance image 154 of the pigmented sample 102, except that they may capture the target sample 202 rather than the pigmented sample 102.

Moreover, it should be noted that the spectral measurement device 210 illustrated in FIGS. 12A-12C may allow for images to be captured of a target martial 202 of substantially any thickness and/or dimensions. For example, as shown in FIG. 12D, in some instances, the target material 202 may be the skin of a user 205, which may not be able to be diluted and/or modified. In these instances, the spectral measurement device 210 may provide data of the target material 202 without invasive contact (e.g., cutting or slicing into the target material). Furthermore, the spectral measurement device 210 may be used on small samples or large samples of target material 210. For example, the spectral measurement device 210 may have a larger camera 118, light source 116, and/or lens 212 for capturing larger target material 202 areas. Conversely, the spectral measurement device 210 may be more compact and configured to capture images of smaller target samples 202.

The spectral measurement device 210 may also be positioned on different areas of the target sample 210 to capture different images. For example, the spectral measurement device 210 may be slid along the skin of the user 205 to selectively capture different data points corresponding to the user 205.

With reference to FIGS. 12A and 12B, the spectral measurement device 210 may include five optic fibers 214 or cables configured to contact a first surface of the target material. The light source 116 may be positioned at an angle relative to the target material 202. For example, the light source 116 may be positioned at an angle of 45 degrees, relative to a surface normal of the target material 202. In other words, the angle between the surface normal of the target material and the illumination direction of the LEDs may be 45 degrees. For example, an opal glass diffuser may be positioned at an outgoing end of the fiber optic cables to ensure a constant angular intensity distribution on the target. Additionally, the light source 116 is configured to illuminate the target material (when activated) from outside the field-of-view of the lens 212. In instances where the target material 202 may be translucent or at least partially translucent, light from the light source 116 may propagate into the field-of-view of the camera 118. Further, the light may propagate into the field of view of the camera 118 may exponentially decrease as the distance from the light source 116 increases. This light propagation may allow the computer 450 to better determine the diffuse reflectance of the target sample 202 as the light position relative to the target material 202 within the spectral measurement device 210 may be known.

In some embodiments, the LEDs may include a plurality of colors or spectral distribution, whereas in other embodiments, the LED may include one or more light sources. With reference to FIG. 12D, in embodiments where the LEDs are multicolored, each LED may emit a different wavelength, such that a plurality of colors is represented.

In use, the spectral measurement device 210 is positioned adjacent and over a top surface of the target material 202. In some examples, the spectral measurement device 210 may be positioned in contact with the target material 202. The light source 116 may illuminate the target material 202 and the camera 118 may capture one or more images of the illuminated target material 202.

The two sets of fiber optic cables 214, 215 may both the diffuse reflectance and scattering profile of the target material to be captured without physically moving the target material or the spectral measurement device 210 between measurements. This may improve the reliability of the measurements, as well as facilitate automation of the testing process.

Test Measurement Examples

Figure 13A:
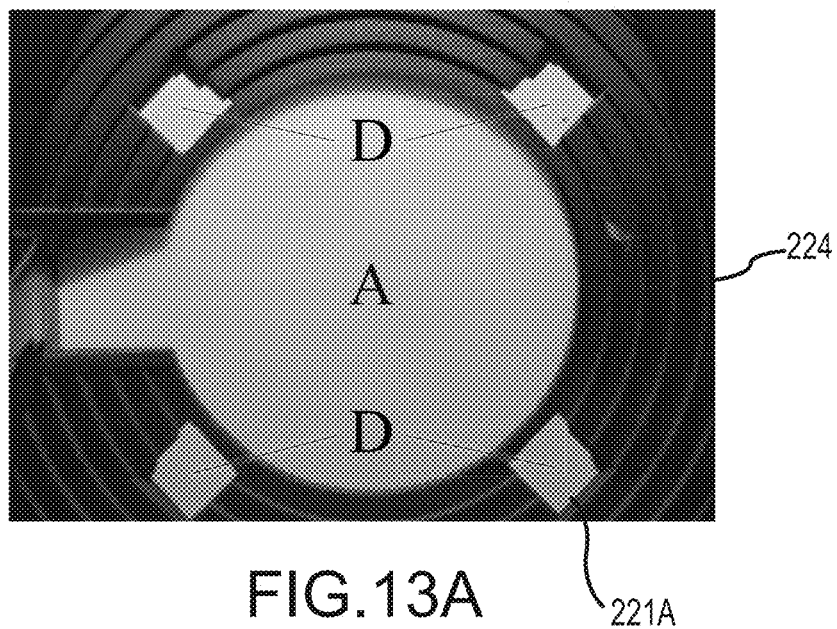
FIG. 13A is a front elevation view of a test image captured using the spectral measurement device during a diffuse reflectance measurement of a target material.
Figure 13B:
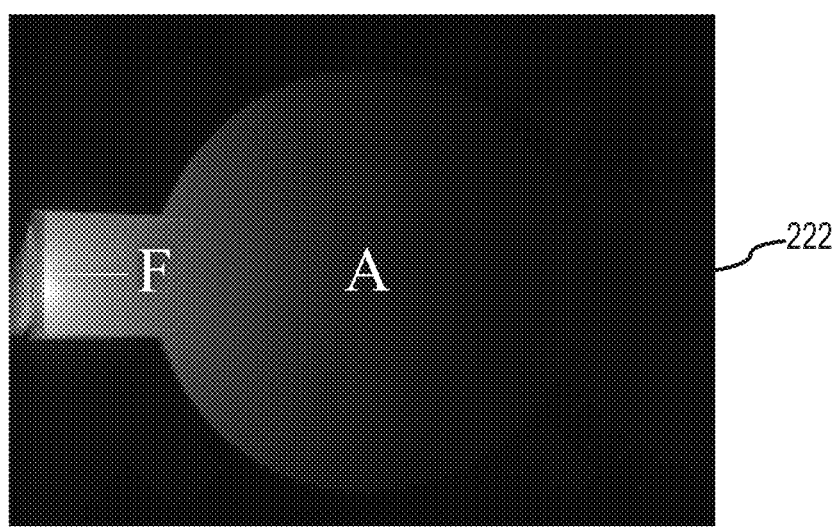
FIG. 13B is a front elevation view of a test image captured by the spectral measurement device during a diffusion profile measurement of a target material.

FIGS. 13A and 13B are perspective view of a target image 222 captured by the camera 118 while the light source 116 is illuminated. In some instances, the target image 222 may be a HDR image created from a plurality of exposures. To capture the diffuse reflectance measurement of the target material, the fiber optic cables 214 located at a top end of the spectral device and spatially separated from the target material. These optic cables 214 may be aimed towards a center of the target sample and may be set to have an illumination direction that is 45 degrees relative to the surface normal of the target material. Each LED is individually activated and the camera 118 captures an image. FIG. 13A is an example of a grayscale HDR image of a target material during a diffuse reflectance measurement. In some embodiments, reflectance standard patches 221 may be positioned on the sides of the target material and may then be used to estimate the irradiance ratio between the target sample and the reference reflectance patches 221, which may help determine the intensity of the LEDs. As briefly described above, the camera 118 may be configured to capture monochrome or grayscale images, in which case the LEDs may be colored. Alternatively, the camera may be configured to capture colored images, in which case the LEDs may be un-colored or white.

Once the images are captured, it may be assumed that the bidirectional reflectance distribution function (BRDF) is relatively diffuse, the per-channel diffuse reflectance can be extracted.

The device may also be used to determine the bulk scattering profile. In this example, the second set of optic fibers 215 may be used to illuminate the target material. The optic fibers may be configured to touch the target sample and illuminate the target material outside of the field of field of the camera 118. As the LEDs are illuminated, the light propagates through the scattering material and into the field of view of the camera 118. FIG. 13B is an example of a grayscale HDR image captured with one of the LEDs activated. Using the image, a horizontal scan line, vertically aligned with the activated light source, may be used to determine the bulk scattering profile. In other words, the bulk scattering profile (that is, the "reduced" or "bulk scattering properties") of the target material 202 may be a horizontal scan line in the target image 222 that may be vertically co-located with the light source 116. Thus, when analyzing the target image 222, the bulk scattering profile may be more easily determined. In some instances, the spectral measurement device 210 may not determine a light source intensity. However, a diffuse reflectance measurement (taken using the diffuse reflectance test fixture 150) may be combined with the target image 222 to determine a scale factor related to light source intensity. For example, an integral of the bulk scattering profile for each distance may correspond to the diffuse reflectance. Therefore, with the diffuse reflectance and the entire profile the missing scale factor of light intensity may be determined.

The techniques described herein for capturing the bulk scattering profile and diffuse reflectance of the target material may be substantially similar to the second example of capturing the optical parameters of the pigmented sample. In other words, both the target material and the pigmented sample, at least in some embodiments, may be tested using the spectral measurement device. In these embodiments, the images captured for both the target material and the pigmented sample may be analyzed in a similar manner.

Replication Material

Using the parameters determined for the various pigment particles 106 (by analyzing the target material samples 102) and the test images of the target material 202, a replication material may be created. The replication material may have substantially the same scattering parameters of the target material 202, and specifically subsurface scattering parameters, so that it may realistically model the appearance of the target material 202. Alternatively, the replication material may have an appearance that may be selected to match the appearance of the target material due to the subsurface scattering of the target and/or illumination sources on the target material. Generally, the replication material may be able to model target materials 202 that may be translucent, as the subsurface scattering parameters of the target material 202 may be replicated by the pigment particles 106.

Figure 15:
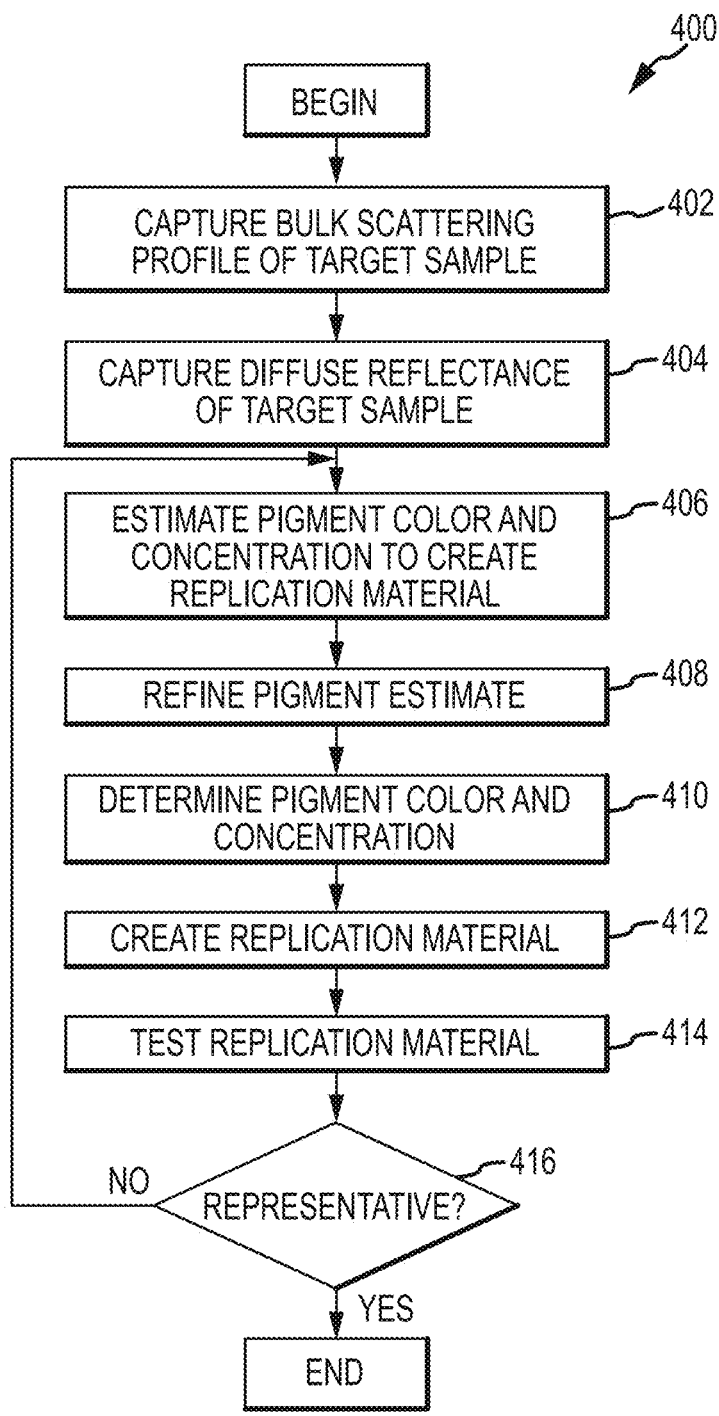
FIG. 15 is a flow chart illustrating a method for creating a replication material representative of the target material.
Figure 15A:
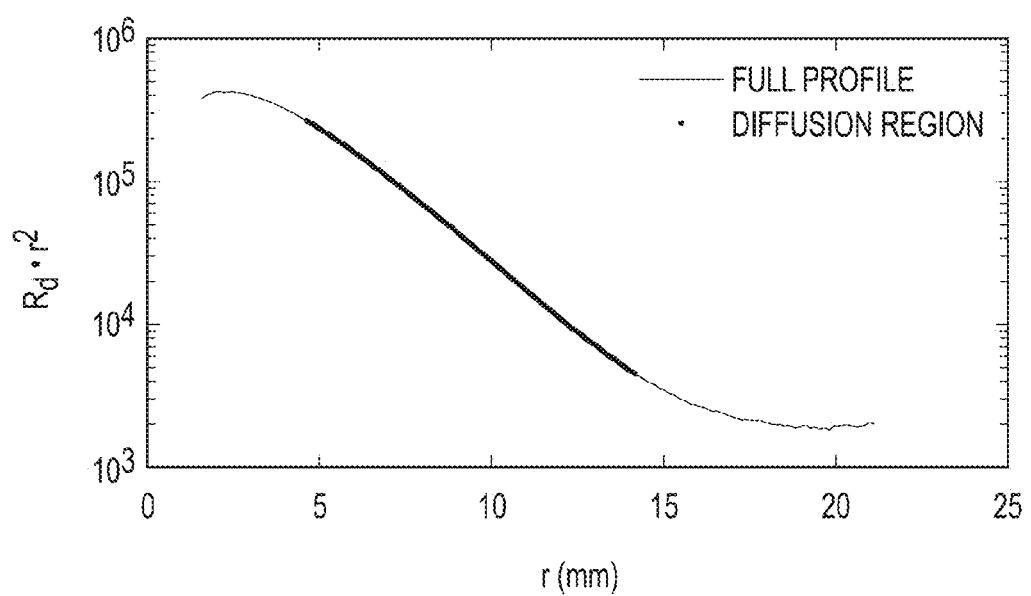
FIG. 15A is an example log plot of a measured bulk scattering profile as a function of distance.

FIG. 15 is a flow chart illustrating a method 400 for creating a replication material based on a target material. The method 400 may begin with operation 402 and the target image 222 may be captured with the spectral measurement device 210. The target image 222 may be used to capture the bulk scattering properties of the target material 202. As described above with respect to FIGS. 12A and 12B, because the spectral measurement device 210 may test the target material 202 without requiring invasive contact and may test thick samples, the target material 202 may be substantially any type of material. In some examples, the target material may be human skin, dentures or teeth, food items (meats, vegetables, fruits), shells, plastics, animal skin or exoskeletons, plants, fish, organisms (humans, animals, fish), marble, rocks, and other organic or non-organic materials. Further, although the replication material may model a translucent target material, the target material and thus the replication material may not be translucent. In other words, the disclosure herein may be used with substantially any type of target material, and not only those that are translucent.

Once the target image 222 has been captured, the method 400 may proceed to operation 404 and the diffuse reflectance of the target material 202 may be captured. For example, the camera 118, which may be incorporated into the spectral measurement device 210, may capture a diffuse reflectance image 154 of the target material 202.

Once the diffuse reflectance image 154 of the target material 202 has been captured, the method 400 may proceed to operation 406. In operation 406 the computer 450 may determine an estimate of the pigment particle 106 color and pigment concentration within the base material 104 in order to create the replication material. The estimate may be based on the diffuse reflectance image 154 and the target sample image 222 in which the bulk scattering properties and the diffuse reflectance of the target material 202 may be determined. Further, the computer 450 may also access the memory 458 and database of stored target material samples 102 in order to determine the initial set of pigment color and/or concentrations for creating the replication material.

Using the data from the target material 202, the computer 450 may estimate which pigment particles and concentrations could create same type of bulk scattering profile and diffuse reflectance as the target material 202. For example, a profile shape of the bulk scattering profile may be used to estimate the transport coefficient and a reduced albedo estimate may be based on the diffuse reflectance image 154.

For example, given the measured diffuse reflectance $\bar{\rho}^\lambda$ bulk scattering profile $\bar{R}_d^\lambda$ for the target material 202, the fitting process including the initial guess and non-linear optimization as described above using Eqs. (16)-(18) above can be used to estimate the $2n_\lambda$-vector of scattering parameters $$\hat{\Sigma} = [\hat{\sigma}_s^1 \ldots \hat{\sigma}_t^{n_\lambda}]^T$$

for the target material. Then, the processor may solve the linear system $c_i^T \Sigma = \hat{\Sigma}$ to get a p-vector of pigment concentrations $c_i = [\hat{c}_1 \ldots \hat{c}_{n_p}]^T$.

A fitting process may then be used to determine the pigment concentrations. As an example, using Eqs. (16)-(18), $C_i$ may be used as an initial guess and the predicted appearance of the target material 202 can be represented by Eq. (22) reproduced below.

$$c = \underset{c_1,\ldots,c_{n_p}}{\operatorname{argmin}} \sum_{\lambda=1}^{n_\lambda} F(R_d(\alpha^\lambda, \sigma_t^\lambda, d), \rho(\alpha^\lambda, \sigma_t^\lambda, d), \hat{R}_d^\lambda, \hat{\rho}^\lambda) \quad \text{Eq. (22)}$$

In Eq. (22), $\alpha^\lambda$ and $\sigma_t^\lambda$ may be defined by Eqs. (23) and (24), respectively. Eqs. (23 and (24) are listed below.

$$\sigma_s^\rho = \sum_{p=1}^{n_\lambda} c_p \sigma_{s,p}^\lambda \quad \text{Eq. (23)}$$

$$\sigma_s^\rho = \sum_{p=1}^{n_\lambda} c_p \sigma_{s,p}^\lambda. \quad \text{Eq. (24)}$$

Once an initial estimate of the pigment color and concentration has been created, the method 400 may proceed to operation 408 and the estimate may be refined. For example, a non-linear optimization process similar or the same as Eq. (7) and "fminsearch" in MATLAB may be used to optimize the estimate. Using Eq. (5), the unknown variables may be the concentrations of each pigment.

In another example, local pigment parameter estimation may be used for further refinement of the pigment concentrations. For example, in some instances, the forward model may not work well over the entire parameter range when using a single global set of pigment parameters. In particular, the forward model may be less accurate for materials having low optical thickness, low albedo, or anisotropically scattering materials. In these instances, a local refinement method may be used to find a set of pigment parameters that locally fits the samples in the database that may be the most similar to the target material 202. As an example, in determining the pigment recipe, the processor may apply a higher weight on the neighboring pigments with respect to the pigment concentration when estimating the effective pigment scattering parameters for finding the desired recipe.

In one implementation, an iterative procedure interleaves the parameter estimation Eqs. (19)-(21) with mixture optimization Eqs. (22)-(24), but in this case, row weights are used in the parameter estimation Eqs. (19)-(21) to bias the error to be lower for the neighboring mixtures already in the database. In some instances, the dot product of the normalized pigment concentration vectors between the currently predicted pigment concentrations and a database entry (excluding the base material) may be used to create the row weights.

Generally, the procedure for the local pigment parameter estimate may parallel the global optimization discussed with respect to Eqs. (19)-(20); however, using the local estimate, the objective function provided in Eq. (20) ire replaced by Eq. (25) provided below.

$$\sigma_{local}^\lambda(c) = \underset{\tilde{\Sigma}^\lambda}{\operatorname{argmin}} \sum_{m=1}^{n_m} \quad \text{Eq. (25)}$$

$$[(w^\lambda(c, c_m) + k_{reg}) F(R_d(\tilde{\alpha}_m^\lambda, \tilde{\sigma}_{t,m}^\lambda, d), \rho(\tilde{\alpha}_m^\lambda, \tilde{\sigma}_{t,m}^\lambda, d) \bar{R}_d^\lambda, \bar{\rho}^\lambda)]$$

In Eq. (25), the material parameters $\tilde{\alpha}$ and $\tilde{\sigma}_t$ are the local ones that are derived from the optimization variable $\tilde{\Sigma}^\lambda$. The $k_{reg}$ parameter regularizes the problem that even in k instances where some pigments are not used by the nearby samples, their parameters stay close to the global parameters. The regularization parameter $k_{reg}$ is set to sufficiently high enough (typically around $10^{-4}$ relative to a unit maximum) in order to stabilize the optimization, while low enough to not substantially affect the quality of the local fit.

Using Eq. (25), the weights $w^\lambda$ may be set using Eq. (26) listed below.

$$w^\lambda(c, c_m) = z_m^\lambda D_{mixture}(c, c_m) \quad \text{Eq. (26)}$$

In Eq. (26), the following Eq. (27) is used:

$$D_{mixture}(c_1, c_2) = \text{normalize}(c_1) = \text{normalize}(c_2) \quad \text{Eq. (27)}$$

In Eqs. (26) and (27), the weights cause the pigment estimation stage including Eq. (25) to find pigments that fit well to the database materials similar in composition to the target material 202 mixture, which results in better prediction of appearance for the optimized recipe. After a new recipe is determined, the weights may be updated and then the re-weighted systems may be repeatedly solved until convergence or for a maximum number of iterations. In one example, the maximum iterations may be set to 5; however, other maximum iterations may be selected.

After the pigment concentration and/or color estimate has been refined, the method 400 may proceed to operation 410 and the pigment color and pigment particle 106 concentration for the replication material may be determined. In particular, the resulting vector of Eq. (22) is c and may be the recipe that is used to replicate the appearance of the target material using the given pigment set and/or the recipe determined using the local refinement may be used that may alter the parameter process by weighting the pigments having an appearance more directly related to the target material when determining which recipe may create an appearance that may replicate the bulk scattering profile and/or diffuse reflectance of the target material.

It should be noted that the method may further include an optional operation where a user may modify the results to visually edit the recipe. In other words, the method may include an operation where a user may manually change the color and/or translucency of a desired target material and the computer system will output a recipe with concentrations of certain pigments such that when fabricated the target appearance will be matched. In these embodiments, the computer system may be configured to display a color editing module and a translucency editing module, where both modules may be configured to display a replica of the target material using digital colors that are converted from the pigment colors. The editing modules may allow a user to change the color, translucency, one or more pigment vectors, or other optical parameters across wavelength bands or may otherwise be configured to modify the recipe as selected by a user.

Figure 16:
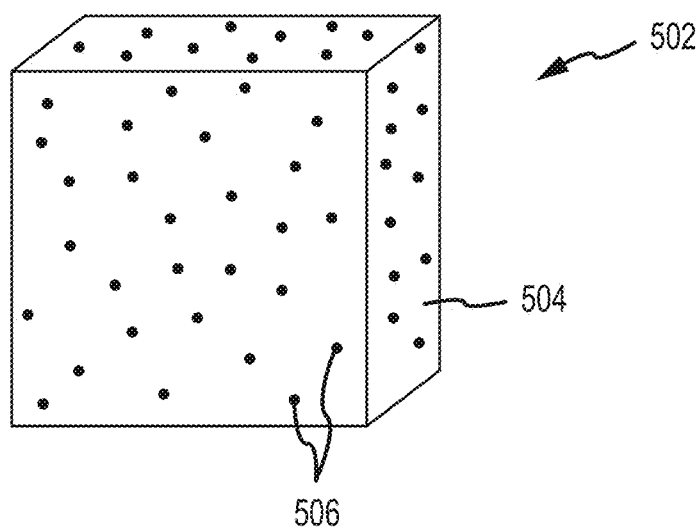
FIG. 16 is a perspective view of the replication material.

Using the concentration and color of the pigments, the method 400 may proceed to operation 412 and the replication material may be created. FIG. 16 is a perspective view of a replication material 502 created using a base material 504 and a concentration of pigment particles 506. In some examples, the base material 504 may be substantially the same as the base material 104. For example, the base material 104 may be a silicone, water, or other translucent materials. One example of the base material 504 may be a SortaClear40 Translucent, tin catalyzed RTV-2 silicone rubber by SILICONES, INC. In this example, the base material 504 may cure at room temperature and may only have a slight degree of shrinkage (approximately 0.1%). In this example, the base material 504 may require an additive such as GI-179 to catalyze the curing process. In some instances, the curing time may range between 16 hours to 7 days. However, it should be noted that other base materials 504 with various cure times, curing requirements and so on may also be used.

The pigment particles 506 may be added into the base material 504 to manipulate the appearance of the base material 504. In some instances there may be a variety of different colors of pigment particles 506 which may be added to the base material 504 in various concentrations. For example, the pigment particles 506 may be white, black, yellow, green, red, or blue. The concentration of the pigment particles 506, as determined in operation 410, may be used to determine the amount of each pigment color that could be combined with the base material 504.

In one example, the pigment particles 506 and optionally a catalyst maybe added to a weighing instrument. In order to insure the accurate amount of each the pigment particles and the catalyst, the pigment particles 506 may be added first and the weight of the weighing instrument may be reset and then the catalyst may be added. The base material 504 may then be added to the weighing instrument. Each of the elements may then be mixed together. This may allow the pigment particles 506 and/or catalyst to be more evenly dispersed throughout the base material 504.

In some instances, mixing the base material 504 and pigment particles 506 may introduce air into the base material 504. In these instances, the replication material 502 may be placed in a vacuum chamber or other device for removing the air introduced.

Figure 18:
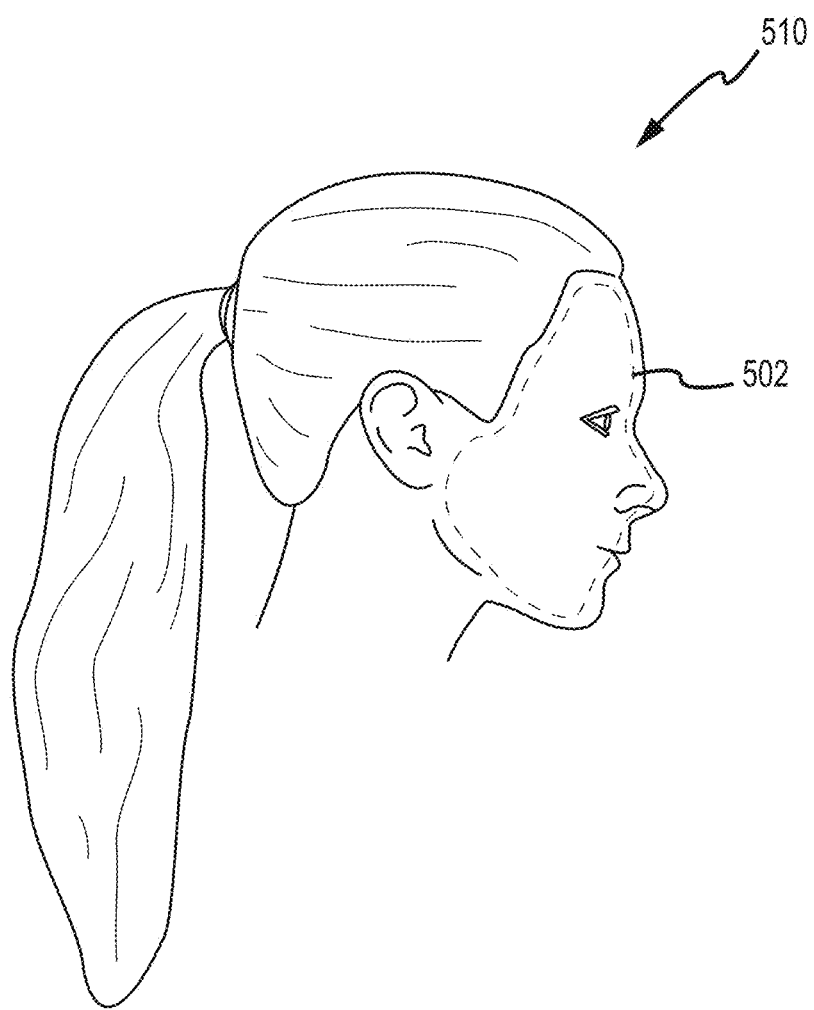
FIG. 18 is a perspective view of the replication material applied to a mold to create a human-like face.

The replication material 506 may then be molded into a desired shape. The shape of replication material 506 may vary depending on the desired target surface. FIG. 18 is a perspective view of the replication material 506 shaped as a human face 510. For example, in some instances the replication material 506 may be molded to conform around a shape of a animatronics robot, geometric mold, or the like. In some examples, the replication material 506 may be molded within the plates 114A, 114B so that the outer surfaces of the replication material 506 may be substantially smooth when removed from the mold. The smooth surface may better help to replicate the light scattering properties of the target material 202. However, in some instances, it may be desirable for the replication material 506 to have a rough surface.

In one example, the replication material 506 may be positioned within or on top of one of the plates 114A, 114B and then placed into a vacuum chamber or otherwise have the air removed. Then, the second plate 114B, may be pressed on to the first plate 114A. In some examples, more replication material 506 may be positioned on the first plate 114A than the mold of the plates 114A, 114B may actually contain. In this manner air bubbles within the replication material 506, which may alter the scattering properties, may be avoided. The second plate 114B may be loose, such that the replication material 506 may move the plate 114B to create space for the additional replication material 506.

In other instances, the replication material 506 may be molded in other manners. The type of molding and/or curing process may depend on the desired shape of the replication material 506. For example, if the target material 202 is a human face, the replication material 506 may be injection molded into a mold corresponding to the shape of the human face. In this example, the shape of the human face may be replicated by 3-D mapping techniques (e.g., polarization or plaster molds) and used to construct a mold for the replication material 506. See, for example, FIG. 19.

In some examples, the replication material 506 may be created from a homogenous layer that includes pigment particles mixed therein. In these examples, the replication material may have isotropic subsurface scattering properties. In some conventional material replication techniques multiple layers are used to create a material. However, in using these layers, the subsurface scattering is anisotropic in the direction of the layers, and thus only materials with heterogonous subsurface scattering properties can be replicated with accuracy. That said, in some instances, the layered approach may be combined with the homogenous layer described herein to create multiple layered materials that have isotropic subsurface scattering properties.

Figure 19:
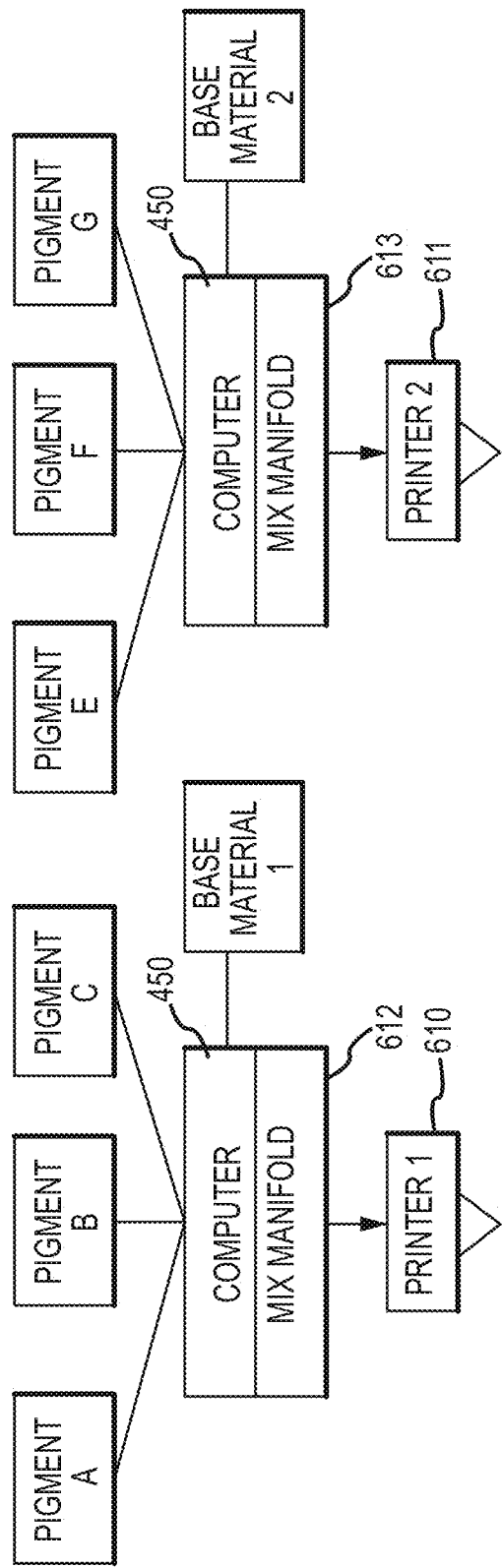
FIG. 19 is a block diagram illustrating a first and a second printer for creating one or more replication materials.

For example, the replication material 506 may be created out of one or more layers of different combinations of pigments. FIG. 19 is a block diagram illustrating a printer 610 for creating the replication material 502. The printer 610 may combine one or more pigment particles, shown as Pigment A, Pigment B, and/or Pigment C in various amounts as determined by the computer 450. A mixing manifold 612 may combine the various pigment particles 506 with the base material 504 to create a first replication material 512. A second printer 611 may combine one or more pigment particles, shown as Pigment E, Pigment F, Pigment G with a base material in a second mixing manifold 613. It should be noted that the pigment particles illustrated for either printer 611, 613 may be the same for each printer 611, 613 or may be different, depending on the desired target material to be replicated.

Figure 20:
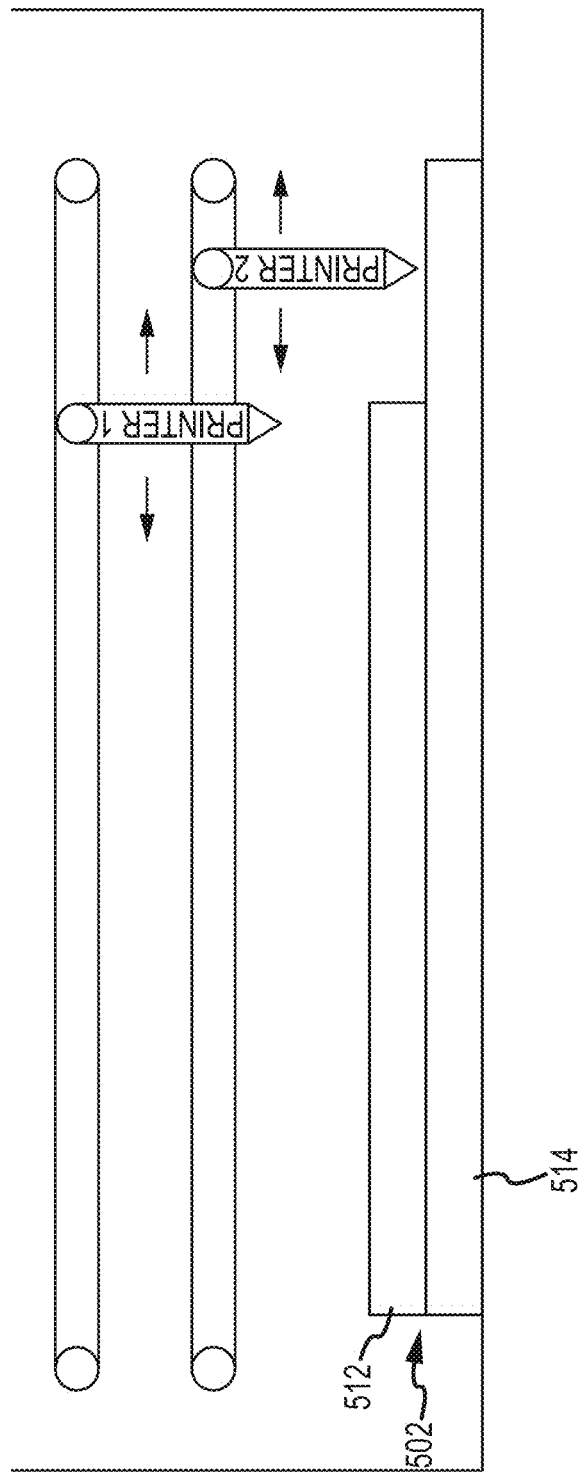
FIG. 20 is a side elevation view of the printers of FIG. 19 creating a layered replication material.

FIG. 20 is a simplified side elevation view of the printers 611, 613 creating the replication material 502. As shown in FIG. 20, the two printers 611, 613 may move spatially to create a first replication material layer 512 and a second replication material layer 514. The two layers 512, 514 may be combined to create the replication material 502, e.g., as shown in FIG. 18. In this manner, the replication material 502 may be better able to replicate translucent materials that may have one or more different portions and/or those translucent materials that may include different objects, colors, or the like underneath. For example, in replicating the human face as shown in FIG. 18, the one more replication layers 512, 514 may be layered to better replicate veins, moles, and so on that may be beneath or on top of skin of a person.

Furthermore, in other embodiments, the replication material 506 may be created virtually rather than physically. For example, the concentrations of the pigment particles 506 may be used to create a virtual model of the replication material 506. In these embodiments, the replication material 506 may be used for computer generated images or the like for simulated the target material. In these examples, the replication material 506 may be displayed by the computer 450 on the display 456.

With reference again to FIG. 15, once the replication material 506 is created, the method 400 may proceed to optional operation 414 and the replication material 506 may be tested. In some instances it may be desirable to test the replication material 506 to determine if the scattering properties of the replication material 506 replicate those of the target material 202. The replication material 506 may be tested in substantially the same manner as the pigmented sample 102. For example, the extinction coefficient test fixture 120, the forward scattering test fixture 130, the back scattering test fixture 140, and/or the diffuse reflectance test fixture 150 may be used to capture images in order to determine the scattering parameters of the replication material 506. In other examples, the replication material 506 may be as thick as the sample and so only the diffuse reflectance and bulk scattering profile may be tested.

After the replication material 506 has been tested, the method 400 may proceed to operation 416. In operation 416 the parameters of the replication material 506 may be compared by the computer 450 with the parameters of the target material 202 in order to determine if the replication material 506 is representative the target material 202. If the replication material 506 is not representative, the method 400 may return to operation 406 and another estimate for the pigment color and concentration may done. However, if in operation 416 the replication material 506 is representative, the method 400 may end.

It should be noted that the replication material 506 once representative of the target material may be used to replicate the target material. For example, the replication model 506 may be molded, as described above, to conform to substantially any shape and/or size. Furthermore, one more replication materials may be stitched or otherwise formed together to create a total target material. For example, if the target material is the skin of an entire person, the replication material for forming the hands may be different from the replication material forming the legs, etc. Similarly, even different layers and/or portions of certain areas of the target material may require more than one replication material attached together. For example, there may be a first replication material for forming an inner skin layer and a second replication material for forming an outer skin material, or there may a replication material for the hand but one area of the target hand may have a mole thus requiring a second replication material for that portion of the hand.

Example of Mapping Measurements to Pigments

Other examples of matching pigments to a target material and creating a replication material will now be discussed. These examples may be used with or instead of the examples discussed above. Once the target material 202 has been measured, the replication material 506 may be created that may match the appearance of the target material 202. In one embodiment, the appearance of the target material may be replicated by mixing one or more pigments into the base material. To determine the recipe or a vector containing a concentration for each available pigment, the computer 450 may predict the appearance (both the reflectance and the scattering profile) that will result from any given set of pigment concentrations. Mapping the recipe (or concentration of pigments) appearance may then be inverted to determine an optimization process that can match the recipe (e.g., pigment concentrations and colors) in order to match the appearance of the target material 202. The below discussion is an example of an optimization process that may be used to determine a recipe of pigments that will best match the appearance of the target material 202. The below process may be implemented in operations 406, 408, and 410 in the method 400 of FIG. 15.

As described above with respect to FIG. 14A, in some instances, a database of pigment concentrations may be created. In other words, it may be desirable to model the mapping from pigment concentrations $c_p$, p=1, ..., $n_p$ to the appearance characteristics $p^\lambda$ and $R_d^\lambda$, $\lambda=1, ..., n_\lambda$ of the target material. This model may be determined based on a database of appearance measurements of sample target materials (e.g., a number of example materials that can fabricated and measured). The database, such as the one described in operation 316 of method 300, may store a number of appearance measurements correlated to the various pigmented samples. This approach to modeling may leverage an approximate model based on diffusion to intelligently interpolate among the database samples and to provide starting points for nonlinear optimization of pigment concentrations.

The dipole model (described in more detail below) may provide a closed-form expression for subsurface reflectance between surface points x and y as a function of distance, as illustrated in Eq. (28) below:

$$\frac{dL_r^\lambda(x)}{d\Phi_i^\lambda(y)} = R_d(\alpha^\lambda, \sigma_t^\lambda; \|x-y\|), \qquad \text{Eq. (28)}$$

The dipole model may depend on both the reduced scattering albedo $\alpha$ and the reduce extinction coefficient $\sigma_t$ and operates separately for each wavelength band indexed by $\lambda$. A related model predicts total diffuse reflectance, is shown below in Eq. (29)

$$\frac{M_r^\lambda}{E_i^\lambda} = \rho(\alpha^\lambda) \qquad \text{Eq. (29)}$$

which depends only on the reduced scattering albedo and is again separate per wavelength band.

The dipole model may depend on both the reduced scattering albedo $\alpha$ and the reduce extinction coefficient $\sigma_t$ and operates separately for each wavelength band indexed by $\lambda$.

Given the measurements of $\overline{R}_d^\lambda$ and $\overline{\rho}^\lambda$ for any particular material, the parameters of the target material 202 can be estimated by fitting to the diffusion model, seeking a match in the (relative) diffusion profile and the (absolute) total reflectance using Eq. (30) below (which is the same as Eq. (15) above).

$$(\alpha^\lambda, \sigma_t^\lambda) = \underset{\alpha, \sigma_t}{\operatorname{argmin}} F(R_d(\alpha, \sigma_t), \rho(\alpha), \overline{R}_d^\lambda, \overline{\rho}^\lambda) \qquad \text{Eq. (30)}$$

-continued
$$F(R_d^1, \rho^1, R_d^2, \rho^2) = [D(R_d^1, R_d^2) + (\rho^1 - \rho^2)^2]$$

where D is a profile difference measure described in Eq. (31) below.

In some instances, this fitting approach could be used to determine the material parameters of each of the training examples (e.g., those used to create the database), from which the properties of each individual pigment could be derived. Then the parameters of the target material 202 could be determined in a second fit and used to find the pigment concentrations required. However, the diffusion approximation may not be accurate enough to directly achieve a visual match using this approach. The following discussion adapts this general idea into a multi-stage algorithm that takes advantage of constraints from the known concentrations of the database samples and relies on local, rather than global, fits to the training data.

Fitting the Diffusion Model to a Single Material

As described above with respect to Eq. (1), according to the theory of scattering media, a homogeneous material can be described by two parameters, the absorption coefficient $\sigma_\alpha$ and the scattering coefficient $\sigma_s$, or equivalently by the attenuation coefficient $\sigma_t = \sigma_\alpha + \sigma_s$ and albedo $\alpha = \sigma_s/\sigma_t$. If any two of these parameters are known the other two can be computed. In highly scattering materials, the flow of light can be modeled with a diffusion equation, which leads to analytical approximate models that can be used to describe translucent materials. In such materials, one can replace the scattering coefficient with the reduced scattering coefficient $\sigma_s'$, and then treat the scattering as isotropic.

A dipole diffusion model can be used for the scattering profile as shown below in Eq. (32) below.

$$R_d(\alpha, \sigma_t; r) = \frac{\alpha}{4\pi}\left[z_r(\sigma_{tr}d_r + 1)\frac{e^{-\sigma_{tr}d_r}}{d_r^3} + z_v(\sigma_{tr}d_v + 1)\frac{e^{-\sigma_{tr}d_v}}{d_v^3}\right] \quad \text{Eq. (32)}$$

In Eq. (32) above, $\sigma_{tr} = \sigma_t\sqrt{3(1-\alpha)}$, $z_r = 1/\sigma_t$, $z_v = z_r + (2/3)A/\sigma_t$, and $d_{r,v} = \sqrt{r^2 + z_{r,v}^2}$.

A model for total diffuse reflectance is illustrated in Eq. (33) below. Eq. (33) is derived from Flock's model, which as disused above with respect to Eqs. (5)-(7) may predict the diffuse reflectance of a highly scattering infinitely thick sample, given the reduce albedo and the index of refraction.

$$\rho(\alpha) = \frac{\alpha}{1 + 2A(1-\alpha) + (1+2A/3)\sqrt{3(1-\alpha)}} \quad \text{Eq. (33)}$$

In both models, Eq. (34) below can be used.

$$A = \frac{1 + F_{dr}}{1 - F_{dr}} \quad \text{Eq. (34)}$$

In Eq. (34) above, in instances where $F_{dr}$ is the hemispherically integrated reflectance of the Fresnel interface, Eq. (14) below can be empirically defined for refractive index n.

$$A(\eta) = 1.440\eta^{-2} + 0.710\eta^{-1} + 0.668 + 0.0636\eta \quad \text{Eq. (35)}$$

One fitting operation is to fit the diffusion model to the measured appearance data $\overline{Ri}_d^\lambda$ and $\overline{\rho}^\lambda$ for a single wavelength band of a single material. To find a starting point for the optimization, estimate $\alpha$ by solving (5) for $\rho(\alpha) = \overline{\rho}^\lambda$. Then, to find $\sigma_t$, an approximation as shown in Eq. (32) can be used and is valid for distances large compared to $1/\sigma_t$, this is shown in Eq. (36) below (which is the same as Eq. (16) above).

$$R_d(\alpha, \sigma_t; r) \approx k\frac{e^{-\sigma_{tr}r}}{r^2} \quad \text{Eq. (36)}$$

As shown in FIG. 5, this means that for large enough r a plot of log $(R_d r^2)$ against r may be a straight line with slope $-\sigma_{tr}$. By fitting this line to $\overline{R}_d^\lambda$, $\sigma_{tr}$ can be determined, and then using $\sigma_{tr}$, the extinction coefficient $\sigma_t$ may be determined using the estimated value of $\alpha$.

Starting from these estimated values for $\sigma_t$ and $\alpha$, the minimum of Eq. (30) may be computed. To compute the difference between two scattering profiles the metric expressed below as Eq. (37) can be used.

$$DR_d^1, R_d^2 = \frac{1}{r^1 - r_0}\int_{r_0}^{r_1}\left[(R_d^1(r)/\mu_1)^{\frac{1}{3}} - (R_d^2(r)/\mu_2)^{\frac{1}{3}}\right]^2 dr \quad \text{Eq. (37)}$$

In Eq. (37) above, $\mu_1$ and $\mu_2$ are the mean values of the profiles to allow for the unknown intensity of the light source in the diffusion profile measurement, and the interval $[r_0, r_1]$ is a range of distances over which the model is expected to fit well. This range is determined by shrinking the interval until a line fits within a given tolerance, and can be manually overridden to avoid any glitches in the measured profiles. FIG. 15A is a log plot of a measured bulk scattering profile as a function of distance. As shown in FIG. 15A, the range of the diffusion region is used to fit within the diffusion mode.

The process of fitting to a single profile produces material parameters that correspond to the observed appearance. However, the model may only be an approximate and in some instances the best-fit parameters may not be close to the true parameters of the material, particularly for low-albedo materials where the diffusion model is less accurate. To obtain more meaningful results larger collections of samples can be fitted at once.

As a final step in the single-material fitting process, the residual error for each wavelength band of each database sample can be summarized using a confidence $z^\lambda$ by using the formula expressed below in Eq. (38) (which is the same as Eq. (18) above).

$$z_m^\lambda = \min\left(\frac{\mu_d^\lambda}{d_m^\lambda - d_{75\%}^\lambda + \mu_d^\lambda}, 1\right) \quad \text{Eq. (38)}$$

In Eq. (38), where $d_m^\lambda$ is the residual (the minimum value of Eq. (30)) for the $m^{th}$ sample and wavelength band $\lambda$, $d_{75\%}^\lambda$ is $75^{th}$ percentile residual over the whole database for this wavelength, and $\mu_d^\lambda$ is the mean error for this wavelength over the entire database. This confidence can be used as a weight in fitting pigment parameters.

Measurement Database Selection

A beginning operation in estimating the pigment parameters is designing the input set or measurement database. As described above with respect to FIG. 14A, the per-channel diffuse reflectance measurement, $\bar{\rho}^\lambda$, the per-channel bulk scattering profile, $\bar{R}_d^\lambda$, for a set of samples with known pigment concentrations may be determined, and then the $\alpha^\lambda$ and $\sigma_t^\lambda$ for each pigment and base material (e.g., silicone) can be estimated.

When input set of pigments contains highly absorbing entries, one issue is that the design of database measurements will not violate the assumptions of diffusion theory that may be used to estimate their parameters. The two main assumptions for diffusion theory may be used are $\sigma_\alpha^\lambda \ll \sigma_t^\lambda$ and that the measured target has a large enough physical size, with respect to its optical thickness, such that an increase in any of its physical dimensions will not affect $\bar{\rho}^\lambda$ nor $\bar{R}_d^\lambda$.

In some embodiments, in the database measurements, scattering can be enforced which contain absorbing pigments by also mixing highly scattering white pigment. In matching the appearance of a semi-infinite slab, by using, for example, finite size slabs of size 10×10×3 cm, a lower bound can be forced on the optical thickness by adding 0.05% white pigment to all samples containing absorbing pigments.

Using the techniques and methods illustrated in FIG. 14A, each pigment may include one or more database entries or dilution sets. In some embodiments, for each pigment dilution, samples can be generated with varying concentrations of that pigment, but mixed with white pigment at the concentration of 0.05%.

Pigment Parameter Estimation

After the database has been created, as discussed above and with respect to FIG. 14A, the parameters of the database samples (each of which may consist of a known mixture of one or more pigments with the base material), the material parameters for each sample that are consistent with the appearance of that sample, but may not be globally consistent with the known pigment concentrations may be known. Thus, to get reliable predictions, the results of independent fitting may be used to initialize a larger fitting problem that finds material parameters for each pigment that are globally consistent with all samples in the database, under the assumption (Beer's law) of a linear relationship between pigment concentrations and the parameters of the mixture. This linear relationship can be succinctly expressed using a matrix $\Sigma$, which contains the properties of all samples in all wavelengths as illustrated below in Eq. (39).

$$\sum = \begin{bmatrix} \sum_1 \\ \vdots \\ \sum_{n_p} \end{bmatrix} \quad \text{Eq. (39)}$$

In Eq. (39) above, Eq. (40) (below) may represent the material parameters of the $p^{th}$ pigment, and a matrix C, which contains the known concentrations of all pigments in all database samples; entry $c_{mp}$ is the concentration of pigment p in sample m. The matrix $\Sigma$ has a row for each pigment (including the base material) and a column for each parameter in each wavelength; it is $n_p \times 2n_\lambda$. The matrix C has a row for each material in the database and a column for each pigment; it is $n_m \times n_p$. With these definitions, the matrix $M = C\Sigma$ contains the material parameters of every material in the database.

$$\sum_p = [\sigma_{s,p}^1 \ \sigma_{t,p}^1 \ \ldots \ \sigma_{s,p}^{n\lambda} \ \sigma_{t,p}^{n\lambda}] \quad \text{Eq. (40)}$$

To find globally consistent material parameters for the pigments, the objection function illustrated in Eq. (30) can be fitted, except summed over all materials and all wavelengths, and an optimization over the material parameters of the pigments can be used as illustrated below in Eq. (41):

$$\sum_{global} = \underset{\Sigma}{\text{argmin}} \sum_{m=1}^{n_m} \sum_{\lambda=1}^{n_\lambda} F(r_d(\alpha_m^\lambda, \sigma_{t,m}^\lambda), \rho(\alpha_m^\lambda), \bar{R}_d^\lambda, \bar{\rho}^\lambda) \quad \text{Eq. (41)}$$

where $$\sigma_{s,m}^\lambda = \sum_{p=1}^{n_p} c_{mp} \sigma_{s,p}^\lambda, \ \sigma_{t,m}^\lambda = \sum_{p=1}^{n_p} c_{mp} \sigma_{t,p}^\lambda,$$

and $$\alpha_m^\lambda = \frac{\sigma_{s,m}^\lambda}{\sigma_{t,m}^\lambda}.$$

To ensure convergence to the global minimum, in this initial phase the properties of the pigments can be estimated one at a time, using the one- and two-pigment dilution sets described above with respect to the database creation. In one embodiment, the white dilution set can be done first, optimizing Eq. (41), summing only over the materials in that set, for the properties of the base material and the white pigment. For each color dilution set, similarly optimize for the properties of the color pigment, holding the white and base materials fixed. These optimizations can be initialized by fitting a line to the scattering parameters (from the previous step) of all entries in the dilution set.

Mixture Optimization

One the parameters for each of the available pigments are known, a recipe to match the target material can be created. Given the measured diffuse reflectance $\hat{\rho}^\lambda$ and scattering profile $\hat{R}_d^\lambda$ for the target material, the fitting process described above may be used to estimate of the $2n_\lambda$-vector of scattering parameters $\hat{\Sigma}32\ [\hat{\sigma}_s^1 \ \ldots \ \hat{\sigma}_t^{n\lambda}]^T$ for the target mixture. The linear system $c_i^T \Sigma = \hat{\Sigma}$ can then be solved to get a p-vector of pigment concentrations $c_i = [\hat{c}_1 \ \ldots \ \hat{c}_{n_p}]^T$. Using $c_i$ as an initial guess, the predicated match is optimize to the target measurements (as described above with respect to FIG. 12B) using Eq. (42).

$$c = \underset{c_1,\ldots,c_{n_p}}{\text{argmin}} \sum_{\lambda=1}^{n_\lambda} F(R_d(\alpha^\lambda, \sigma_t^\lambda), \rho(\alpha^\lambda), \hat{R}_d^\lambda, \hat{\rho}^\lambda) \quad \text{Eq. (42)}$$

In Eq. (42) above, $\alpha^\lambda$ and $\sigma_t^\lambda$ are defined by Eq. (43) below.

$$\sigma_s^\lambda = \sum_{p=1}^{n_p} c_p \sigma_{s,p}^\lambda, \ \sigma_t^\lambda = \sum_{p=1}^{n_p} c_p \sigma_{t,p}^\lambda \quad \text{Eq. (43)}$$

The resulting vector c is the recipe to replicate the appearance of the target material using the given pigment set.

Local Refinement

The mapping of measurements to pigment concentrations as it is described above may assume that the diffusion model can globally fit the entire database with a single set of material parameters. However, in some instances, the residuals in fitting the whole database together are much higher than the residuals of fitting individual materials. Since the mixture optimization is matching the diffusion model to the target, it may only be as accurate as the fits of the model to similar materials in the database. A local refinement algorithm may then be used to determine a set of pigment parameters that fits well to the samples in the database and that are most similar to the target. The local refinement algorithm may be used while still using the global fitting process to ensure consistency to achieve meaningful interpolation between the captured samples. In some instances, a higher weight is applied on the neighbors, with respect to the pigment concentration, when estimating the "effective" pigment scattering parameters to be used in finding the recipe.

In some instances, an iterative procedure may be used that interleaves the parameter estimation and mixture optimization stages with the difference that row weights are used in the parameter estimation stage to bias the error to be lower for neighboring mixtures already in the database. In some embodiments, the dot product of the normalized concentration vectors, between the currently predicted pigment concentrations for target and a database entry may be used.

The procedure for the local pigment parameter estimation may parallel the global optimization and is shown below in Eq. (44). In Eq. (44) the material parameters $\tilde{\alpha}$ and $\tilde{\sigma}_t$ are the local ones (computed from the optimization variable $\Sigma$), whereas $\alpha$ and $\sigma$ are the global parameters (computed from $\Sigma_{global}$). The second term regularizes the problem so that even when some pigments are not used by the nearby samples, their parameters stay close to the global parameters. The regularization parameter $k_{reg}$ is set just high enough (around $10^{-3}$) to stabilize the optimization, while still low enough not to affect the quality of the local fit. Table 1, below, illustrates the global estimate of reduced scattering and absorption coefficients for pigments and base silicone used in an example fabrication process.

Table 1, below, illustrates the global estimate of reduced scattering and absorption coefficients for pigments and base silicone used in an example fabrication process.

TABLE 1

| | Reduced Scattering Coefficient ($\sigma_s$) | | | | | Absorption Coefficient ($\sigma_a$) | | | | |
| --- | --- | --- | --- | --- | --- | --- | --- | --- | --- | --- |
| | blue | cyan | green | orange | red | blue | cyan | green | orange | red |
| White | 1002.9 | 911.6 | 898.9 | 760.6 | 784.8 | 0.0 | 0.0 | 0.0 | 0.0 | 0.0 |
| Yellow | 0.0 | 19.9 | 111.4 | 69.6 | 94.4 | 26.4 | 2.0 | 0.4 | 0.4 | 0.4 |
| Red | 0.0 | 0.0 | 466.4 | 0.0 | 242.5 | 452.9 | 830.2 | 951.1 | 120.2 | 9.9 |
| Green | 0.0 | 152.0 | 231.0 | 0.0 | 0.0 | 24.4 | 12.1 | 17.9 | 163.0 | 259.2 |
| Blue | 3.2 | 0.0 | 0.0 | 0.0 | 0.0 | 42.3 | 79.9 | 140.6 | 986.2 | 910.6 |
| Black | 0.0 | 0.0 | 0.0 | 0.0 | 1.7 | 237.0 | 267.8 | 288.5 | 284.7 | 209.7 |
| Base | 0.079 | 0.082 | 0.041 | 0.058 | 0.012 | 0.002 | 0.002 | 0.002 | 0.001 | 0.001 |

$$\sum_{local} = \underset{\Sigma}{\mathrm{argmin}} \sum_{m=1}^{n_m} \sum_{\lambda=1}^{n_\lambda} \left[ \begin{array}{l} w_m^\lambda F\!\left(R_d(\tilde{\alpha}_m^\lambda, \tilde{\sigma}_{t,m}^\lambda), \rho(\tilde{\alpha}_m^\lambda), \overline{R}_d^\lambda, \overline{\rho}^\lambda\right) + \\ k_{reg} F\!\left( \begin{array}{l} R_d(\tilde{\alpha}_m^\lambda, \tilde{\sigma}_{t,m}^\lambda), \rho(\tilde{\alpha}_m^\lambda), \\ R_d(\alpha_m^\lambda, \sigma_{t,m}^\lambda), \rho(\alpha_m^\lambda) \end{array} \right) \end{array} \right] \quad \text{Eq. (44)}$$

In Eq. (44), above, the weights $w_m$ may be expressed as Eq. (45) below.

$$w_m = D_{appearance}(\overline{R}_{d,m}^\lambda, \overline{\rho}_m^\lambda, \hat{R}_d^\lambda, \overline{\pi}^\lambda) D_{mixture}(c, c_m) z_m^\lambda \quad \text{Eq. (45)}$$

In Eq. (24), Dappearance can be expressed by Eq. (46) below.

$$D_{appearance}(R_d^1, \rho^1, R_d^2, \rho^2) = \|\rho^1 - \rho^2\|_2^2 + \|\sigma_{tr}^1 - \sigma_{tr}^2\|_2^2 \quad \text{Eq. (46)}$$

In Eq. (46), may be expressed as Eq. (26) below.

$$D_{mixture}(c_1 c_2) = \mathrm{normalize}(c^1) \cdot \mathrm{normalize}(c^2) \quad \text{Eq. (47)}$$

These weights illustrated in Eqs. (44)-(47) allow pigment parameters to be determined during the pigment estimation stage that fit well to database materials with similar appearance and composition to the target mixture. This allows for a better prediction of appearance for the optimized recipe. After a new recipe has been found, the weights are updated and the re-weighted systems can be resolved until convergence or a number of iterations may be set, e.g., a maximum of 5 iterations. At convergence or the set number of iterations, the recipe may be determined that may best match the appearance of the target material.

Fabrication Example

Some specific examples of fabricating the replication material using a generated recipe are discussed in more detail below. Some challenges that can arise during fabrication are: ensuring that the correct amount of each pigment is added, avoiding air and other impurities, and finally ensuring that there is at least one side on the sample which appears near-specular. Using the techniques described herein, these issues may be reduced. In some examples, a hierarchical dilution process may be used to improve the concentration accuracy, reduce waste and streamline the fabrication process.

In one example, the base material may be silicone. Although, many other base materials may be used, silicon is used as it cures at room temperature with a shrinkage of generally less than 0.01%. In some instances, a two-component silicone rubber may be used which requires a catalyst, mixed in with a ratio 1:10, to activate the curing process. The curing is roughly 24 hours. The silicone is typically cured after 7 days.

The pigments may be silicone pigments, sample colors are White (Pantone White C), Yellow (RAL 1018), Red (Pantone Red C), Green (Pantone 3292), Blue (Pantone 2757C), Black (Pantone Black C). These pigments may be mainly absorbing, except for White, Yellow and Red, for which scattering is typically significant.

For fabricating the generated recipes, a hierarchical dilution scheme may be used. As a specific example of this scheme, for each pigment 1 kg master batches of 5% pigment concentration is produced. Depending on the pigment and base materials, this ratio may be the maximum ratio of pigment that may still allow the silicone to cure. To achieve a target concentration, the master batch may be diluted, in an iterative fashion, with base silicone. For example, the 5% mixture may be used the current dilution may be mixed with an equal amount of base silicone to half the pigment concentration. Once the concentration is roughly twice the target concentration for our recipe, the exact ratio of base silicon needed to achieve the desired target concentration may be mixed.

This dilution tree structure may be generated by a script using a bottom-up approach. Intermediate dilutions needed by some target recipes can be merged. In some embodiments, concentrations of pigments with absolute concentration less than $10^{-8}$ of the total sample weight, or less than 3 μg for a typical 300 g sample may be ignored. This process may also account for a catalyst that may be added at the very end for curing the final samples.

To ensure high accuracy, a minimum of 10 g of both dilution and base silicon when mixing and may be measured with a high accuracy digital balance. Though limiting the minimum weight may increase the number of steps, a relative accuracy lower bound of 1% at each dilution step may be achieved, and the relative error may be reduced with each dilution step by the mixing ratio.

In the mix preparation process, each of the ingredients may be weighed in the same container, one by one, by adding the correct amount of each ingredient and resetting the balance before proceeding to the next ingredient. Once all ingredients are added, the contents of the container may be stirred for a select period of time (e.g., several minutes) until the mixture is homogeneous. In some instances, mixing may add air. In these instances, the sample may be placed in a vacuum chamber to eliminate or reduce the air introduced therein. The created mixture may be poured into a mold and cured. In some embodiments, the mold may be created from smooth, near secular surfaces, which may result in better compliance with diffusion theory.

Perceptual Extension

In some instances, the recipe that best replicates the appearance of the target material 202 can be modified based on how humans perceive color and translucency, which may create a less technically accurate representation of the target material, but may create an appearance for the replication material that to a human more accurately represents the target material. In particular, the process may match the appearance of a target material based on the human brain's perception of color and translucency under a known illuminate or illumination source, rather than fitting the raw measurement data.

In one implementation, the appearance distance metric (Eq. 22) is changed from weighting all spectral bands equally to a perceptual distance that allows exploiting metamers. This makes use of the fact that although two spectral distribution functions may be different, they can be perceived identically by humans. Specifically, Eq. (22) may be changed such that the distance F is replaced with the perceptual distance $\tilde{F}$ and results in Eq. (48) below.

$$\bar{c} = \underset{c_1,\ldots,c_{n_p}}{\operatorname{argmin}} \ \tilde{F}(R_d(\tilde{\alpha}, \tilde{\sigma}_t, d), \rho(\tilde{\alpha}, \tilde{\sigma}_t, d), \tilde{R}_d, \tilde{\rho}) \qquad \text{Eq. (48)}$$

In Eq. (48) above, the diffusion profile measurement $\tilde{p}^\lambda$ and the bulk scattering profile Rare measurement $R_d^\lambda$ are projected into a human perceptual color space, such as CIELAB, which may be denoted as $\tilde{R}_d$ and $\tilde{p}$ in Eq. (48). In some instances, a reference illuminate is needed to convert to the perceptual color space and in these instances the replicated material may best be matched when illuminated with the illuminated that are used for the optimization. In other words, when modifying the recipe to match the appearance of the target materials 202 based on a perceived color space, the replicated material may also have to be illuminated by the same light sources that illuminated the target material 202 when tested. The perceptual distance $\tilde{F}$ is a weighted sum of two terms as expressed by Eq. (49) below.

$$\tilde{F}(R_d,\rho,\tilde{R}_d,\tilde{\rho}) = [w_T DE_{00}(\rho,\tilde{\rho})^2 + w_r \tilde{E}(R_d,\tilde{R}_d)] \qquad \text{Eq. (49)}$$

In Eq. (49), $W_r DE_{00}(\rho,\tilde{\rho})^2$ is a perceptual reflectance distance and $w_r \tilde{E}(R_d,\tilde{R}_d)$ is the perceptual translucency distance or profile shape. In some instances a relative of weight $w_t/w_r=25$ may be used in weighting the two distances. The perceptual reflectance distance and the perceptual translucency distance will each be discussed in turn below.

The perceptual reflectance distance can be determined by first determining the spectral radiance estimates of the target material 202 and the replica (which may be the selected illuminate for the perceptual color space). Then, given the spectral radiance estimates of the target sample and the replica material, the raw measurements of the diffuse reflectance $\tilde{p}^\lambda$ in CIELAB (denoted as $\tilde{p}$) and estimate their color distance using the perceptual metric CIEDE2000. It should be noted that the spectral reflectance distribution estimates can be determined by measuring the reflectance measurement directly (e.g., via a spectrometer) or by using spectral Eigen vectors trained on the pigment database.

The perceptual translucency distance is determined by converting the non-linear optimization equation, Eq. (17) into a perceptual distance metric for translucency. This may be done by performing an unconstrained fit of the forward model on the reflectance partial profile measurements $R_d^\lambda$. Then, using the model values to extrapolate the 5D profiles. In some instances, this type of fit may be used because often the first few millimeters of certain profiles may be occluded due to characteristics, such as a wall or the like, in the measurement device during measurement. However, in instances where the profiles are not occluded, different fitting techniques may be used. After fitting, the extrapolated 5D profiles are converted to CIELAB (denoted as $\tilde{R}_d$) and the integral of the CIEDE200 squared distance for all measured profile locations expressed as Eq. (50) is processed by the processor.

$$\tilde{E} = (R_d, \tilde{R}_d) = \frac{1}{r_1 - r_0} \int_{r_0}^{r_1} DE_{00}(R_d(r), \tilde{R}_d(r))^2 \, dr \qquad \text{Eq. (50)}$$

Using the above techniques, the recipe for replicating the appearance of the target material 202 can be modified to better match the target material 202 as it appears to a human. This technique allows for a better match of the target material appearance as seen by humans due to the fact that humans have a limited visible color spectrum and certain colors may appear different to humans than to other creatures. It should be noted that the techniques described herein for modifying the recipe for replicating a target material based on a desired color spectrum or visual characteristics may be applied to other spectrums than humans. For example, depending on the desired application of the replicated material, the recipe may be weighted or otherwise modified as described above to more accurately represent the target material under specific illuminate or other conditions. As such, the discussion of any particular color space is meant as illustrative only.

CONCLUSION

The foregoing description has broad application. For example, while examples disclosed herein may focus on using test fixtures to capture images used to determine the various parameters for a gamut of pigments, it should be appreciated that the concepts disclosed herein equally apply to directly replicating a material without requiring a retest the gamut of pigments each time. In other words, after a database or a collection of pigment scattering parameters has been determined using the measurement techniques, a replication material may be created by testing only the target material. Furthermore, while examples disclosed herein may focus on manually creating the replication material, the concepts disclosed herein may equally apply to other manufacturing techniques, such as 3-D printing or 3-D virtual modeling. Also, while the examples disclosed herein may tend to focus on the recreating translucent materials, these concepts apply to other non-translucent or opaque materials as well. Accordingly, the discussion of any embodiment is meant only to be exemplary and is not intended to suggest that the scope of the disclosure, including the claims, is limited to these examples.

In methodologies directly or indirectly set forth herein, various steps and operations are described in one possible order of operation but those skilled in the art will recognize the steps and operation may be rearranged, replaced or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for replicating the appearance of an at least partially translucent target material, comprising:
    receiving one or more optical characteristic data related to at least one target subsurface scattering parameter of the target material;
    referencing parameter data correlating to subsurface scattering parameters of a plurality of pigments within one or more pigmented samples; and
    determining a replication pigment concentration recipe from at least the parameter data correlating to subsurface scattering parameters of the one or more pigmented samples to replicate the appearance of the target material caused by at least one target subsurface scattering parameter, wherein the pigment concentration recipe comprises a mixture of at least two pigments of the plurality of pigments; and
    creating a physical model of a replication material by combining a pigment with a base material based on the replication pigment concentration recipe.

2. The method of claim 1, wherein the optical characteristic data is at least one of a diffuse reflectance or a bulk scattering profile.

3. The method of claim 2, wherein determining the replication pigment concentration recipe is performed by a processor, and further comprises comparing at least one of the diffuse reflectance value and the bulk scattering profile with a simulated appearance based in part on the parameter data correlating to the subsurface scattering parameters of the plurality of pigmented samples.

4. The method of claim 3, further comprising executing by the processor an optimization process to determine the pigment concentration.

5. The method of claim 3, further comprising evaluating a target material using a spectral measurement device.

6. The method of claim 5, wherein the spectral measurement device comprises:
    a camera; and
    a light source positioned at an angle from the camera and configured to illuminate at least a portion of the target material outside of a field-of-view of the camera.

7. The method of claim 6, wherein
    the camera is monochromatic; and
    the light source comprises a plurality of lights having different spectral properties.

8. The method of claim 6, wherein the camera is sensitive to different light wavelengths.

9. The method of claim 1, wherein the optical characteristic data comprises a bulk scattering diffusion.

10. The method of claim 1, wherein determining the pigment concentration is performed by a processor, and the operation of creating the replication material comprises displaying on a display a computer generated graphic model, wherein the display is in communication with the processor.

11. The method of claim 10, further comprising receiving user input to optimize the pigment concentration.

12. The method of claim 1, wherein the physical model of the replication material is created using a three-dimensional printer.

13. The method of claim 1, wherein the operation of creating the replication material further comprises creating a first replication element and a second replication element.

* * * * *

UNITED STATES PATENT AND TRADEMARK OFFICE
CERTIFICATE OF CORRECTION

PATENT NO. : 9,939,377 B2
APPLICATION NO. : 13/935712
DATED : April 10, 2018
INVENTOR(S) : Marios Papas et al.

Page 1 of 1

It is certified that error appears in the above-identified patent and that said Letters Patent is hereby corrected as shown below:

On the Title Page

In Assignee Section, delete "DISNEY ENTERPRISES, Burbank, CA (US)" and insert -- DISNEY ENTERPRISES, Burbank, CA (US) and ETH ZURICH (EIDGENOESSISCHE TECHNISCHE HOCHSCHULE ZURICH) (Switzerland) --

Signed and Sealed this
Twenty-first Day of August, 2018

Andrei Iancu
*Director of the United States Patent and Trademark Office*